US009120869B1

(12) United States Patent
Adams et al.

(10) Patent No.: US 9,120,869 B1
(45) Date of Patent: Sep. 1, 2015

(54) SYNTHETIC ANTIGEN BASED ON THE LIGAND DOMAIN OF THE PLASMODIUM VIVAX DUFFY BINDING PROTEIN

(71) Applicants: John H. Adams, Tampa, FL (US);
Francis B. Ntumngia, Tampa, FL (US);
Jesse L. Schloegel, Five Dock (AU);
Samantha J. Barnes, Tampa, FL (US);
Amy M. McHenry, Keene, TX (US);
Patchanee Chootong, Bangkok (TH)

(72) Inventors: John H. Adams, Tampa, FL (US);
Francis B. Ntumngia, Tampa, FL (US);
Jesse L. Schloegel, Five Dock (AU);
Samantha J. Barnes, Tampa, FL (US);
Amy M. McHenry, Keene, TX (US);
Patchanee Chootong, Bangkok (TH)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 0 days.

(21) Appl. No.: 14/224,265

(22) Filed: Mar. 25, 2014

Related U.S. Application Data

(62) Division of application No. 13/589,253, filed on Aug. 20, 2012, now Pat. No. 8,784,832.

(60) Provisional application No. 61/525,412, filed on Aug. 19, 2011.

(51) Int. Cl.
*A61K 39/015* (2006.01)
*C07K 14/445* (2006.01)

(52) U.S. Cl.
CPC .............. *C07K 14/445* (2013.01); *A61K 39/015* (2013.01)

(58) Field of Classification Search
CPC ........................... A61K 39/015; C07K 14/445
USPC ..................... 424/191.1, 268.1; 530/350, 300
See application file for complete search history.

(56) References Cited

U.S. PATENT DOCUMENTS

| 6,962,987 | B2 | 11/2005 | Sim et al. |
| 2009/0196883 | A1 | 8/2009 | Yadava et al. |
| 2010/0062028 | A1 | 3/2010 | Cohen et al. |
| 2010/0119539 | A1 | 5/2010 | Valderama Aguirre et al. |

OTHER PUBLICATIONS

Houghten et al. (Vaccines, 1986, Edited by Fred Brown: Cold Spring Harbor Laboratory).
Cole-Tobian et al 2002, Journal of Infectious Diseases, 186(4), 531-539.
Arevalo-Herrera et al. Immunogenicity and Protective Efficacy of Recombinant Vaccine Based on the Receptor-Binding Domain of the Plasmodium Vivax Duffy Binding Protein in Aotus Monkeys. Am. J. Trop. Med. Hyg., 73(Suppl 5), 2005, pp. 25-31.
Adams, J. H., D. E. Hudson, M. Torii, G. E. Ward, T. E. Wellems, M. Aikawa, and L. H. Miller. 1990. The Duffy receptor family of Plasmodium knowlesi is located within the micronemes of invasive malaria merozoites. Cell 63:141-53.
Adams, J. H., B. K. Sim, S. A. Dolan, X. Fang, D. C. Kaslow, and L. H. Miller. 1992. A family of erythrocyte binding proteins of malaria parasites. Proc Natl Acad Sci U S A 89:7085-9.
Ampudia, E., M. A. Patarroyo, M. E. Patarroyo, and L. A. Murillo. 1996. Genetic polymorphism of the Duffy receptor binding domain of Plasmodium vivax in Colombian wild isolates. Mol Biochem Parasitol 78:269-72.
Arevalo-Herrera M, Chitnis C, Herrera S (2010) Current status of Plasmodium vivax vaccine. Human vaccines 6: 124-132.
T. Bai et al., Proc Natl Acad Sci U S A 102, 12736 (Sep. 6, 2005).
Barnwell, J. W., and S. P. Wertheimer. 1989. Plasmodium vivax: Merozoite antigens, the Duffy blood group, and Erythrocyte invasion. Prog Clin Biol Res 313:1-11.
Ceravolo, I. P., B. A. Sanchez, T. N. Sousa, B. M. Guerra, I. S. Soares, E. M. Braga, A. M. McHenry, J. H. Adams, C. F. Brito, and L. H. Carvalho. 2009. Naturally acquired inhibitory antibodies to Plasmodium vivax Duffy binding protein are short-lived and allele-specific following a single malaria infection. Clin Exp Immunol 156:502-10.
Chitnis, C. E., and L. H. Miller. 1994. Identification of the erythrocyte binding domains of Plasmodium vivax and Plasmodium knowlesi proteins involved in erythrocyte invasion. J Exp Med 180:497-506.
Chootong, P., F. B. Ntumngia, K. M. VanBuskirk, J. Xainli, J. L. Cole-Tobian, C. O. Campbell, T. S. Fraser, C. L. King, and J. H. Adams. 2010. Mapping epitopes of the Plasmodium vivax Duffy binding protein with naturally acquired inhibitory antibodies. Infect Immun 78:1089-95.
Cole-Tobian, J., and C. L. King. 2003. Diversity and natural selection in Plasmodium vivax Duffy binding protein gene. Mol Biochem Parasitol 127:121-32.
Coley A. M. et al., Infection and immunity 74, 2628 (May, 2006).

(Continued)

*Primary Examiner* — Padma V Baskar
(74) *Attorney, Agent, or Firm* — Thomas|Horstemeyer, LLP

(57) ABSTRACT

The disclosure provides compositions that are useful for eliciting a strain-transcending immune response in an animal or human directed against the blood-stage of the malarial parasite *Plasmodium vivax*. The compositions are based on the ligand domain of *Plasmodium vivax* Duffy binding protein (PvDBPII). Polar charged polymorphic residues within the dominant strain-specific B-cell epitope were mutated to uncharged residues (e.g. serine, alanine and threonine). This DEKnull variant of PvDBPII produced in bacteria can be purified and refolded in vitro to mimic conformation and erythrocyte binding function of native DBPII. Immunogenicity of DEKnull was confirmed by administration to mice. Compared to the naturally-occurring, strain variant DBPII, DEKnull elicits antibodies that are more broadly reactive with different strain variants of DBPII and enhances production of functional inhibitory antibodies to the shared protective epitopes of native DBPII.

6 Claims, 53 Drawing Sheets

(56) References Cited

OTHER PUBLICATIONS

Crewther PE, Matthew ML, Flegg RH, Anders RF (1996) Protective immune responses to apical membrane antigen 1 of Plasmodium chabaudi involve recognition of strain-specific epitopes. Infect Immun 64: 3310-3317.

Dutta, S., J. R. Daugherty, L. A. Ware, D. E. Lanar, and C. F. Ockenhouse. 2000. Expression, purification and characterization of a functional region of the Plasmodium vivax Duffy binding protein. Mol Biochem Parasitol 109:179-84.

Fraser, T., P. Michon, J. W. Barnwell, A. R. Noe, F. Al-Yaman, D. C. Kaslow, and J. H. Adams. 1997. Expression and serologic activity of a soluble recombinant Plasmodium vivax Duffy binding protein. Infect Immun 65:2772-7.

Grimberg, B. T., R. Udomsangpetch, J. Xainli, A. McHenry, T. Panichakul, J. Sattabongkot, L. Cui, M. Bockarie, C. Chitnis, J. Adams, P. A. Zimmerman, and C. L. King. 2007. Plasmodium vivax invasion of human erythrocytes inhibited by antibodies directed against the Duffy binding protein. PLoS Med 4:e337.

Chitnis, C. E., A. Chaudhuri, R. Horuk, A. O. Pogo, and L. H. Miller. 1996. The domain on the Duffy blood group antigen for binding Plasmodium vivax and P. knowlesi malarial parasites to erythrocytes. J Exp Med 184:1531-6.

Cole-Tobian JL, Cortes A, Baisor M, Kastens W, Xainli J, et al. (2002) Age-acquired immunity to a Plasmodium vivax invasion ligand, the duffy binding protein. J Infect Dis 186: 531-539.

Haynes, J. D., J. P. Dalton, F. W. Klotz, M. H. McGinniss, T. J. Hadley, D. E. Hudson, and L. H. Miller. 1988. Receptor-like specificity of a Plasmodium knowlesi malarial protein that binds to Duffy antigen ligands on erythrocytes. J Exp Med 167:1873-81.

Healer J. et al., Mol Microbiol 52, 159 (Apr. 2004).

W. G. Kho, J. Y. Chung, E. J. Sim, D. W. Kim, W. C. Chung, Korean J Parasitol 39, 143 (Jun. 2001).

King, C. L., P. Michon, A. R. Shakri, A. Marcotty, D. Stanisic, P. A. Zimmerman, J. L. Cole-Tobian, I. Mueller, and C. E. Chitnis. 2008. Naturally acquired Duffy-binding protein-specific binding inhibitory antibodies confer protection from blood-stage Plasmodium vivax infection. Proc Natl Acad Sci U S A 105:8363-8.

Mendis K, Sina BJ, Marchesini P, Carter R (2001) The neglected burden of Plasmodium vivax malaria. Am J Trop Med Hyg 64: 97-106.

Miller, L. H., S. J. Mason, D. F. Clyde, and M. H. McGinniss. 1976. The resistance factor to Plasmodium vivax in blacks. The Duffy-blood-group genotype, FyFy. N Engl J Med 295:302-4.

Michon, P., T. Fraser, and J. H. Adams. 2000. Naturally acquired and vaccine-elicited antibodies block erythrocyte cytoadherence of the Plasmodium vivax Duffy binding protein. Infect Immun 68:3164-71.

Miller, L. H., S. J. Mason, J. A. Dvorak, M. H. McGinniss, and I. K. Rothman. 1975. Erythrocyte receptors for (Plasmodium knowlesi) malaria: Duffy blood group determinants. Science 189:561-3.

Mueller I, Galinski MR, Baird JK, Carlton JM, Kochar DK, et al. (2009) Key gaps in the knowledge of Plasmodium vivax, a neglected human malaria parasite. The Lancet infectious diseases 9: 555-566.

Pizarro J. C. et al., Science 308, 408 (Apr. 15, 2005).

Price RN, Tjitra E, Guerra CA, Yeung S, White NJ, et al. (2007) Vivax malaria: neglected and not benign. Am J Trop Med Hyg 77:79-87.

Ranjan, A., and C. E. Chitnis. 1999. Mapping regions containing binding residues within functional domains of Plasmodium vivax and Plasmodium knowlesi erythrocyte-binding proteins. Proc Natl Acad Sci U S A 96:14067-72.

Sim BK, Chitnis CE, Wasniowska K, Hadley TJ, Miller LH (1994) Receptor and ligand domains for invasion of erythrocytes by Plasmodium falciparum. Science 264: 1941-1944.

Singh AP, Puri SK, Chitnis CE (2002) Antibodies raised against receptor-binding domain of Plasmodium knowlesi Duffy binding protein inhibit erythrocyte invasion. Mol Biochem Parasitol 121: 21-31.

Smith, D. R., J. B. Pendry, and M. C. Wiltshire. 2004. Metamaterials and negative refractive index. Science 305:788-92.

Tsuboi, T., S. H. Kappe, F. al-Yaman, M. D. Prickett, M. Alpers, and J. H. Adams. 1994. Natural variation within the principal adhesion domain of the Plasmodium vivax duffy binding protein. Infect Immun 62:5581-6.

Udomsangpetch, R., O. Kaneko, K. Chotivanich, and J. Sattabongkot. 2008. Cultivation of Plasmodium vivax. Trends Parasitol 24:85-8.

VanBuskirk, K. M., E. Sevova, and J. H. Adams. 2004. Conserved residues in the Plasmodium vivax Duffy-binding protein ligand domain are critical for erythrocyte receptor recognition. Proc Natl Acad Sci U S A 101:15754-9.

Wertheimer SP, Barnwell JW (1989) Plasmodium vivax interaction with the human Duffy blood group glycoprotein: identification of a parasite receptor-like protein. Exp Parasitol 69: 340-350.

Wilson, N. J. and Cox, I.A. Structural Basis of Immune Recognition of Influenza Virus Hemagglutinin. Annu Rev Immunol 8, 737 (1990). (uploaded in 2 parts).

Xainli J., J. H. Adams, C. L. King. The erythrocyte binding motif of Plasmodium vivax Duffy binding protein is highly polymorphic and functionally conserved in isolates from Papua New Guinea. Mol Biochem Parasitol 111, 253 (Dec. 2000).

Xainli J, Baisor M, Kastens W, Bockarie M, Adams JH, et al. (2002) Age-dependent cellular immune responses to Plasmodium vivax Duffy binding protein in humans. J Immunol 169: 3200-3207.

Xainli J, Cole-Tobian JL, Baisor M, Kastens W, Bockarie M, et al. (2003) Epitope-specific humoral immunity to Plasmodium vivax Duffy binding protein. Infect Immun 71: 2508-2515.

Yazdani, S. S., A. R. Shakri, and C. E. Chitnis. 2004. A high cell density fermentation strategy to produce recombinant malarial antigen in E. coli. Biotechnol Lett 26:1891-5.

Houghten et al. Relative Importance of Position and individual Amino Acid residues in Peptide Antigen-Antibody Interactions: Implications in the Mechanism of Antigenic Drift and Antigenic Shift. Vaccines 1986; edited by Fred Brown, Cold Spring Harbor Laboratory.

```
DBPII-Sal1 (SEQ ID NO.: 1)    NHAFLQNTVMKNCNYKRKRRERDWDCNTKKDVCIPDRRYQLCMKELTNLVNNTDTNFHRD
DEKnull    (SEQ ID NO.: 2)    NHAFLQNTVMKNCNYKRKRRERDWDCNTKKDVCIPDRRYQLCMKELTNLVNNTDTNFHRD
                                                                                         *

DBPII-Sal1 (SEQ ID NO.: 1)    ITFRKLYLKRKLIYDAAVEGDLLLKLNNYRYNKDFCKDIRWSLGDFGDIIMGTDMEGIGY
DEKnull    (SEQ ID NO.: 2)    ITFRKLYLKRKLIYDAAVEGDLLLKLNNYRYNKDFCKDIRWSLGDFGDIIMGTDMEGIGY
                                       *                                        *

DBPII-Sal1 (SEQ ID NO.: 1)    SKVVENNLRSIFGTDEKAQQRRKQWWNESKAQIWTAMMYSVKKRLKGNFIWICKLNVAVN
DEKnull    (SEQ ID NO.: 2)    SKVVENNLRSIFGTASTAATSRTSWWNESKAQIWTAMMYSVKKRLKGNFIWICKLNVAVN
                                           ****  *   *                        *

DBPII-Sal1 (SEQ ID NO.: 1)    IEPQIYRWIREWGRDYVSELPTEVQKLKEKCDGKINYTDKKVCKVPPCQNACKSYDQWIT
DEKnull    (SEQ ID NO.: 2)    IEPQIYRWIREWGRDYVSELPTEVQKLKEKCDGKINYTDKKVCKVPPCQNACKSYDQWIT
                                        *                        *

DBPII-Sal1 (SEQ ID NO.: 1)    RKKNQWDVLSNKFISVKNAEKVQTAGIVTPYDILKQELDEFNEVAFENEINKRDGAYIEL
DEKnull    (SEQ ID NO.: 2)    RKKNQWDVLSNKFISVKNAEKVQTAGIVTPYDILKQELDEFNEVAFENEINKRDGAYIEL
                                                                        *
```

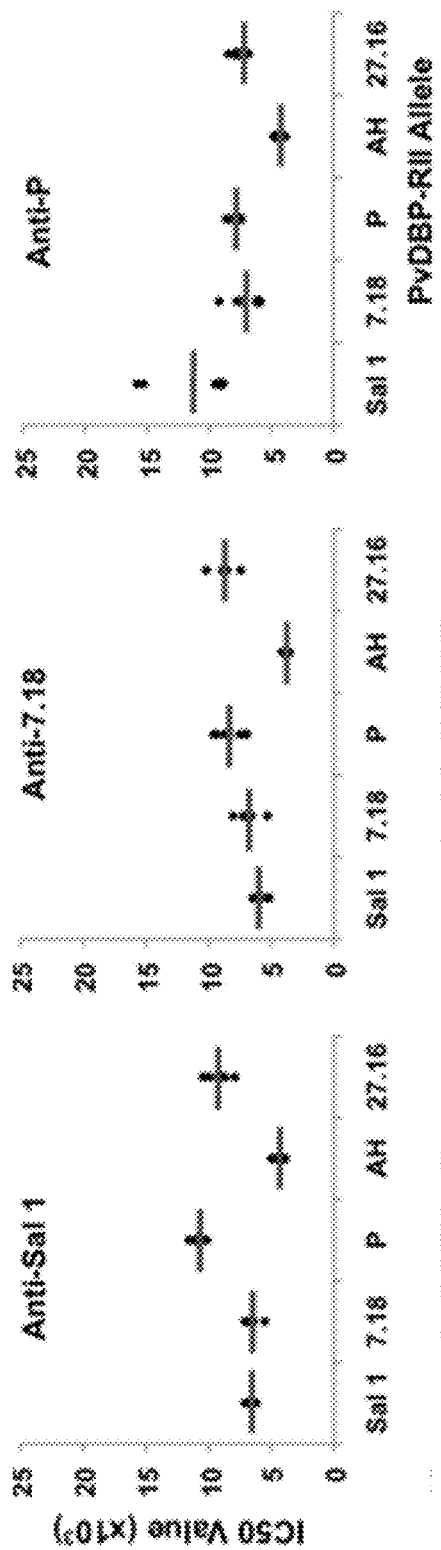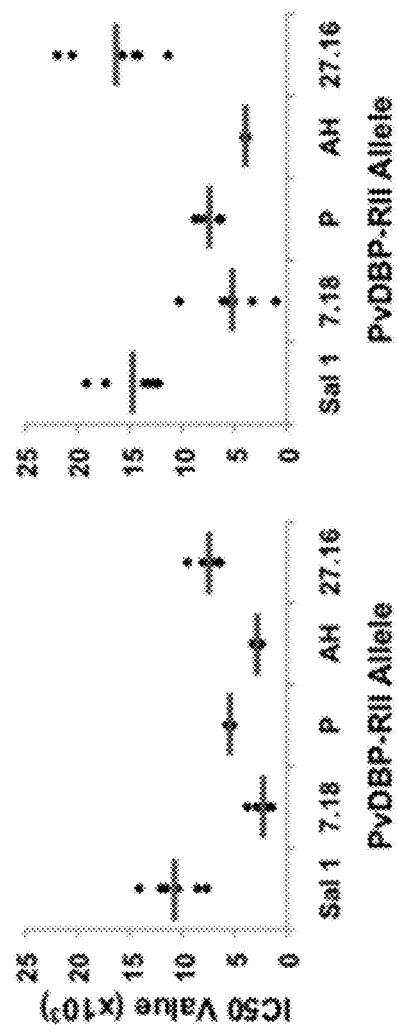
Fig. 14A Fig. 14B Fig. 14C Fig. 14D Fig. 14E

1 =WT undigested; 2 = WT digested
3-10 =- Mutant clones; 11 = undigested mutant clone 1 =WT undigested; 2 = WT digested
3-10 =- Mutant clones; 11 = undigested mutant clone

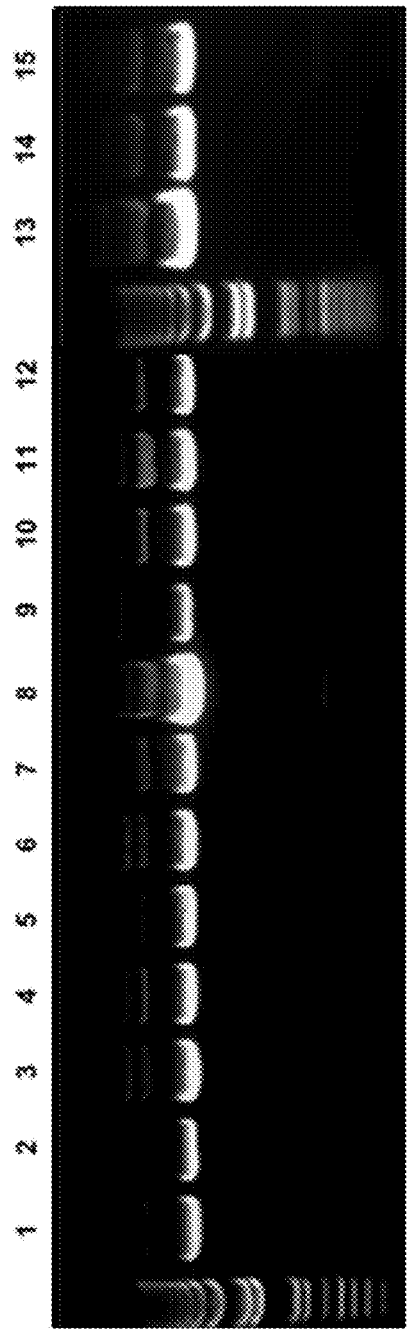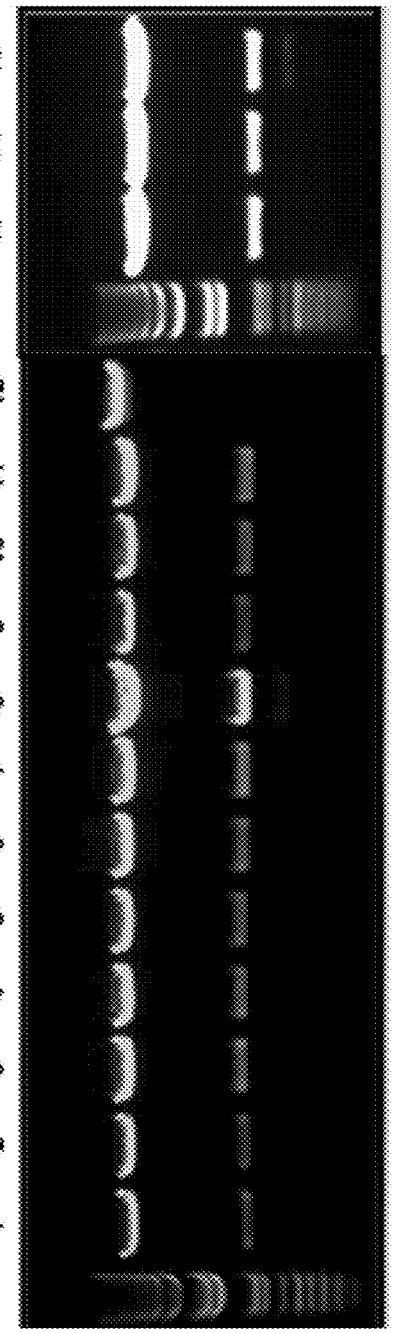

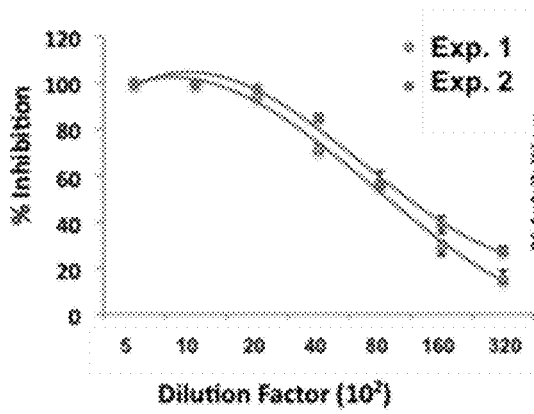
Fig. 31A
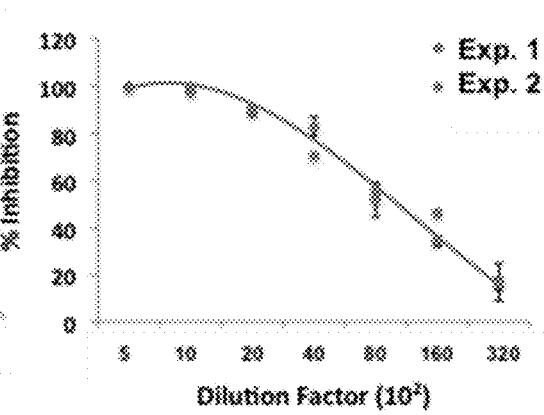
Fig. 31D
B) Anti-P vs. DBP-RII 27.16
E) Anti-DEKnull vs. DBP-RII 27.1
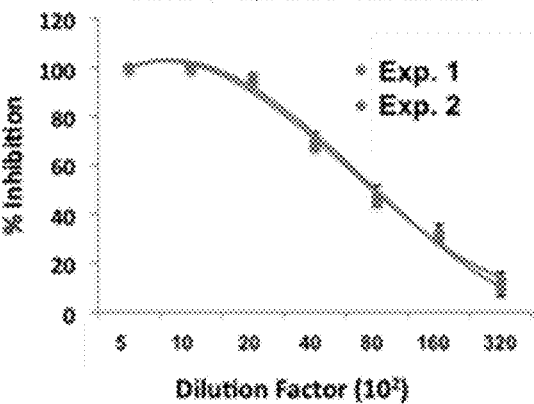
Fig. 31B
Fig. 31E
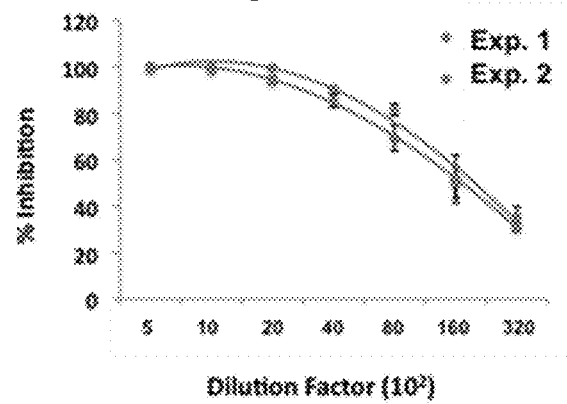
Fig. 31C B) Anti-P vs. DBP-RII 7.18

E) Anti-DEKnull vs. DBP-RII 7.18

B) Anti-P vs. DBP-RII P

E) Anti-DEKnull vs. DBP-RII P

C) Anti-Sal I/7.18/P vs. DBP-RII P

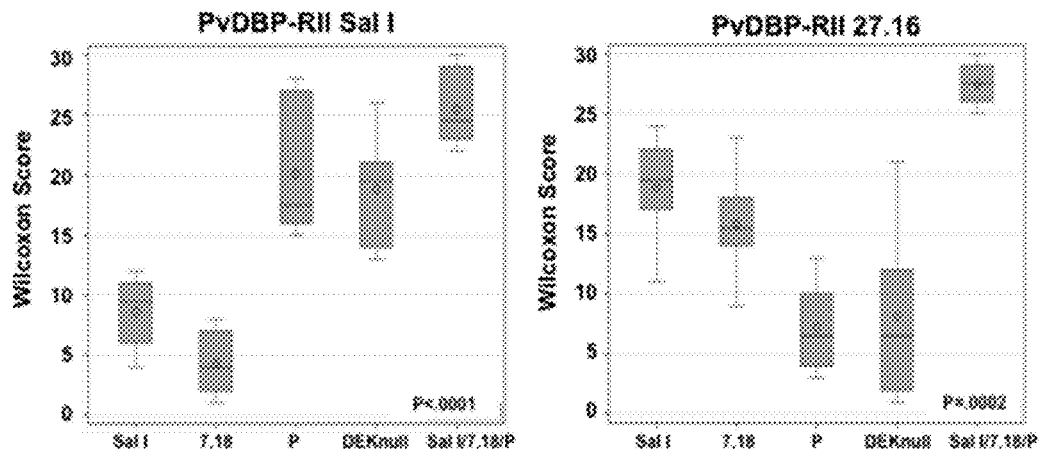
Fig. 40A
Fig. 40D
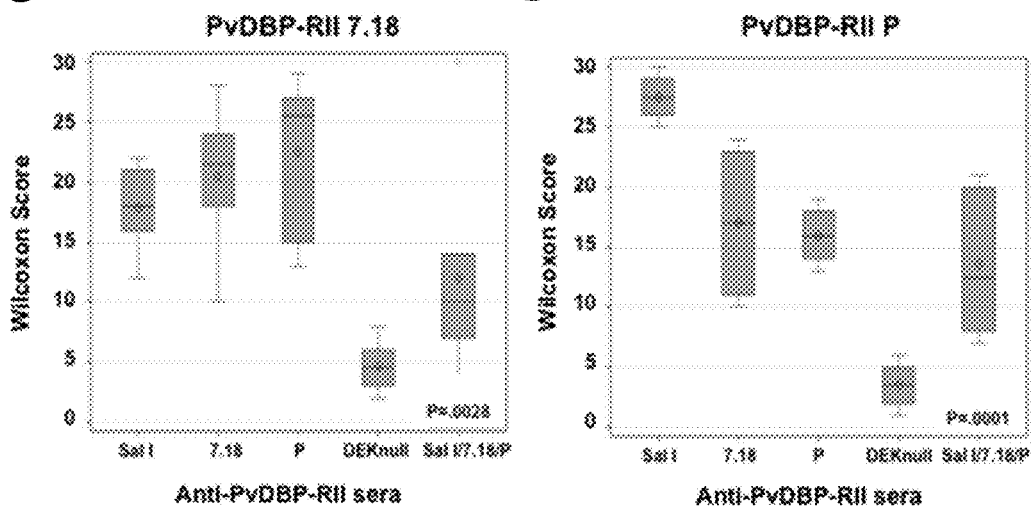
Fig. 40B
Fig. 40E
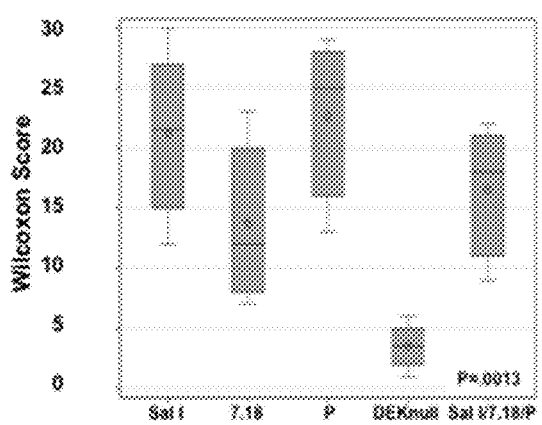
Fig. 40C

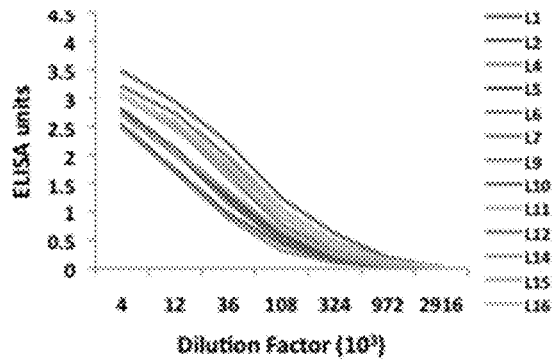
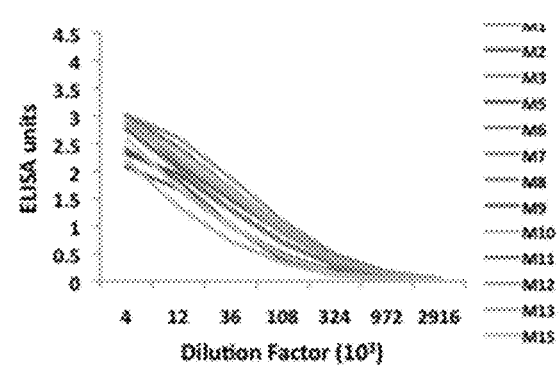
Fig. 42A    Fig. 42B
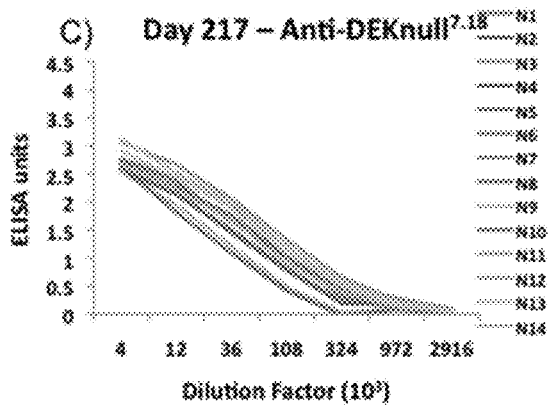
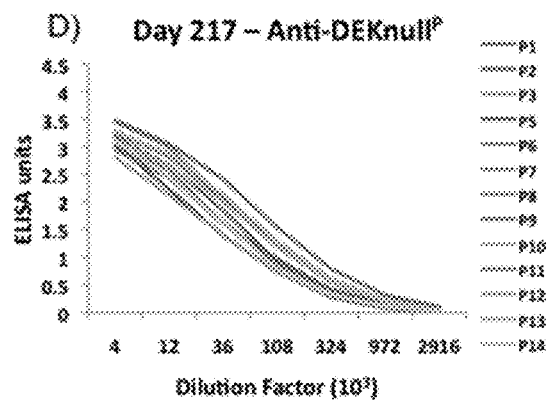
Fig. 42C    Fig. 42D
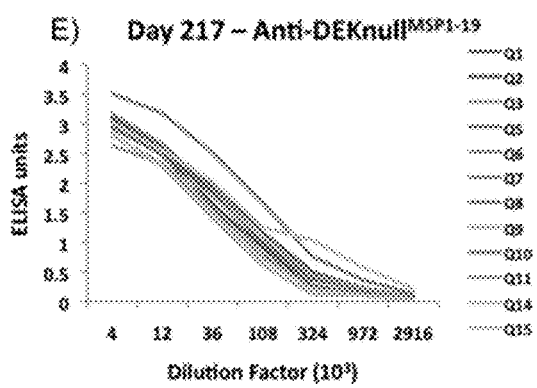
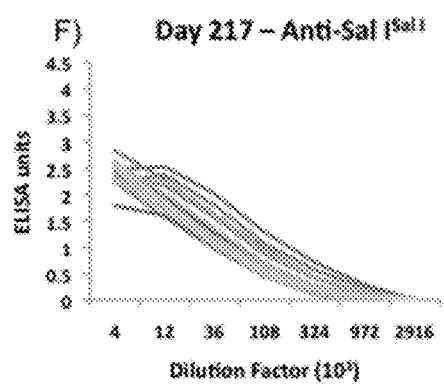
Fig. 42E    Fig. 42F

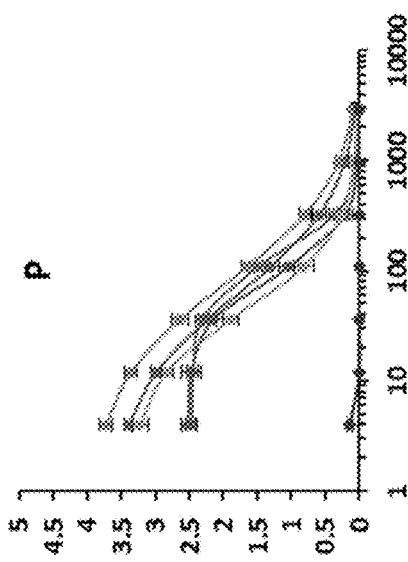
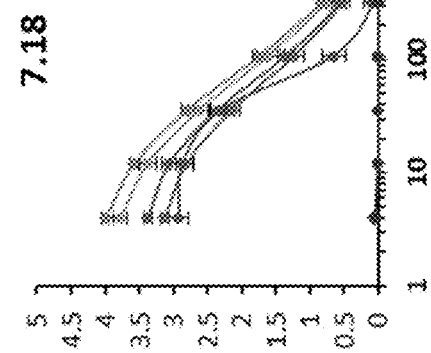
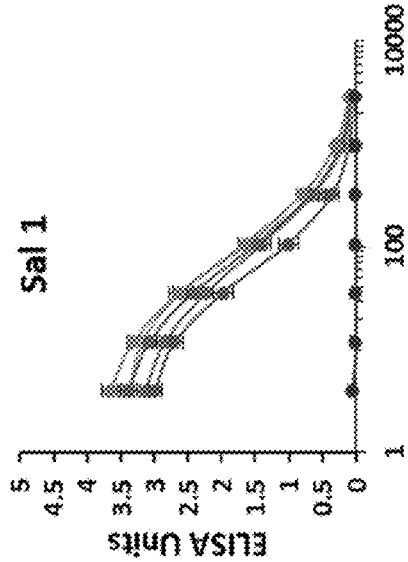
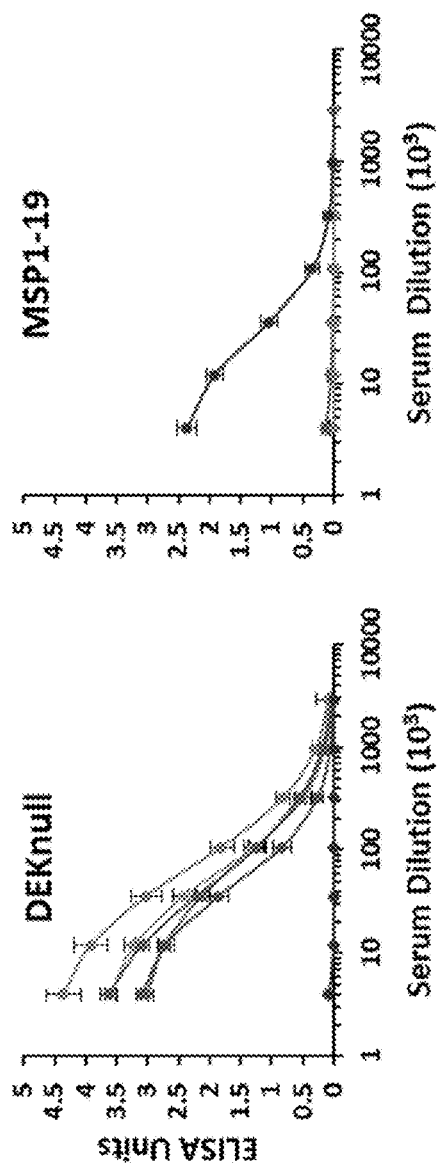
Fig. 50A Fig. 50B Fig. 50C Fig. 50D Fig. 50E

SEQUENCE LISTING

```
<160> NUMBER OF SEQ ID NOS: 9

<210> SEQ ID NO 1
<211> LENGTH: 300
<212> TYPE: PRT
<213> ORGANISM: Artificial sequence
```

<220> FEATURE:
<223> OTHER INFORMATION: Plasmodium vivax Duffy Binding Protein II
      ligand binding region Sal1 variant

<400> SEQUENCE: 1

```
Asn His Ala Phe Leu Gln Asn Thr Val Met Lys Asn Cys Asn Tyr Lys
1               5                   10                  15

Arg Lys Arg Arg Glu Arg Asp Trp Asp Cys Asn Thr Lys Lys Asp Val
            20                  25                  30

Cys Ile Pro Asp Arg Arg Tyr Gln Leu Cys Met Lys Glu Leu Thr Asn
        35                  40                  45

Leu Val Asn Asn Thr Asp Thr Asn Phe His Arg Asp Ile Thr Phe Arg
    50                  55                  60

Lys Leu Tyr Leu Lys Arg Lys Leu Ile Tyr Asp Ala Ala Val Glu Gly
65                  70                  75                  80

Asp Leu Leu Lys Leu Asn Asn Tyr Arg Tyr Asn Lys Asp Phe Cys
                85                  90                  95

Lys Asp Ile Arg Trp Ser Leu Gly Asp Phe Gly Asp Ile Ile Met Gly
            100                 105                 110

Thr Asp Met Glu Gly Ile Gly Tyr Ser Lys Val Val Glu Asn Asn Leu
        115                 120                 125

Arg Ser Ile Phe Gly Thr Asp Glu Lys Ala Gln Gln Arg Arg Lys Gln
    130                 135                 140

Trp Trp Asn Glu Ser Lys Ala Gln Ile Trp Thr Ala Met Met Tyr Ser
145                 150                 155                 160

Val Lys Lys Arg Leu Lys Gly Asn Phe Ile Trp Ile Cys Lys Leu Asn
                165                 170                 175

Val Ala Val Asn Ile Glu Pro Gln Ile Tyr Arg Trp Ile Arg Glu Trp
            180                 185                 190

Gly Arg Asp Tyr Val Ser Glu Leu Pro Thr Glu Val Gln Lys Leu Lys
        195                 200                 205

Glu Lys Cys Asp Gly Lys Ile Asn Tyr Thr Asp Lys Lys Val Cys Lys
    210                 215                 220

Val Pro Pro Cys Gln Asn Ala Cys Lys Ser Tyr Asp Gln Trp Ile Thr
225                 230                 235                 240

Arg Lys Lys Asn Gln Trp Asp Val Leu Ser Asn Lys Phe Ile Ser Val
                245                 250                 255

Lys Asn Ala Glu Lys Val Gln Thr Ala Gly Ile Val Thr Pro Tyr Asp
            260                 265                 270

Ile Leu Lys Gln Glu Leu Asp Glu Phe Asn Glu Val Ala Phe Glu Asn
        275                 280                 285

Glu Ile Asn Lys Arg Asp Gly Ala Tyr Ile Glu Leu
    290                 295                 300
```

<210> SEQ ID NO 2
<211> LENGTH: 300
<212> TYPE: PRT
<213> ORGANISM: Artificial sequence
<220> FEATURE:
<223> OTHER INFORMATION: Plasmodium vivax Duffy Binding Protein II
      ligand binding region DEKnull variant

<400> SEQUENCE: 2

```
Asn His Ala Phe Leu Gln Asn Thr Val Met Lys Asn Cys Asn Tyr Lys
1               5                   10                  15

Arg Lys Arg Arg Glu Arg Asp Trp Asp Cys Asn Thr Lys Lys Asp Val
            20                  25                  30
```

```
Cys Ile Pro Asp Arg Arg Tyr Gln Leu Cys Met Lys Glu Leu Thr Asn
         35                  40                  45

Leu Val Asn Asn Thr Asp Thr Asn Phe His Arg Asp Ile Thr Phe Arg
 50                  55                  60

Lys Leu Tyr Leu Lys Arg Lys Leu Ile Tyr Asp Ala Ala Val Glu Gly
 65                  70                  75                  80

Asp Leu Leu Lys Leu Asn Asn Tyr Arg Tyr Asn Lys Asp Phe Cys
                 85                  90                  95

Lys Asp Ile Arg Trp Ser Leu Gly Asp Phe Gly Asp Ile Ile Met Gly
                100                 105                 110

Thr Asp Met Glu Gly Ile Gly Tyr Ser Lys Val Val Glu Asn Asn Leu
             115                 120                 125

Arg Ser Ile Phe Gly Thr Ala Ser Thr Ala Thr Ser Arg Thr Ser
 130                 135                 140

Trp Trp Asn Glu Ser Lys Ala Gln Ile Trp Thr Ala Met Met Tyr Ser
145                 150                 155                 160

Val Lys Lys Arg Leu Lys Gly Asn Phe Ile Trp Ile Cys Lys Leu Asn
                 165                 170                 175

Val Ala Val Asn Ile Glu Pro Gln Ile Tyr Arg Trp Ile Arg Glu Trp
             180                 185                 190

Gly Arg Asp Tyr Val Ser Glu Leu Pro Thr Glu Val Gln Lys Leu Lys
                 195                 200                 205

Glu Lys Cys Asp Gly Lys Ile Asn Tyr Thr Asp Lys Lys Val Cys Lys
         210                 215                 220

Val Pro Pro Cys Gln Asn Ala Cys Lys Ser Tyr Asp Gln Trp Ile Thr
225                 230                 235                 240

Arg Lys Lys Asn Gln Trp Asp Val Leu Ser Asn Lys Phe Ile Ser Val
                 245                 250                 255

Lys Asn Ala Glu Lys Val Gln Thr Ala Gly Ile Val Thr Pro Tyr Asp
             260                 265                 270

Ile Leu Lys Gln Glu Leu Asp Glu Phe Asn Glu Val Ala Phe Glu Asn
         275                 280                 285

Glu Ile Asn Lys Arg Asp Gly Ala Tyr Ile Glu Leu
         290                 295                 300

<210> SEQ ID NO 3
<211> LENGTH: 16
<212> TYPE: PRT
<213> ORGANISM: Artificial sequence
<220> FEATURE:
<223> OTHER INFORMATION: Dominant immunogenic polymorphic B cell
      epitopic region of native Plasmodium vivax Duffy Binding Protein
      II

<400> SEQUENCE: 3

Asp Glu Lys Ala Gln Gln Arg Arg Lys Gln Trp Trp Asn Glu Ser Lys
1               5                   10                  15

<210> SEQ ID NO 4
<211> LENGTH: 10
<212> TYPE: PRT
<213> ORGANISM: Artificial sequence
<220> FEATURE:
<223> OTHER INFORMATION: Modified Dominant immunogenic polymorphic B
      cell epitopic region of Plasmodium vivax Duffy binding Protein
      II

<400> SEQUENCE: 4
```

-continued

```
Ala Ser Thr Ala Ala Thr Ser Arg Thr Ser
1               5                   10

<210> SEQ ID NO 5
<211> LENGTH: 1070
<212> TYPE: PRT
<213> ORGANISM: Plasmodium vivax

<400> SEQUENCE: 5

Met Lys Gly Lys Asn Arg Ser Leu Phe Val Leu Leu Val Leu Leu Leu
1               5                   10                  15

Leu His Lys Val Asn Asn Val Leu Leu Glu Arg Thr Ile Glu Thr Leu
            20                  25                  30

Leu Glu Cys Lys Asn Glu Tyr Val Lys Gly Glu Asn Gly Tyr Lys Leu
        35                  40                  45

Ala Lys Gly His His Cys Val Glu Glu Asp Asn Leu Glu Arg Trp Leu
    50                  55                  60

Gln Gly Thr Asn Glu Arg Arg Ser Glu Asn Ile Lys Tyr Lys Tyr
65                  70                  75                  80

Gly Val Thr Glu Leu Lys Ile Lys Tyr Ala Gln Met Asn Gly Lys Arg
                85                  90                  95

Ser Ser Arg Ile Leu Lys Glu Ser Ile Tyr Gly Ala His Asn Phe Gly
            100                 105                 110

Gly Asn Ser Tyr Met Glu Gly Lys Asp Gly Gly Asp Lys Thr Gly Glu
        115                 120                 125

Glu Lys Asp Gly Glu His Lys Thr Asp Ser Lys Thr Asp Asn Gly Lys
    130                 135                 140

Gly Ala Asn Asn Leu Val Met Leu Asp Tyr Glu Thr Ser Ser Asn Gly
145                 150                 155                 160

Gln Pro Ala Gly Thr Leu Asp Asn Val Leu Glu Phe Val Thr Gly His
                165                 170                 175

Glu Gly Asn Ser Arg Lys Asn Ser Ser Asn Gly Gly Asn Pro Tyr Asp
            180                 185                 190

Ile Asp His Lys Lys Thr Ile Ser Ser Ala Ile Ile Asn His Ala Phe
        195                 200                 205

Leu Gln Asn Thr Val Met Lys Asn Cys Asn Tyr Lys Arg Lys Arg
    210                 215                 220

Glu Arg Asp Trp Asp Cys Asn Thr Lys Lys Asp Val Cys Ile Pro Asp
225                 230                 235                 240

Arg Arg Tyr Gln Leu Cys Met Lys Glu Leu Thr Asn Leu Val Asn Asn
                245                 250                 255

Thr Asp Thr Asn Phe His Arg Asp Ile Thr Phe Arg Lys Leu Tyr Leu
            260                 265                 270

Lys Arg Lys Leu Ile Tyr Asp Ala Ala Val Glu Gly Asp Leu Leu
    275                 280                 285

Lys Leu Asn Asn Tyr Arg Tyr Asn Lys Asp Phe Cys Lys Asp Ile Arg
290                 295                 300

Trp Ser Leu Gly Asp Phe Gly Asp Ile Ile Met Gly Thr Asp Met Glu
305                 310                 315                 320

Gly Ile Gly Tyr Ser Lys Val Val Glu Asn Asn Leu Arg Ser Ile Phe
                325                 330                 335

Gly Thr Asp Glu Lys Ala Gln Gln Arg Arg Lys Gln Trp Trp Asn Glu
            340                 345                 350

Ser Lys Ala Gln Ile Trp Thr Ala Met Met Tyr Ser Val Lys Lys Arg
        355                 360                 365
```

```
Leu Lys Gly Asn Phe Ile Trp Ile Cys Lys Leu Asn Val Ala Val Asn
    370             375                 380

Ile Glu Pro Gln Ile Tyr Arg Trp Ile Arg Glu Trp Gly Arg Asp Tyr
385             390                 395                 400

Val Ser Glu Leu Pro Thr Glu Val Gln Lys Leu Lys Glu Lys Cys Asp
                405                 410                 415

Gly Lys Ile Asn Tyr Thr Asp Lys Val Cys Lys Val Pro Pro Cys
            420                 425                 430

Gln Asn Ala Cys Lys Ser Tyr Asp Gln Trp Ile Thr Arg Lys Lys Asn
            435                 440                 445

Gln Trp Asp Val Leu Ser Asn Lys Phe Ile Ser Val Lys Asn Ala Glu
    450                 455                 460

Lys Val Gln Thr Ala Gly Ile Val Thr Pro Tyr Asp Ile Leu Lys Gln
465             470                 475                 480

Glu Leu Asp Glu Phe Asn Glu Val Ala Phe Glu Asn Glu Ile Asn Lys
                485                 490                 495

Arg Asp Gly Ala Tyr Ile Glu Leu Cys Val Cys Ser Val Glu Glu Ala
            500                 505                 510

Lys Lys Asn Thr Gln Glu Val Val Thr Asn Val Asp Asn Ala Ala Lys
    515                 520                 525

Ser Gln Ala Thr Asn Ser Asn Pro Ile Ser Gln Pro Val Asp Ser Ser
    530                 535                 540

Lys Ala Glu Lys Val Pro Gly Asp Ser Thr His Gly Asn Val Asn Ser
545             550                 555                 560

Gly Gln Asp Ser Ser Thr Thr Gly Lys Ala Val Thr Gly Asp Gly Gln
                565                 570                 575

Asn Gly Asn Gln Thr Pro Ala Glu Ser Asp Val Gln Arg Ser Asp Ile
            580                 585                 590

Ala Glu Ser Val Ser Ala Lys Asn Val Asp Pro Gln Lys Ser Val Ser
    595                 600                 605

Lys Arg Ser Asp Asp Thr Ala Ser Val Thr Gly Ile Ala Glu Ala Gly
610             615                 620

Lys Glu Asn Leu Gly Ala Ser Asn Ser Arg Pro Ser Glu Ser Thr Val
625             630                 635                 640

Glu Ala Asn Ser Pro Gly Asp Asp Thr Val Asn Ser Ala Ser Ile Pro
                645                 650                 655

Val Val Ser Gly Glu Asn Pro Leu Val Thr Pro Tyr Asn Gly Leu Arg
            660                 665                 670

His Ser Lys Asp Asn Ser Asp Ser Asp Gly Pro Ala Glu Ser Met Ala
    675                 680                 685

Asn Pro Asp Ser Asn Ser Lys Gly Glu Thr Gly Lys Gly Gln Asp Asn
    690                 695                 700

Asp Met Ala Lys Ala Thr Lys Asp Ser Ser Asn Ser Ser Asp Gly Thr
705             710                 715                 720

Ser Ser Ala Thr Gly Asp Thr Thr Asp Ala Val Asp Arg Glu Ile Asn
                725                 730                 735

Lys Gly Val Pro Glu Asp Arg Asp Lys Thr Val Gly Ser Lys Asp Gly
            740                 745                 750

Gly Gly Glu Asp Asn Ser Ala Asn Lys Asp Ala Ala Thr Val Val Gly
        755                 760                 765

Glu Asp Arg Ile Arg Glu Asn Ser Ala Gly Gly Ser Thr Asn Asp Arg
    770                 775                 780
```

-continued

```
Ser Lys Asn Asp Thr Glu Lys Asn Gly Ala Ser Thr Pro Asp Ser Lys
785                 790                 795                 800

Gln Ser Glu Asp Ala Thr Ala Leu Ser Lys Thr Glu Ser Leu Glu Ser
            805                 810                 815

Thr Glu Ser Gly Asp Arg Thr Thr Asn Asp Thr Thr Asn Ser Leu Glu
            820                 825                 830

Asn Lys Asn Gly Gly Lys Glu Lys Asp Leu Gln Lys His Asp Phe Lys
            835                 840                 845

Ser Asn Asp Thr Pro Asn Glu Pro Asn Ser Asp Gln Thr Thr Asp
    850                 855                 860

Ala Glu Gly His Asp Arg Asp Ser Ile Lys Asn Asp Lys Ala Glu Arg
865                 870                 875                 880

Arg Lys His Met Asn Lys Asp Thr Phe Thr Lys Asn Thr Asn Ser His
            885                 890                 895

His Leu Asn Ser Asn Asn Asn Leu Ser Asn Gly Lys Leu Asp Ile Lys
            900                 905                 910

Glu Tyr Lys Tyr Arg Asp Val Lys Ala Thr Arg Glu Asp Ile Ile Leu
            915                 920                 925

Met Ser Ser Val Arg Lys Cys Asn Asn Asn Ile Ser Leu Glu Tyr Cys
930                 935                 940

Asn Ser Val Glu Asp Lys Ile Ser Ser Asn Thr Cys Ser Arg Glu Lys
945                 950                 955                 960

Ser Lys Asn Leu Cys Cys Ser Ile Ser Asp Phe Cys Leu Asn Tyr Phe
            965                 970                 975

Asp Val Tyr Ser Tyr Glu Tyr Leu Ser Cys Met Lys Lys Glu Phe Glu
            980                 985                 990

Asp Pro Ser Tyr Lys Cys Phe Thr  Lys Gly Gly Phe Lys  Asp Lys Thr
            995                 1000                1005

Tyr Phe  Ala Ala Ala Gly Ala  Leu Leu Ile Leu Leu  Leu Leu Ile
    1010                 1015                 1020

Ala Ser  Arg Lys Met Ile Lys  Asn Asp Ser Glu Glu  Ala Thr Phe
    1025                 1030                 1035

Asn Glu  Phe Glu Glu Tyr Cys  Asp Asn Ile His Arg  Ile Pro Leu
    1040                 1045                 1050

Met Pro  Asn Asn Ile Glu His  Met Gln Pro Ser Thr  Pro Leu Asp
    1055                 1060                 1065

Tyr Ser
    1070

<210> SEQ ID NO 6
<211> LENGTH: 237
<212> TYPE: PRT
<213> ORGANISM: Artificial sequence
<220> FEATURE:
<223> OTHER INFORMATION: Plasmodium vivax Duffy Binding Protein II
      ligand binding region 7.18 variant

<400> SEQUENCE: 6

Asp Arg Arg Tyr Gln Leu Cys Met Lys Glu Leu Thr Asn Leu Val Asn
1               5                   10                  15

Asn Thr Asp Thr Asn Phe His Ser Asp Ile Thr Phe Arg Lys Leu Tyr
            20                  25                  30

Leu Lys Arg Lys Leu Ile Tyr Asp Ala Ala Val Glu Gly Asp Leu Leu
        35                  40                  45

Leu Lys Leu Asn Asn Tyr Arg Tyr Asn Lys Asp Phe Cys Lys Asp Ile
    50                  55                  60
```

-continued

```
Arg Trp Ser Leu Gly Asp Phe Gly Asp Ile Ile Met Gly Thr Asp Met
 65                  70                  75                  80

Glu Gly Ile Gly Tyr Ser Lys Val Val Glu Asn Asn Leu Arg Ser Ile
                 85                  90                  95

Phe Gly Thr Gly Glu Gln Ala Gln Gln Arg Arg Lys Gln Trp Trp Asn
            100                 105                 110

Glu Ser Lys Ala Gln Ile Trp Thr Ala Met Met Tyr Ser Val Lys Lys
        115                 120                 125

Arg Leu Lys Gly Lys Phe Ile Trp Ile Cys Lys Ile Asn Val Ala Val
    130                 135                 140

Asn Ile Glu Pro Gln Ile Tyr Arg Arg Ile Arg Glu Trp Gly Arg Asp
145                 150                 155                 160

Tyr Val Ser Glu Leu Pro Thr Glu Val Gln Lys Leu Lys Glu Lys Cys
                165                 170                 175

Asp Gly Lys Ile Asn Tyr Thr Asp Lys Lys Val Cys Lys Val Pro Pro
            180                 185                 190

Cys Gln Asn Ala Cys Lys Ser Tyr Asp Gln Trp Ile Thr Arg Lys Lys
        195                 200                 205

Asn Gln Trp Asp Val Leu Ser Asn Lys Phe Lys Ser Val Lys Asn Ala
    210                 215                 220

Glu Lys Val Gln Thr Ala Gly Ile Val Thr Pro Tyr Asp
225                 230                 235
```

<210> SEQ ID NO 7
<211> LENGTH: 237
<212> TYPE: PRT
<213> ORGANISM: Artificial sequence
<220> FEATURE:
<223> OTHER INFORMATION: Plasmodium vivax Duffy Binding Protein II
      ligand binding region P variant

<400> SEQUENCE: 7

```
Asp Arg Arg Tyr Gln Leu Cys Met Lys Glu Leu Thr Asn Leu Val Asn
  1               5                  10                  15

Asn Thr Asp Thr Asn Phe His Ser Asp Ile Thr Phe Arg Lys Leu Tyr
                 20                  25                  30

Leu Lys Arg Lys Leu Ile Tyr Asp Ala Ala Val Glu Gly Asp Leu Leu
            35                  40                  45

Phe Lys Leu Asn Asn Tyr Arg Tyr Asn Lys Asp Phe Cys Lys Asp Ile
        50                  55                  60

Arg Trp Ser Leu Gly Asp Phe Gly Asp Ile Ile Met Gly Thr Asp Met
 65                  70                  75                  80

Glu Gly Ile Gly Tyr Ser Lys Val Val Glu Asp Asn Leu Arg Ser Ile
                 85                  90                  95

Phe Gly Thr Gly Lys Asn Ala Gln Gln His Arg Lys Gln Trp Trp Asn
            100                 105                 110

Glu Ser Lys Ala Gln Ile Trp Thr Ala Met Met Tyr Ser Val Lys Lys
        115                 120                 125

Arg Leu Lys Gly Lys Phe Ile Trp Ile Cys Lys Ile Asn Val Ala Val
    130                 135                 140

Asn Ile Glu Pro Gln Ile Tyr Arg Arg Ile Arg Glu Trp Gly Arg Asp
145                 150                 155                 160

Tyr Val Ser Glu Leu Pro Thr Glu Val Gln Lys Leu Lys Glu Lys Cys
                165                 170                 175

Asp Gly Lys Ile Asn Tyr Thr Asp Lys Lys Val Cys Lys Val Pro Pro
```

```
              180                 185                 190
Cys Gln Asn Ala Cys Lys Ser Tyr Asp Gln Trp Ile Thr Arg Lys Lys
            195                 200                 205

Asn Gln Trp Asp Val Leu Ser Asn Lys Phe Lys Ser Val Lys Asn Ala
        210                 215                 220

Glu Lys Val Gln Thr Ala Gly Ile Val Thr Pro Tyr Asp
225                 230                 235

<210> SEQ ID NO 8
<211> LENGTH: 237
<212> TYPE: PRT
<213> ORGANISM: Artificial sequence
<220> FEATURE:
<223> OTHER INFORMATION: Plasmodium vivax Duffy Binding Protein II
      ligand binding region 27-16 variant

<400> SEQUENCE: 8

Asp Arg Arg Tyr Gln Leu Cys Met Lys Glu Leu Thr Asn Leu Val Asn
1               5                   10                  15

Asn Thr Asp Thr Asn Phe His Ser Asp Ile Thr Phe Arg Lys Leu Tyr
            20                  25                  30

Leu Lys Arg Lys Leu Ile Tyr Asp Ala Ala Val Glu Gly Asp Leu Leu
        35                  40                  45

Leu Lys Leu Asn Asn Tyr Arg Tyr Asn Lys Asp Phe Cys Lys Asp Ile
    50                  55                  60

Arg Trp Ser Leu Gly Asp Phe Gly Asp Ile Ile Met Gly Thr Asp Met
65                  70                  75                  80

Glu Gly Ile Gly Tyr Ser Lys Val Val Glu Asn Asn Leu Arg Ser Ile
                85                  90                  95

Phe Gly Thr Gly Glu Lys Ala Gln Gln His Arg Lys Gln Trp Trp Asn
            100                 105                 110

Glu Ser Lys Ala Gln Ile Trp Thr Ala Met Met Tyr Ser Val Lys Lys
        115                 120                 125

Arg Leu Lys Gly Asn Phe Ile Trp Ile Cys Lys Ile Asn Val Ala Val
    130                 135                 140

Asn Ile Glu Pro Gln Ile Tyr Arg Trp Ile Arg Glu Trp Gly Arg Asp
145                 150                 155                 160

Tyr Val Lys Glu Leu Pro Thr Glu Val Gln Lys Leu Lys Glu Lys Cys
                165                 170                 175

Asp Gly Lys Ile Asn Tyr Thr Asp Lys Lys Val Cys Lys Val Pro Pro
            180                 185                 190

Cys Gln Asn Ala Cys Lys Ser Tyr Asp Gln Trp Ile Thr Arg Lys Glu
        195                 200                 205

Asn Gln Trp Asp Val Leu Ser Asn Lys Phe Ile Ser Val Lys Asn Ala
    210                 215                 220

Glu Lys Val Gln Thr Ala Gly Ile Val Thr Pro Tyr Asp
225                 230                 235

<210> SEQ ID NO 9
<211> LENGTH: 237
<212> TYPE: PRT
<213> ORGANISM: Artificial sequence
<220> FEATURE:
<223> OTHER INFORMATION: Plasmodium vivax Duffy Binding Protein II
      ligand binding region AH variant

<400> SEQUENCE: 9

Asp Arg Arg Tyr Gln Leu Cys Met Lys Glu Leu Thr Asn Leu Val Asn
```

-continued

```
1               5                   10                  15
Asn Thr Asp Thr Asn Phe His Ser Asp Ile Thr Phe Arg Lys Leu Tyr
            20                  25                  30

Leu Lys Arg Lys Leu Ile Tyr Asp Ala Ala Val Glu Gly Asp Leu Leu
            35                  40                  45

Leu Lys Leu Asn Asn Tyr Arg Tyr Asn Lys Asp Phe Cys Lys Asp Ile
    50                  55                  60

Arg Trp Ser Leu Gly Asp Phe Gly Asp Ile Ile Met Gly Thr Asp Met
65                  70                  75                  80

Glu Gly Ile Gly Tyr Ser Glu Val Val Glu Asn Asn Leu Arg Ser Ile
                85                  90                  95

Phe Gly Thr Gly Glu Gln Ala Gln Gln Arg Arg Lys Gln Trp Trp Asn
                100                 105                 110

Glu Ser Lys Ala Gln Ile Trp Thr Ala Met Met Tyr Ser Val Lys Lys
            115                 120                 125

Arg Leu Lys Gly Lys Phe Ile Trp Ile Cys Lys Ile Asn Val Ala Val
            130                 135                 140

Asn Ile Glu Pro Gln Ile Tyr Arg Arg Ile Arg Glu Trp Gly Arg Asp
145                 150                 155                 160

Tyr Val Ser Glu Leu Pro Thr Glu Val Gln Lys Leu Lys Glu Lys Cys
                165                 170                 175

Asp Gly Lys Ile Asn Tyr Thr Asp Lys Lys Val Cys Lys Val Pro Pro
            180                 185                 190

Cys Gln Asn Ala Cys Lys Ser Tyr Asp Gln Trp Ile Thr Arg Lys Lys
            195                 200                 205

Asn Gln Trp Asp Val Leu Ser Asn Lys Phe Lys Ser Val Lys Asn Ala
    210                 215                 220

Glu Lys Val Gln Thr Ala Gly Ile Val Thr Pro Tyr Asp
225                 230                 235
```

SYNTHETIC ANTIGEN BASED ON THE LIGAND DOMAIN OF THE PLASMODIUM VIVAX DUFFY BINDING PROTEIN

CROSS-REFERENCE TO RELATED APPLICATION

This application is a Divisional of the U.S. patent application entitled "SYNTHETIC ANTIGEN BASED ON THE LIGAND DOMAIN OF THE *PLASMODIUM VIVAX* DUFFY BINDING PROTEIN", filed on Aug. 20, 2012 and assigned Ser. No. 13/589,253, now U.S. Pat. No. 8,784,832 which claimed the benefit of U.S. Provisional Patent Application No. 61/525,412 filed Aug. 19, 2011 entitled "DESIGN AND IMMUNOGENICITY OF A NOVEL SYNTHETIC ANTIGEN BASED ON THE LIGAND DOMAIN OF THE *PLASMODIUM VIVAX* DUFFY BINDING PROTEIN" the complete disclosures of which are incorporated herein by reference in their entireties.

STATEMENT REGARDING FEDERALLY SPONSORED RESEARCH OR DEVELOPMENT

This invention was made with government support under Grant No. R01 AI064478 awarded by the National Institutes of Health. The government has certain rights in the invention.

SEQUENCE LISTING

The present disclosure includes a sequence listing incorporated herein by reference in its entirety.

TECHNICAL FIELD

The present disclosure is generally related engineered variants of the *Plasmodium vivax* Duffy Binding Protein having reduced dominant immunogenic epitopes. The present disclosure further relates to methods of generating an immune response with enhanced specificity against multiple strains of *Plasmodium vivax*.

BACKGROUND

*Plasmodium vivax* is the most common cause of malaria outside of Africa and a serious economic and health burden in many developing countries (Mendis et al., (2001) *Am. J. Trop. Med. Hyg.* 64: 97-106). *Vivax* malaria is often a severe debilitating disease in adults as well as children with an impact and occurrence that is underreported (Price et al., (2007) *Am. J. Trop. Med. Hyg.* 77: 79-87; Mueller et al., (2009) *Lancet Infect. Dis.* 9: 555-566). Diagnosis is more difficult than for *P. falciparum* since the parasite selectively invades reticulocytes thereby leading to lower parasitemias and lower level transmission intensity, which in turn is believed to lead to development of weak protective immunity by intermittent exposure of individuals living in these endemic areas (Mendis et al., (2001) *Am. J. Trop. Med. Hyg.* 64: 97-106; Mueller et al., (2009) *Lancet Infect. Dis.* 9: 555-566; Chootong et al., (2010) *Infect. Immun.* 78: 1089-1095). The biology and mechanism of transmission therefore gives this parasite great resilience while increasing the need for new approaches for control and management of *P. vivax* infections.

There is enough evidence suggesting a blood-stage vaccine should be part of the overall strategy for malaria control (Arevalo-Herrera et al., (2010) *Hum. Vaccines* 6: 124-132). Similar to other species, morbidity caused by *P. vivax* is associated with the asexual blood-stage growth although severe clinical disease typically occurs at much lower parasitemias. Therefore, a vaccine based on these stages will help to reduce or eliminate clinical manifestations observed during *vivax* malaria. Merozoite proteins, which play a major role during the invasion process, are important candidates for vaccine development aimed at neutralizing blood-stage growth. Progress in the identification, characterization and development of these vaccine candidates, as well as all new prophylactic and therapeutic control measures against *vivax* malaria, have been seriously hindered by lack of a long-term *P. vivax* in vitro culture system (Udomsangpetch et al., (2008) *Trends Parasitol.* 24: 85-88). The Duffy binding protein (DBPII) is one of the few merozoite proteins that have been well characterized with a critical role in *P. vivax* blood-stage development.

Malaria parasites depend on specific receptor-ligand interactions for successful invasion of the host erythrocytes. In *P. vivax*, blood-stage development depends on DBPII interaction with the Duffy Antigen Receptor of Chemokines (DARC) on human erythrocytes for erythrocyte invasion, a process mediated by the PvDBPII and PkDBPII respectively (Miller et al., (1975) *Science* 189: 561-563; Barnwell et al., (1989) *J. Exp. Med.* 169: 1795-1802; Wertheimer & Barnwell (1989) *Exp. Parasitol.* 69: 340-350). It has been suggested that this molecule plays an important role during the process of junction formation just before invasion (Adams et al., (1990) *Cell* 63: 141-153). Individuals lacking DARC on their erythrocyte have been shown to be refractory to *P. vivax* infection (Miller et al., (1976) New Eng.l J. Med. 295: 302-304). This dependence of *P. vivax* on DBPP for invasion makes DBPII a prime target for vaccine development against *vivax* malaria. PvDBPII is a member of the erythrocyte binding proteins (EBPs) family, characterized by highly conserved cysteine-rich domains known as the region II (Adams et al., (1992) *Proc. Natl. Acad. Sci. U.S.A.* 89: 7085-7089; Chitnis & Miller (1994) J. Exp. Med. 180: 497-506; Sim et al., (1994) *Science* 264: 1941-1944). In PvDBPII, this region, (DBPII) also known as the ligand domain contains the residues critical for receptor recognition (VanBuskirk et al., (2004) *Proc. Natl. Acad. Sci. U.S.A.* 101: 15754-15759; Chitnis et al., (1996) *J. Exp. Med.* 184: 1531-1536; Ranjan & Chitnis (1999) *Proc. Natl. Acad. Sci. U.S.A.* 96: 14067-14072).

Individuals in endemic regions are known to develop anti-DBPII antibodies with significant quantitative and qualitative differences in their serological responses (Chootong et al., (2010) *Infect. Immun.* 78: 1089-1095; Fraser et al., (1997) *Infect. Immun.* 65: 2772-2777; Xainli et al. (2002) *J. Immunol.* 169: 3200-3207; Xainli et al., (2003) *Infect. Immun.* 71: 2508-2515; Cole-Tobian et al. (2002) *J. Infect. Dis.* 186: 531-539) and this response is known to increase with age as a result of boosting effect due to recurrent exposure (Grimberg et al., (2007) *PLoS Med* 4: e337; Michon et al., (2000) *Infect. Immun.* 68: 3164-3171; King et al., (2008) *Proc. Natl. Acad. Sci. U.S.A.* 105: 8363-8368). Naturally acquired antibodies to the *Plasmodium vivax* DBPII have been shown to inhibit binding of DBPII to DARC on human erythrocyte (Chootong et al., (2010) *Infect. Immun.* 78: 1089-1095; Grimberg et al., (2007) *PLoS Med* 4: e337; Michon et al., (2000) *Infect. Immun.* 68: 3164-3171; Dutta et al., (2000) *Mol. Biochem. Parasitol.* 109: 179-184). Furthermore, it has been demonstrated that antibodies raised against rDBPII and rPkDBPII which is a homolog of DBPII (greater than 70% identity) can inhibit erythrocyte invasion by both *P. vivax* (Michon et al., (2000) *Infect. Immun.* 68: 3164-3171) and *P. knowlesi* (Singh et al., (2002) *Mol. Biochem. Parasitol.* 121: 21-31) as well as block cytoadherence of DBPII to human erythrocytes (Yazdani et al., (2004) *Biotechnol. Lett.* 26: 1891-1895). These data gives further support for DBPII as a candidate for the development of a vaccine against *P. vivax* malaria. DBPII contains a large number of polymorphisms, thought to be exerted by host immune response, a mechanism suggested to be used by the parasite for immune evasion (Xainli et al. (2002) *J. Immunol.* 169: 3200-3207; Tsuboi et al. (1994) *Infect. Immun.* 62: 5581-5586; Cole-Tobian & King (2003) *Mol. Biochem. Parasitol.* 127: 121-132). These polymorphisms influence the immunogenicity of DBPII leading to strain-specific immunity in *P. vivax* (King et al. (2008) *Proc. Natl. Acad. Sci. U.S.A.* 105: 8363-8368; VanBuskirk et al. (2004) *J. Infect. Dis.* 190: 1556-1562; Ceravolo et al., (2009) *Clin. Exp. Immunol.* 156: 502-510).

*Plasmodium vivax* dependence on binding of the *P. vivax* Duffy-binding protein (PvDBPII) to the erythrocyte Duffy antigen receptor (Duffy antigen receptor for chemokines, DARC) for invasion into the cell, makes this interaction an attractive target for intervention (Adams et al., (1990) *Cell* 63: 141-153; Adams et al., (1992) *Proc. Natl. Acad. Sci. U.S.A.* 89: 7085-7089; Chitnis & Miller (1994) *J. Exp. Med.* 180: 497-506; Haynes et al., (1998) *J. Exp. Med.* 167:1873-1881; Miller et al., (1976) *New England J. Med.* 295: 302-304; Wertheimer & Barnwell (1989) *Exp. Parasitol.* 69: 340-350). The PvDBPII recognition site for the erythrocyte receptor has been mapped to an area between cysteines 4 and 7 of the DBL domain (Chitnis et al., (1996) *J. Exp. Med.* 184:1531; Ranjan & Chitnis (1999) *Proc. Natl. Acad. Sci. USA* 96:14067; VanBuskirk et al., (2004) *Proc. Natl. Acad. Sci. USA* 101:15754; Singh et al., (2003) *Biochem.* 374:193). This is the most highly polymorphic region of the open reading frame with a high rate of nonsynonymous to synonymous polymorphisms, suggesting positive selection indicative of immune pressure (Ampudia et al., (1996) *Mol Biochem Parasitol* 78:269; Cole-Tobian & King (2003) *Mol. Biochem. Parasitol.* 127:121; Cole-Tobian et al., (2002) *J. Infect. Dis.* 186:531; Kho et al., (2001) *Korean J. Parasitol.* 39:143; Tsuboi et al., (1994) *Infection and Immunity* 62:5581; Xainli et al., (2000) *Mol. Biochem. Parasitol.* 111:253). The non-homologous proteins Influenza hemagglutinin (HA) and *Plasmodium* apical membrane antigen 1 (AMA-1) reveal a pattern of polymorphisms located adjacent to and surrounding their receptor binding sites. A consensus viewpoint interprets these substitutions as making it more difficult for host inhibitory antibodies, elicited by previous exposure to the pathogen, to recognize new variant epitopes and block the interaction between the pathogen ligand and the host receptor (Bai et al., (2005) *Proc. Natl. Acad. Sci. USA* 102:12736; Coley et al., (2006) *Infection and Immunity* 74:2628; Crewther, et al., (1996) *Infection and Immunity* 64:3310; Healer et al., (2004) *Mol. Microbiol.* 52:159; Pizarro et al., (2005) *Science* 308:408; Smith et al., (2004) *Science* 305:371; Wilson & Cox (1990) *Annu. Rev. Immunol.* 8:737)

SUMMARY

The disclosure provides compositions that are useful for eliciting a strain-transcending immune response in an animal or human directed against the blood-stage of the malarial parasite *Plasmodium vivax*. The compositions of the disclosure are based on the ligand domain of *Plasmodium vivax* Duffy binding protein (PvDBPII). Polar charged polymorphic residues within the dominant strain-specific B-cell epitope were mutated to uncharged residues (e.g. serine, alanine and threonine). This DEKnull variant of PvDBPII is a recombinant protein produced in bacteria that can be purified and refolded in vitro to mimic conformation and erythrocyte binding function of native DBPII. Immunogenicity of DEKnull was confirmed by administration to mice. Compared to the naturally-occurring strain variant DBPII, DEKnull elicits antibodies that are more broadly reactive with different strain variants of DBPII and enhances production of functional inhibitory antibodies to the shared protective epitopes of native DBPII. Additionally, it has been shown that an immunogenic composition composed of a combination of DBPII strain variants Sal1, 7.18, and P also can enhance production of functional inhibitory antibodies to the shared protective epitopes of native DBPII. Priming vaccinations with DEKnull led to enhanced anamnestic responses to heterologous DBPII boosting vaccinations compared to prime-boost vaccinations with a single homologous DBPII variant. Results indicate vaccination with DEKnull, or a combination of DBPII strain variants can effectively overcome strain-limited responses inherent in vaccination with a single DBPII strain.

One aspect of the disclosure, therefore, encompasses embodiments of an engineered *Plasmodium vivax* Duffy Binding Protein (PvDBPII) having a modified region corresponding to an dominant immunogenic polymorphic B-cell epitopic region of a native PvDBPII, where the modified region has reduced immunogenic dominance when compared to the corresponding region of a native PvDBPII, and where the engineered PvDBPII can generate in a recipient animal or human subject an immune response having increased binding specificity for conserved Duffy binding epitopes of a *Plasmodium* Duffy Binding Protein when compared to an immune response generated by a natural PvDBPII variant.

In embodiments of this aspect of the disclosure, the dominant immunogenic polymorphic B cell epitopic region of the native PvDBPII can comprise an amino acid sequence having at least about 80% sequence similarity with the sequence DEKAQQRRKQWWNESK (SEQ ID No.: 3).

In embodiments of this aspect of the disclosure, the modified region of the engineered PvDBPII can have fewer polymorphic amino acids when compared to a dominant immunogenic polymorphic B-cell epitopic region of a native PvDBPII.

In embodiments of this aspect of the disclosure, the modified region of the engineered PvDBPII can have fewer polymorphic polar or charged residues when compared to a dominant immunogenic polymorphic B cell epitopic region of a native PvDBPII.

In embodiments of this aspect of the disclosure, the modified region of the engineered PvDBPII can comprise the amino acid sequence ASTAATSRTS (SEQ ID No.: 4).

In embodiments of this aspect of the disclosure, the amino sequence can have at least about 80% sequence similarity with the sequence SEQ ID No.: 2.

In embodiments of this aspect of the disclosure, the engineered PvDBPII can be expressed from a recombinant nucleic acid inserted into an expression vector.

Another aspect of the disclosure encompasses embodiments of a composition formulated for the generation in a recipient animal or human of an immune response, the composition comprising an engineered *Plasmodium vivax* Duffy Binding Protein (PvDBPII) having a modified region corresponding to an dominant immunogenic polymorphic B-cell epitopic region of a native PvDBPII, where the modified region can have reduced immunogenic dominance when compared to the corresponding region of a native PvDBPII, and where the engineered PvDBPII can generate in a recipient animal or human subject an immune response having increased binding specificity for conserved Duffy binding epitopes of a *Plasmodium* Duffy Binding Protein when compared to an immune response generated by a natural PvDBPII variant, and further comprising a pharmaceutically acceptable carrier.

In embodiments of this aspect of the disclosure, the pharmaceutical carrier can comprise an immunoadjuvant.

In embodiments of this aspect of the disclosure, the modified region of the engineered PvDBPII can have fewer polymorphic amino acids when compared to the corresponding dominant immunogenic polymorphic B-cell epitopic region of a native PvDBP In embodiments of this aspect of the disclosure, the modified region of the engineered PvDBPII can have fewer polymorphic polar or charged residues when compared to the corresponding dominant immunogenic polymorphic B-cell epitopic region of a native PvDBPII.

In embodiments of this aspect of the disclosure, the dominant immunogenic polymorphic B cell epitopic region of the native PvDBPII can comprise the amino acid sequence having at least about 80% sequence similarity with the sequence DEKAQQRRKQWWNESK (SEQ ID No.: 3).

In embodiments of this aspect of the disclosure, the modified region of the engineered PvDBPII can comprise the amino acid sequence ASTAATSRTS (SEQ ID No.: 4).

In embodiments of this aspect of the disclosure, the engineered PvDBPII can have an amino sequence having at least about 80% sequence similarity with the sequence SEQ ID No.: 2.

Yet another aspect of the disclosure encompasses embodiments of a method of eliciting in an animal or human subject an immune response, comprising administering to the subject an immunogenic composition comprising an engineered *Plasmodium vivax* Duffy Binding Protein (PvDBPII) comprising a modified region corresponding to an dominant immunogenic polymorphic B-cell epitopic region of a native PvDBPII, where the modified region can have reduced immunogenic dominance when compared to the corresponding region of a native PvDBPII, and where the elicited immune response has increased binding specificity for conserved Duffy binding epitopes of a *Plasmodium* Duffy Binding Protein compared to an immune response generated by a natural PvDBPII.

In embodiments of this aspect of the disclosure, the immunogenic composition can comprise the engineered PvDBPII and an immunoadjuvant.

In embodiments of this aspect of the disclosure, the engineered PvDBPII can have fewer polymorphic amino acids when compared to a dominant immunogenic polymorphic B-cell epitopic region of a native PvDBPII.

In embodiments of this aspect of the disclosure, the dominant immunogenic polymorphic B-cell epitopic region of a native PvDBPII can comprise the amino acid sequence having at least about 80% sequence similarity with the sequence DEKAQQRRKQWWNESK (SEQ ID No.: 3).

In embodiments of this aspect of the disclosure, the modified region of the engineered PvDBPII can comprise the amino acid sequence ASTAATSRTS (SEQ ID No.: 4).

In embodiments of this aspect of the disclosure, the engineered *Plasmodium vivax* Duffy Binding Protein can comprise the amino sequence having at least about 80% sequence similarity with the sequence SEQ ID No.: 2.

Still another aspect of the disclosure encompasses embodiments of a method of eliciting in an animal or human subject an immune response, comprising administering to the subject an immunogenic composition comprising a combination of *Plasmodium vivax* Duffy Binding Protein (PvDBPII) variants, wherein the elicited immune response has increased binding specificity for conserved Duffy binding epitopes of a *Plasmodium* Duffy Binding Protein compared to an immune response generated by a single natural PvDBPII.

In embodiments of this aspect of the disclosure, the immunogenic composition can comprise the *Plasmodium vivax* Duffy Binding Protein (PvDBPII) variants Sal 1, 7.18, and P, or immunogenic fragments thereof.

In embodiments of this aspect of the disclosure, the immunogenic composition can comprise the *Plasmodium vivax* Duffy Binding Protein (PvDBPII) variants Sal 1, 7.18, and P, having the amino acid sequences according to SEQ ID NOs.: 1, 6, and 7, respectively.

BRIEF DESCRIPTION OF THE DRAWINGS

Further aspects of the present disclosure will be more readily appreciated upon review of the detailed description of its various embodiments, described below, when taken in conjunction with the accompanying drawings.

FIG. 1 illustrates an alignment of the amino acid residues of coding region of DBPII-Sal1 (SEQ ID No.: 1) and DEKnull (SEQ ID No.: 2). The gene coding for the ligand domain of DBPII-Sal1 was used as a template to create the synthetic DBPII variant DEKnull (SEQ ID No.: 2). The most highly variant cluster of polar charged residues within the dominant B-cell epitope (underlined) as described by Chootong et al., (2010) *Infect. Immun.* 78: 1089-1095 were mutated to either alanine, threonine or serine. Asterisks (*) show different polymorphic sites within the DBPII region II (VanBuskirk et al., (2004) *Proc. Natl. Acad. Sci. U.S.A.* 101: 15754-15759).

FIG. 2A: SDS-PAGE gel of purified and refolded recombinant Sal1 and recombinant DEKnull. FIG. 2B: SDS-PAGE: differential mobility of reduced (+) and refolded (−) antigens. Mobility shift is a simple indicator of native conformation of recombinant antigens. FIG. 2C: Western blot: Standard erythrocyte binding assay showing binding of purified proteins to Duffy antigen receptor on erythrocytes (+) and no binding to erythrocytes treated with chymotrypsin (−). Arrows indicate the 39 kDa size of the recombinant proteins. PfAMA-1 and erythrocytes alone served as controls. FIG. 2D: Recombinant proteins were tested for binding to erythrocytes by flow cytometry. Bars indicate average relative binding of recombinant DEKnull to human erythrocytes compared to recombinant Sal1 for two independent experiments and error bars represent±STD.

FIG. 13 is a bar graph validating erythrocyte binding to COS7-expressed PvDBP-RII variants. pEGFP-Sal 1 (mut) differs from pEGFP-Sal 1 (original) by alteration of a Pvull restriction site to an EcoRI restriction site. Percent binding of each variant PvDBP-RII is shown relative to the pEGFP-Sal 1 (mut) variant.

FIGS. 14A-14E is a series of graphs illustrating the $IC_{50}$ (reciprocal of dilution required for 50% inhibition) of binding of each anti-PvDBP-RII sera of each PvDBP-RII antigen. Each panel represents a single anti-PvDBP-RII sera tested for inhibition of binding to each of five COS7-expressed PvDBP-RII variants. Each dot represents a single IC50 value and the red line represents the mean.

FIGS. 26A and 26B are digital images illustrating the cloning of synthetic PvDBP-RII variants into pEGFP-Sal 1 (mut) backbone.

FIGS. 31A-31 E are a series of graphs illustrating the inhibition of Duffy positive human erythrocyte binding to COS7-expressed PvDBP-RII variant 27.16.

FIGS. 40A-40E are a series of graphs illustrating the box and whiskers plots comparing the minimum level of each anti-PvDBP-RII sera required for 50% inhibition of each antigen ($IC_{50}$). The 50% Inhibition dilutions ($IC_{50}$) of each antisera were compared between COS7 expressed variants by Wilcoxon rank test. The charts show the mean 1C50 dilutions of each antisera across multiple experiments. The variation in means across variants show significant differences in inhibitory response of each antisera to the different variants tested. Box plots indicates the median, lower and upper quartiles of the dilutions FIGS. 41A-41 F are a series of graphs illustrating the day 42 baseline titers of anamenestic boost anti-sera to the prime immunization antigen.

FIGS. 42A-42F are a series of graphs illustrating the day 217 intermediate titers of anamenestic boost anti-sera to the prime immunization antigen.

FIG. 49A: SDS-PAGE gel of rDBPII variants purified by affinity chromatography from Ni+ column; FIG. 49B: Differential mobility of refolded antigens on SDS-PAGE gel before (−) and after (+) reduction with DTT; FIG. 49C: Western Blot: corresponding SDS-page of 1 b with reduced and refolded antigens probed with MAb-2d10 shows the monoclonal antibody reacting with refolded (−) but not reduce (+) antigens; FIG. 49A: Western blot: Erythrocyte binding assay showing binding of refolded antigens to Duffy positive erythrocytes (+) and reduced or no binding with Duffy positive erythrocytes treated with chymotrypsin (−). Duffy positive erythrocytes incubated with PfAMA-1 and erythrocytes without bound antigen were used as controls. Arrow indicates rDBPII at 39 kDa. Lane 1 & 2=Sal 1; 3 & 4=7.18; 5 & 6=P; 7 & 8=DEKnull; 9=PvMSP1-19; 10=PfAMA-1; 11=RBC without bound antigen; 12=refolded recombinant Sal 1 (Control).

FIGS. 50A-50E are a series of graphs illustrating the reactivity of anti-DBPII and anti-MSP1-19 immune sera with refolded rDBPII. Antigen preparations were adsorbed onto wells of micro titer plates (200 ng/well). Anti-serum from individual mice were tittered by end point dilution against each antigen on plate (starting at 1:4000 dilution). All OD values were normalized against a standard anti-DBPII monoclonal antibody which was run on each plate. Curves represent a 4 parametric logistic regression for the reactivity of immune sera from each cohort with homologous and heterologous antigens. Error bars represent the standard deviation. Anti-MSP1-19 antiserum and rMSP1-19 served as negative control antiserum and antigen respectively.

Figure 2A:
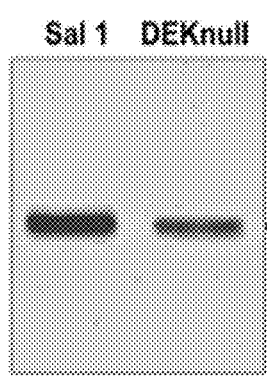
FIGS. 2A-2D illustrate the purification and functional analysis of recombinant proteins.

The drawings are described in greater detail in the description and examples below.

The details of some exemplary embodiments of the methods and systems of the present disclosure are set forth in the description below. Other features, objects, and advantages of the disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. Patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

ABBREVIATIONS

PvDBP: *Plasmodium* Duffy Binding Protein;

DEFINITIONS

The term "dominant immunogenic epitope" as used herein refers to an epitope located in or on such as a polypeptide against which an immune response is generated in preference to another immunogenic epitope on the same target antigen.

The term "protein" as used herein includes polypeptide and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

The term "variant" as used herein refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall (homologous) and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of this disclosure and still result in a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly where the biologically functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take one or more of the foregoing characteristics into consideration are well known to those of skill in the art and include, but are not limited to (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest. The term "substantially homologous" is used herein to denote polypeptides of the present disclosure having about 50%, about 60%, about 70%, about 80%, about 90%, and preferably about 95% sequence identity to the reference sequence. Percent sequence identity is determined by conventional methods as discussed above. In general, homologous polypeptides of the present disclosure are characterized as having one or more amino acid substitutions, deletions, and/or additions.

"Identity," as known in the art, is a relationship between two or more polypeptide sequences, as determined by comparing the sequences. In the art, "identity" also refers to the degree of sequence relatedness between polypeptides as determined by the match between strings of such sequences. "Identity" and "similarity" can be readily calculated by known methods, including, but not limited to, those described in Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo & Lipman (1988) SIAM J Applied Math., 48: 1073.

Preferred methods to determine identity (similarity) are designed to give the largest match between the sequences tested. Methods to determine identity and similarity are codified in publicly available computer programs. The percent identity between two sequences can be determined by using analysis software (i.e., Sequence Analysis Software Package of the Genetics Computer Group, Madison, Wis.) that incorporates the Needelman & Wunsch, (J. Mol. Biol., 48: 443-453, 1970) algorithm (e.g., NBLAST and XBLAST). The default parameters are used to determine the identity for the polypeptides of the present disclosure.

By way of example, a polypeptide sequence may be identical to the reference sequence, that is be 100% identical, or it may include up to a certain integer number of amino acid alterations as compared to the reference sequence such that the % identity is less than 100%. Such alterations are selected from: at least one amino acid deletion, substitution (including conservative and non-conservative substitution), or insertion, and wherein said alterations may occur at the amino- or carboxy-terminus positions of the reference polypeptide sequence or anywhere between those terminal positions, interspersed either individually among the amino acids in the reference sequence, or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from said total number of amino acids in the reference polypeptide.

Conservative amino acid variants can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methyl-glycine, allo-threonine, methylthreonine, hydroxy-ethylcysteine, hydroxyethylhomocysteine, nitro-glutamine, homoglutamine, pipecolic acid, thiazolidine carboxylic acid, dehydroproline, 3- and 4-methylproline, 3,3-dimethylproline, tert-leucine, norvaline, 2-azaphenyl-alanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an E. coli S30 extract and commercially available enzymes and other reagents. Proteins are purified by chromatography. (Robertson et al., *J. Am. Chem. Soc.*, 113: 2722, 1991; Ellman et al., *Methods Enzymol.*, 202: 301, 1991; Chung et al., *Science*, 259: 806-9, 1993; and Chung et al., *Proc. Natl. Acad. Sci. USA*, 90: 10145-9, 1993). In a second method, translation is carried out in Xenopus oocytes by microinjection of mutated mRNA and chemically aminoacylated suppressor tRNAs (Turcatti, et al., J. Biol. Chem., 271: 19991-8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. (Koide et al., *Biochem.*, 33: 7470-6, 1994). Naturally occurring amino acid residues can be converted to non-naturally occurring species by in vitro chemical modification. Chemical modification can be combined with site-directed mutagenesis to further expand the range of substitutions (Wynn, et al., Protein Sci., 2: 395-403, 1993).

Furthermore, unless the context demands otherwise, the term peptide, polypeptide and protein are used interchangeably to refer to amino acids in which the amino acid residues are linked by covalent peptide bonds or alternatively (where post-translational processing has removed an internal segment) by covalent disulfide bonds, etc. The amino acid chains can be of any length and comprise at least two amino acids, they can include domains of proteins or full-length proteins. Unless otherwise stated the terms peptide, polypeptide, and protein also encompass various modified forms thereof, including but not limited to glycosylated forms, phosphorylated forms, etc.

An "expression vector" is useful for expressing the DNA encoding the protein used herein and for producing the protein. The expression vector is not limited as long as it expresses the gene encoding the protein in various prokaryotic and/or eukaryotic host cells and produces this protein. Examples thereof are pMAL C2, pEF-BOS (Nucleic Acids Res. 18:5322 (1990) and so on), pME18S (Experimental Medicine: SUPPLEMENT, "Handbook of Genetic Engineering" (1992)), etc.

When bacteria, particularly *E. coli* are used as host cells, an expression vector generally comprises, at least, a promoter/operator region, an initiation codon, the DNA encoding the protein termination codon, terminator region, and replicon. When yeast, animal cells, or insect cells are used as hosts, an expression vector is preferably comprising, at least, a promoter, an initiation codon, the DNA encoding the protein and a termination codon. It may also comprise the DNA encoding a signal peptide, enhancer sequence, 5'- and 3'-untranslated region of the gene encoding the protein, splicing junctions, polyadenylation site, selectable marker region, and replicon. The expression vector may also contain, if required, a gene for gene amplification (marker) that is usually used.

A promoter/operator region to express the protein in bacteria comprises a promoter, an operator, and a Shine-Dalgarno (SD) sequence (for example, AAGG). For example, when the host is *Escherichia*, it preferably comprises Trp promoter, lac promoter, recA promoter, lambda. PL promoter, b 1pp promoter, tac promoter, or the like. Examples of a promoter to express the protein in yeast are PHO5 promoter, PGK promoter, GAP promoter, ADH promoter, and so on. When the host is *Bacillus*, examples thereof are SL01 promoter, SP02 promoter, penP promoter, and so on. When the host is a eukaryotic cell such as a mammalian cell, examples thereof are SV40-derived promoter, retrovirus promoter, heat shock promoter, and so on, and preferably SV-40 and retrovirus-derived one. As a matter of course, the promoter is not limited to the above examples. In addition, using an enhancer is effective for expression.

A preferable initiation codon is, for example, a methionine codon (ATG). A commonly used termination codon (for example, TAG, TAA, TGA) is exemplified as a termination codon. Usually, used natural or synthetic terminators are used as a terminator region.

The expression vector used herein can be prepared by continuously and circularly linking at least the above-mentioned promoter, initiation codon, DNA encoding the protein, termination codon, and terminator region, to an appropriate replicon. If desired, appropriate DNA fragments (for example, linkers, restriction sites, and so on), can be used by the usual method such as digestion with a restriction enzyme or ligation using T4 DNA ligase.

As used herein, "transformants" can be prepared by introducing the expression vector mentioned above into host cells.

The terms "host" and "host" cells" as used herein are not limited as long as they are compatible with an expression vector mentioned above and can be transformed. Examples thereof are various cells such as wild-type cells or artificially established recombinant cells usually used in technical field (for example, bacteria (*Escherichia* and *Bacillus*), yeast (*Saccharomyces, Pichia*, and such), animal cells, insect cells, or plant cells).

The terms "administering" and "administration" as used herein refer to introducing a composition (e.g., a vaccine, adjuvant, or immunogenic composition) of the present disclosure into a subject. The preferred route of administration of the vaccine composition is intravenous.

The term "immunogenic composition" are those which result in specific antibody production or in cellular immunity when injected into a host.

The term "specific binding" as used herein refers to the specific recognition of one molecule, of two different molecules, compared to substantially less recognition of other molecules. Generally, the molecules have areas on their surfaces or in cavities giving rise to specific recognition between the two molecules. Exemplary of specific binding are antibody-antigen interactions, enzyme-substrate interactions, polynucleotide interactions, and so forth.

The term "antibody" as used herein refers to an immunoglobulin which specifically binds to and is thereby defined as complementary with a particular spatial and polar organization of another molecule. The antibody can be monoclonal, polyclonal, or a recombinant antibody, and can be prepared by techniques that are well known in the art such as immunization of a host and collection of sera (polyclonal) or by preparing continuous hybrid cell lines and collecting the secreted protein (monoclonal), or by cloning and expressing nucleotide sequences, or mutagenized versions thereof, coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, IgY, etc. Fragments thereof may include Fab, Fv and F(ab')$_2$, Fab', scFv, and the like. In addition, aggregates, polymers, and conjugates of immunoglobulins or their fragments can be used where appropriate so long as binding affinity for a particular molecule is maintained.

The term "region" as used herein refers interchangeably with "domain" and refers to a functional unit of a peptide sequence.

As used herein, the term "engineered protein" refers to a non-naturally-occurring polypeptide. The term encompasses, for example, a polypeptide that comprises one or more changes, including additions, deletions or substitutions, relative to a naturally occurring polypeptide, wherein such changes were introduced by recombinant DNA techniques. The term also encompasses a polypeptide that comprises an amino acid sequence generated by man, an artificial protein, a fusions protein, and a chimeric polypeptide. Once expressed, recombinant peptides, polypeptides and proteins can be purified according to standard procedures known to one of ordinary skill in the art, including ammonium sulfate precipitation, affinity columns, column chromatography, gel electrophoresis and the like. Substantially pure compositions of about 50 to 99% homogeneity are preferred, and 80 to 95% or greater homogeneity are most preferred for use as therapeutic agents. Engineered proteins may be produced by any means, including, for example, peptide, polypeptide, or protein synthesis.

For the purposes of this invention, by "isolated" is meant material that has been removed from its natural state or otherwise been subjected to human manipulation. Isolated material may be substantially or essentially free from components that normally accompany it in its natural state, or may be manipulated so as to be in an artificial state together with components that normally accompany it in its natural state. Isolated material includes material in native and recombinant form.

The term "antigenic component" as used herein refers to a component derived from an organism capable of stimulating an immune response in an animal, preferably a mammal including mouse and human. An antigenic component may be an immunogenic agent. The antigenic component may comprise sub-cellular components including, organelles, membranes, proteins, lipids, glycoproteins and other components derived from the organism. The antigenic component may be derived from a whole organism, for example a whole parasite, or a part of an organism, for example a cell or tissue of an organism. Also, a sub-set of proteins may be purified, for example by size fractionation or affinity purification, and recombined.

The antigenic component can comprise purified proteins derived from the *Plasmodium* spp, recombinantly expressed nucleic acids encoding proteins derived from the *Plasmodium* spp, and a pool of recombinant expressed proteins derived from the *Plasmodium* spp. A preferred species of *Plasmodium* is one that is capable of infecting humans, for example *Plasmodium falciparum, Plasmodium vivax, Plasmodium malariae* or *Plasmodium ovale*.

An antigenic component preferably comprises an antigen of one or more strains of a species of *Plasmodium*. The antigenic component may also comprise one or more strains of any one or more of the different *Plasmodium* spp. The antigenic component comprises at least one strain of *Plasmodium* for each species capable of infecting a human, whereby heterologous immunity is provided for each strain of human *Plasmodium* spp when administered to a human. This is particularly advantageous as it will be appreciated there is potentially hundreds if not thousands of strains of *Plasmodium* capable of infecting humans, both known and unknown.

It will also be appreciated that the antigenic component of the invention, when administered to a subject preferably reduces infection or improves recover from infection from one or more species and strains of *Plasmodium*. Accordingly, in a preferred form of the compositions of the disclosure, administering to a human a pharmaceutical composition comprising an antigenic component from one or more different *Plasmodium* spp capable of infecting a human is capable of reducing or preventing malaria or improves recovery therefrom.

A "vaccine" is capable of providing protective immunity against an organism. The vaccine may provide protection against a same (i.e. homologous) or different (i.e. heterologous) strain of an organism. The vaccine of the invention preferably is capable of providing protection against homologous and heterologous species, variants or strains. In a preferred embodiment, the vaccine is capable of protecting or treating a human from infection from one or more heterologous strains of *Plasmodium*, for example, one, two, three, four, fix, six, seven, eight, nine, ten, 100, 200, 300, 400, 500, 600, 700, 800, 900, 1000 and even more than 1000 different strains of *Plasmodium*. Preferably, the *Plasmodium* spp is selected from a species capable of infecting a human, for example *Plasmodium falciparum, Plasmodium vivax, Plasmodium malariae* and *Plasmodium ovale*. The vaccine is preferably capable of protecting or treating a human from one or more different strains of one or more different species of *Plasmodium*.

A pharmaceutical composition may include, but is not limited to, an immunotherapeutic composition. An immunotherapeutic composition includes a vaccine. Suitably, the pharmaceutical composition comprises a pharmaceutically-acceptable carrier. By "pharmaceutically-acceptable carrier, diluent or excipient" is meant a solid or liquid filler, diluent or encapsulating substance that may be safely used in systemic administration. Depending upon the particular route of administration, a variety of carriers, well known in the art may be used. These carriers may be selected from a group including sugars, starches, cellulose and its derivatives, malt, gelatine, talc, calcium sulfate, vegetable oils, synthetic oils, polyols, alginic acid, phosphate buffered solutions, emulsifiers, isotonic saline, and pyrogen-free water.

The above compositions may be used as a therapeutic or prophylactic composition comprising a protein, preferably a plurality of pathogen proteins, more preferably a majority of pathogen proteins, even more preferably an extract derived from the pathogen. In one embodiment, the vaccine comprises an immunogenic agent as described above. Preferably, the vaccine prevents or treats infection by a parasite, more preferably infection by one or more different species of *Plasmodium* spp or one or more strains thereof. Accordingly, in a preferred form, the vaccine protects against both homologous and heterologous strains of *Plasmodium* spp, preferably one or more different strains of one or more different species capable of infecting humans, in particular, a *Plasmodium* spp selected from the group consisting of: *Plasmodium falciparum, Plasmodium vivax, Plasmodium malariae* and *Plasmodium ovale*.

Accordingly, the invention extends to the production of vaccines comprising as actives an antigenic component of the invention. Any suitable procedure is contemplated for producing such vaccines. Exemplary procedures include, for example, those described in NEW GENERATION VACCINES (1997, Levine et al., Marcel Dekker, Inc. New York, Basel Hong Kong) which is incorporated herein by reference. An immunogenic agent according to the invention can be mixed, conjugated or fused with other antigens, including B and/or T cell epitopes of other antigens. In addition, it can be conjugated to a carrier.

A number of vaccines have a short shelf life and must be stored at refrigeration temperatures. Optimally, a vaccine should have a long shelf life when stored at room temperatures.

As used herein, the term "antigen" refers to a molecule with one or more epitopes that stimulate a host's immune system to make a secretory, humoral and/or cellular antigen-specific response, or to a DNA molecule that is capable of producing such an antigen in a vertebrate. The term is also used interchangeably with "immunogen." For example, a specific antigen can be complete protein, portions of a protein, peptides, fusion proteins, glycosylated proteins and combinations thereof. For use with the compositions of the present disclosure, one or more PvDBPII antigens (native protein or protein fragment), may be provided directly or as part of a recombinant nucleic acid expression system to provide an antigenic PvDBPII product to trigger a host immune response.

As used herein, the term "gene" refers to a functional protein-, polypeptide-, or peptide-encoding nucleic acid unit, e.g., the PvDBP-encoding nucleic acids. As will be understood by those in the art, this functional term includes genomic sequences, cDNA sequences, probes, oligonucleotides or fragments thereof (and combinations thereof), as well as gene products, including those that may have been designed and/or altered by the user. Purified genes, nucleic acids, protein and the like are used to refer to these entities when identified and separated from at least one contaminating nucleic acid or protein with which it is ordinarily associated.

As used herein, the term "host cell" refers to cells that have been engineered to contain nucleic acid segments or altered segments, whether archeal, prokaryotic, or eukaryotic. Thus, engineered, or recombinant cells, are distinguishable from naturally occurring cells that do not have the recombinantly introduced genes.

As used herein, the term "vector" is used in reference to nucleic acid molecules that transfer DNA segment(s) from one cell to another. The term "vehicle" is sometimes used interchangeably with "vector." The term "vector" as used herein also includes expression vectors in reference to a recombinant DNA molecule containing a desired coding sequence and appropriate nucleic acid sequences necessary for the expression of the operably linked coding sequence in a particular host organism. Nucleic acid sequences necessary for expression in prokaryotes or eukaryotes usually include a promoter, an operator (optional), and a ribosome binding site, often along with other sequences. Eukaryotic cells are known to use promoters, enhancers, and termination and polyadenylation signals. Another, and different, way in which the term "vector," is used herein refers to the insect or other host that serves to deliver a parasite between organisms, e.g., mosquitoes are common "vectors" for parasites that are transmitted between humans or animals via the mosquito "vector." Other vectors include, e.g., fleas, mites, flies and the like, as will be known to those of skill in the art. Finally, the term "vector" may be used to describe the use of a carrier or other delivery system or organism to deliver the antigen(s) of the present invention to a host in order to trigger an immune response as part of a vaccine. Non-limiting examples of these vaccine vectors include viruses, bacteria, protozoans, cells (e.g., homologous or heterologous), etc., which may be live, live-attenuated, heat-killed, mechanically-killed, chemically-killed, recombinant (e.g., peptides, proteins and the like), as will be known to those skilled in the art of vaccine preparation. The skilled artisan will readily recognize the type of "vector" to which this specification and claims refer based on the description of the materials and methods used and described herein.

As used herein, the term "immunological response" refers to a composition or vaccine that includes a PvDBPII antigen and that triggers in the host a cellular- and/or antibody-mediated immune response to PvDBPII-derived antigens. Usually, such a response may include antibody production (e.g., in the intestinal tract, from germinal centers in lymph nodes, etc.), B cell proliferation, helper T cells, cytotoxic T cell proliferation, Natural Killer activation specifically to PvDBPII antigen or antigens against the PvDBPII target itself and/or fluids, secretions, tissues, cells or hosts infected therewith.

As used herein, the terms "vaccine composition" or "vaccine" refer to a PvDBPII antigen that is used to stimulate the immune system of a vertebrate, e.g., a bird, a fish, a mammal, or even a human, so that current harm is alleviated, or protection against future harm is provided by an adaptive immune response. An immune response may also be provided passively, by transferring immune protection (e.g., antibodies) from one "immunized" host to the recipient that has not been challenged by the antigen and/or is unable to generate an immune response to the antigen. An immune response may also carry from the host into the vector, wherein the antibodies that are ingested by the vector along with the parasites block parasite mating.

As used herein, the term "immunization" refers to the process of inducing a continuing protective level of antibody and/or cellular immune response which is directed against a PvDBPII antigen, either before or after exposure of the host to PvDBPII.

As used herein, the term "antibody" refers to polyclonal and monoclonal antibody preparations, as well as preparations including hybrid antibodies, altered antibodies, $F(ab')_2$ fragments, F(ab) fragments, Fv fragments, single domain antibodies, chimeric antibodies, humanized antibodies, and functional fragments thereof which exhibit immunological binding properties of the parent antibody molecule.

Methods of making polyclonal and monoclonal antibodies are known in the art. Polyclonal antibodies are generated by immunizing a suitable animal, such as a mouse, rat, rabbit, sheep or goat, with an antigen of interest. To enhance immunogenicity, the antigen can be linked to a carrier prior to immunization. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Furthermore, the antigen may be conjugated to a bacterial toxoid, such as toxoid from diphtheria, tetanus, cholera, etc., to enhance the immunogenicity thereof. Rabbits, sheep, mice, rats, hamsters, horses, cows and goats are often used for the preparation of polyclonal sera when large volumes of sera are desired. These animals are good design choices also because of the availability of labeled anti-host antibodies. Immunization is performed by mixing or emulsifying the antigen in saline, preferably in an adjuvant such as Complete Freund's Adjuvant ("CFA") and injected. The animal is boosted 2-6 weeks later with one or more injections of the antigen in saline, often with the antigen emulsified with Incomplete Freund's adjuvant ("IFA"). Antibodies may also be generated by in vitro immunization, using methods known in the art. Polyclonal antisera is then obtained from the immunized animal.

As used herein, the terms "antigen-binding site" or "binding portion" refer to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions," or "FRs". Thus the term "FR" refers to amino acid sequences which are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity, and is thus equal to the dissociation constant $K_d$.

As used herein, the term "Fab'," refers to a polypeptide that is a heterodimer of the variable domain and the first constant domain of an antibody heavy chain, plus the variable domain and constant domain of an antibody light chain, plus at least one additional amino acid residue at the carboxy terminus of the heavy chain $C_{H1}$ domain including one or more cysteine residues. F(ab')$_2$ antibody fragments are pairs of Fab' antibody fragments which are linked by a covalent bond(s). The Fab' heavy chain may include a hinge region. This may be any desired hinge amino acid sequence. Alternatively the hinge may be entirely omitted in favor of a single cysteine residue or, a short (about 1-10 residues) cysteine-containing polypeptide. In certain applications, a common naturally occurring antibody hinge sequence (cysteine followed by two prolines and then another cysteine) is used; this sequence is found in the hinge of human IgG1 molecules (E. A. Kabat, et al., Sequences of Proteins of Immunological Interest 3rd edition (National Institutes of Health, Bethesda, Md., 1987)). In other embodiments, the hinge region is selected from another desired antibody class or isotype.

As used herein, the term "hinge region" refers to an amino acid sequence located between $C_{H1}$ and $C_{H2}$ in native immunoglobulins or any sequence variant thereof. Analogous regions of other immunoglobulins will be employed, although it will be understood that the size and sequence of the hinge region may vary widely. For example, the hinge region of a human IgG.sub.1 is only about 10 residues, whereas that of human IgG3 is about 60 residues.

As used herein, the term Fv refers to a covalently or non-covalently-associated heavy and light chain heterodimer which does not contain constant domains. As used herein, the terms "Fv-SH" or "Fab'-SH" refers to an Fv or Fab' polypeptide having a cysteinyl free thiol. The free thiol is in the hinge region, with the light and heavy chain cysteine residues that ordinarily participate in inter-chain bonding being present in their native form. In the most preferred embodiments of this invention, the Fab'-SH polypeptide composition is free of heterogeneous proteolytic degradation fragments and is substantially (greater than about 90 mole percent) free of Fab' fragments wherein heavy and light chains have been reduced or otherwise derivatized so as not to be present in their native state, e.g. by the formation of aberrant disulfides or sulfhydryl addition products

DESCRIPTION

The present disclosure provides for variants of the *Plasmodium vivax* Duffy Binding Protein that have engineered to have regions of reduced immunogenic dominance when compared to native or non-engineered variants. The engineered variants of the disclosure are useful for the formulation of vaccines that can generate an immune response more specifically directed to the conserved Duffy binding ligand region that is found in a plurality of *P. vivax* strains. Such immunogenic compositions, therefore, can provide an immune protective response against a broader range of *P vivax* strains compared to the use of a single immunizing PvDBPII variant. It has further been found that a combination of PvDBPII variants co-administered to a subject can also generate an immune reaction circumventing the dominant immunogenic epitopes of PvDBPII to provide an immune reaction more specifically targeted to the conserved epitopes found in various PvDBPII variants.

*Plasmodium vivax* preferentially infects human reticulocytes expressing the surface DARC blood group antigen. The critical nature of the host cell specificity for parasite survival is evident from the virtual absence of *vivax* malaria from populations with high levels of DARC negativity and the difficulty culturing this parasite in blood not enriched for reticulocytes. Unlike *P. falciparum*, alternate invasion pathways have not been identified. Consequently, the PvDBPII represents an ideal potential target for vaccine development against *P. vivax* asexual blood stage infection. Potential confounding factors that may compromise its use as a vaccine have been revealed in studies on the naturally occurring serologic responses to DBPII after infection. Native DBPII is a relatively poor immunogen. Functional anti-DBPII activity is mostly weak and development of a broadly inhibitory strain-transcending immunity is a rather uncommon occurrence (Chootong et al., (2010) *Infect. Immun.* 78: 1089-1095; King et al., (2008) *Proc. Natl. Acad. Sci. U.S.A.* 105: 8363-8368)

While not wishing to be bound by any one theory, it is likely that the relative bias towards a weak, strain-specific DBPII antibody response following human infection is a consequence of the polymorphic nature of epitopes in the DBPII ligand domain. Most polymorphisms identified in DBPII are clustered within the central portion of the ligand domain, especially in the major variant cluster referred to as the DEK epitope (Chootong et al., (2010) *Infect. Immun.* 78: 1089-1095; King et al., (2008) *Proc. Natl. Acad. Sci. U.S.A.* 105: 8363-8368). This region of the ligand domain is also identified as responsible for determining receptor specificity and the epitopes that are the primary targets for antibody inhibition have been mapped to this region.

The present disclosure provides a non-native gene referred to as DEknull based on the Sal1 ligand domain that lacks highly charged, polar residues within the dominant B-cell epitope (Chootong et al., (2010) *Infect. Immun.* 78: 1089-1095). The recombinant nucleic acid encoding the DEKnull variant of DBPII was used to provide a purified and recombinant DEKnull that folded into a native conformation. Its immunological characteristics were determined. The expressed engineered antigen was found to be correctly refolded and functionally active as it was able to bind human erythrocytes expressing DARC, but not DARC negative erythrocytes (Singh et al., (2001) *J. Biol. Chem.* 276: 17111-17116; Yazdani et al., (2004) *Biotechnol. Lett.* 26: 1891-1895. Yazdani et al., (2004) *Vaccine* 22: 3727-3737). The modified DEKnull antigen lacked polymorphic residues within the dominant B-cell epitope but still bound to human erythrocytes with specificity similar to the native protein. This confirms previous data demonstrating that the polymorphic residues within the hypervariable segment of DBPII generally are not critical for erythrocyte binding activity (Hans et al., (2005) *Mol. Microbiol.* 55: 1423-1434; VanBuskirk et al., (2004) *Proc. Natl. Acad. Sci. U.S.A.* 101: 15754-15759). Furthermore, the functionality of the altered residues is consistent to similar mutagenesis of the homologous DBL domain of *P. falciparum* EBA-175, which also has naturally occurring polymorphisms that do not affect erythrocyte-binding properties (Liang & Sim (1997) *Mol. Biochem. Parasitol.* 84: 241-245; Xainli et al., (2000) *Mol. Biochem. Parasitol.* 111: 253-260).

A desirable vaccine candidate should induce high titers of functional antibodies. Immunizations with recombinant proteins DEKnull, of the disclosure, and Sal1 induced high-titer immune sera in rats with antibodies reactive against both DEKnull and Sal1. The Sal1 antiserum displayed a higher level of reactivity to the Sal1 versus the DEKnull protein, whereas the anti-DEKnull antiserum had a nearly identical reactivity profiles to both homologous Sal1 and heterologous DEKnull antigens, confirming the immunogenicity of the DEK epitope and also the presence of other immunogenic epitopes on native DBPII.

Consistent with the presence of other target epitopes we found that naturally acquired, inhibitory immune sera (King et al., (2008) *Proc. Natl. Acad. Sci. U.S.A.* 105: 8363-8368) were highly reactive with DEKnull, indicating that the synthetic DEKnull antigen contains conserved epitopes associated with a protective immune response despite lacking an dominant immunogenic epitope. Functional in vitro assays demonstrated both antisera completely inhibited DBPII-erythrocyte binding at a dilution up to 1:500. The functional importance of the DEK epitope as a target of protective anti-DBPII immunity was confirmed by differences in the $IC_{50}$ values for anti-Sal1 and anti-DEKnull inhibition of Sal1-erythrocyte binding.

The Duffy binding protein is contemplated to be a leading vaccine candidate against asexual blood stage *Plasmodium vivax*. The interaction of merozoites with human erythrocytes through Duffy binding protein (DBPII) and its cognate receptor, the Duffy antigen receptor for chemokines (DARC) is vital for parasite invasion of erythrocytes. The ligand domain of DBPII (DBPII) is polymorphic, showing a diversity characteristic of selective immune pressure that tends to compromise vaccine efficacy associated with strain-specific immunity. While not wishing to be bound by any one theory, the polymorphic residues, which are not functionally important for erythrocyte binding, could comprise variant epitopes that tend to divert the immune response away from more conserved epitopes. A polymorphic epitope in the central portion of DBPII, containing highly polar or charged residues, was the dominant B-cell epitope target of human inhibitory anti-DBPII antibodies. A DEKnull variant of the present disclosure lacks any of the naturally occurring polymorphic residues of this dominant neutralizing epitope. The DEKnull antigen retained erythrocyte binding activity and elicited antibodies to the shared epitopes of native DBPII Sal1 from which it was derived. The results showed that removal of the dominant variant epitope in the DEKnull vaccine lowered immunogenicity of DBPII, but inhibitory anti-DBPII antibodies were elicited against shared neutralizing epitopes on DBPII Sal1. Focusing immune responses towards more conserved DBPII epitopes can avoid development of a strain specific immunity to enhance functional inhibition against a broader range of DBPII variants.

In *Plasmodium vivax*, merozoite invasion of human reticulocytes is dependent on interaction of the Duffy binding protein (DBPII) with its cognate receptor, the Duffy antigen receptor for chemokines (DARC) (Barnwell & Wertheimer (1989) *Prog. Clin. Biol. Res.* 313: 1-11; Horuk et al., (1993) *Science* 261:1182-1184; Miller et al., (1975) *Science* 189: 561-563). This molecule plays a critical role during the process of junction formation just before invasion and unlike *P. falciparum* there is no known alternate invasion pathway (Aikawa et al., (1978) *J. Cell Biol.* 77: 72-82; Dvorak et al., (1975) *Science* 187: 748-750).

DBPII is a member of the Duffy binding-like erythrocyte binding protein (DBL-EBP) family from the erythrocyte-binding-like (ebl) genes, sequestered in the micronemes and released to the merozoite surface to bind receptors on erythrocytes during the early invasion process (Adams et al., (1990) *Cell* 63: 141-153; Adams et al., (1992) *Proc. Natl. Acad. Sci. U.S.A.* 89: 7085-7089). The receptor-binding domain of DBPII is a conserved cysteine-rich motif known as region II and is the defining N-terminal extracellular domain of the DBPII and related ligands where residues critical for receptor recognition are located (Adams et al., (1992) *Proc. Natl. Acad. Sci. U.S.A.* 89: 7085-7089; Chitnis et al., (1996) *J. Exp. Med.* 184: 1531-1536; Ranjan & Chitnis. (1999) *Proc. Natl. Acad. Sci. U.S.A.* 96: 14067-14072; VanBuskirk et al., (2004) *Proc. Natl. Acad. Sci. U.S.A.* 101: 15754-15759). Several studies have shown that anti-DBPII antibodies, either natural or artificially induced, are able to inhibit erythrocyte invasion and DBPII binding to human erythrocytes in standard in vitro assays (Chootong et al., (2010) *Infect. Immun.* 78: 1089-1095; Dutta et al., (2000) *Mol. Biochem. Parasitol.* 109: 179-184; Grimberg et al., (2007) *PLoS Med.* 4: e337; McHenry et al., (2011) *PLoS One* 6: e20192; Michon et al., (2000) *Infect. Immun.* 68: 3164-3171; Yazdani et al., (2004) *Biotechnol. Lett.* 26: 1891-1895). These data indicate that DBPII is a suitable target for an antibody-based vaccine against asexual blood-stage *P. vivax*. Therefore, the potential for effective antibody inhibition of merozoites, its biological importance and the lack apparent alternate indicate the possible use of DBPII in a vaccine.

Diversity in the ligand domain, however, compromises vaccine efficacy. Alleles of this target domain have a very high ratio of non-synonymous mutation to synonymous mutations, reflecting a mechanism consistent with a high selection pressure driving DBPII allelic diversity as a mechanism for evasion for targets of inhibitory immunity (Ampudia et al., (1996) *Mol. Biochem. Parasitol.* 78: 269-272; Cole-Tobian & King (2003) *Mol. Biochem. Parasitol.* 127: 121-132; Ntumngia et al., (2009) *Am. J. Trop. Med. Hyg.* 80: 218-227; Tsuboi et al., (1994) *Infect. Immun.* 62: 5581-5586; Xainli et al., (2000) *Mol. Biochem. Parasitol.* 111: 253-260). As a consequence, these polymorphisms have posed a potential serious challenge for development of a broadly effective vaccine based on the DBPII against diverse *P. vivax* strains.

Naturally acquired human antibodies have been used to identify dominant B-cell epitopes within DBPII that correlate with functional inhibition of the ligand domain (Chootong et al., (2010) *Infect. Immun.* 78: 1089-1095). The dominant B-cell epitopes identified were surface-exposed motifs with clusters of polymorphic residues that are not important for erythrocyte binding (VanBuskirk et al., (2004) *Proc. Natl. Acad. Sci. U.S.A.* 101: 15754-15759).

Immune selection reported with other pathogens commonly involves variant residues adjacent to residues important for receptor recognition (Barouch, D. H. (2007) *AIDS Clin. Care* 19: 93; Smith et al., (2004) *Science* 305: 371-376; Smith et al., (2004) *Science* 305: 788-792; Walker & Burton (2008) *Science* 320: 760-764). As most naturally acquired infections with *P. vivax* tend to elicit weakly reactive and strain-specific antibodies, it was contemplated that the polymorphic dominant B-cell epitopes represent an evasion mechanism that misdirects the immune response away from more conserved less immunogenic epitopes that are potential targets for strain-transcending immunity. The presence of dominant epitopes can create an inherent bias towards a strain-specific response and limit induction of immune responses toward the more conserved non-strain-specific protective epitopes (Tobin et al., (2008) *Vaccine* 26: 6189-6199; Welsh & Fujinami (2007) *Nat. Rev. Microbiol.* 5: 555-563). Accordingly, the present disclosure provides novel DBPII immunogen, referred to as DEKnull, lacking the polymorphic-polar/charged residues that are normally present in the dominant polymorphic epitope. This focuses the immune response towards more conserved neutralizing epitopes that can have a broader functional inhibition against DBPII variants.

The present disclosure provides data demonstrating that DBPII is naturally immunogenic. Naturally acquired or artificially induced anti-DBPII antibodies can effectively block DBPII binding to human erythrocytes and identified the epitope targets of inhibition in the ligand domain (Grimberg et al., (2007) *PLoS Med.* 4: e337; Singh et al., (2001) *J. Biol. Chem.* 276: 17111-17116; Yazdani et al., (2004) *Vaccine* 22: 3727-3737). However, anti-DBPII antibodies are weak or unstable, short-lived and strain-specific (Ceravolo et al., (2009) *Clin. Exp. Immunol.* 156: 502-510; VanBuskirk et al., (2004) *J. Infect. Dis.* 190: 1556-1562). In contrast, the artificial DBPII immunogen of the disclosure, referred herein as DEKnull or PvDBP-RII, lacks the strongly charged residues of the dominant B-cell epitope. Serologic studies to this synthetic antigen in animals demonstrated that it was highly immunogenic and induced the production of functional antibodies that inhibited erythrocyte-binding activity of the natural Sal1 variant. It is contemplated that this type of immunogen can be useful to avoid induction of strain-specific responses to the dominant variant epitopes and thereby direct and enhance the immune response to more conserved neutralizing epitopes that are significant potential targets for strain-transcending immunity.

Immunization of mice with the individual PvDBP-RII variants Sal 1, 7.18, or P, the synthetic variant PvDBP-RII DEKnull, a combination of the PvDBP-RII variants Sal 1, 7.18 and P, together with the negative control antigen PvMSP1-19 was carried out. The resulting antisera were tested for immunogenicity and cross-reactivity by ELISA. The antisera raised against a combination of PvDBP-RII Sal 1, 7.18, and P immunogens (anti-PvDBP-RII Sal 1/7.18/P) were more reactive in the ELISA compared to the anti-PvDBP-RII Sal 1, anti-PvDBP-RII 7.18 or anti-PvDBP-RII DEKnull sera raised against the individual immunogens. However, all PvDBP-RII immunogens produced high titers to their respective homologous antigens, as shown in FIGS. 7-12 and 19A-23F). Each cohort of anti-PvDBP-RII sera reacted equally well to the PvDBP-RII antigens tested, as shown in FIGS. 7-11.

Figure 13:
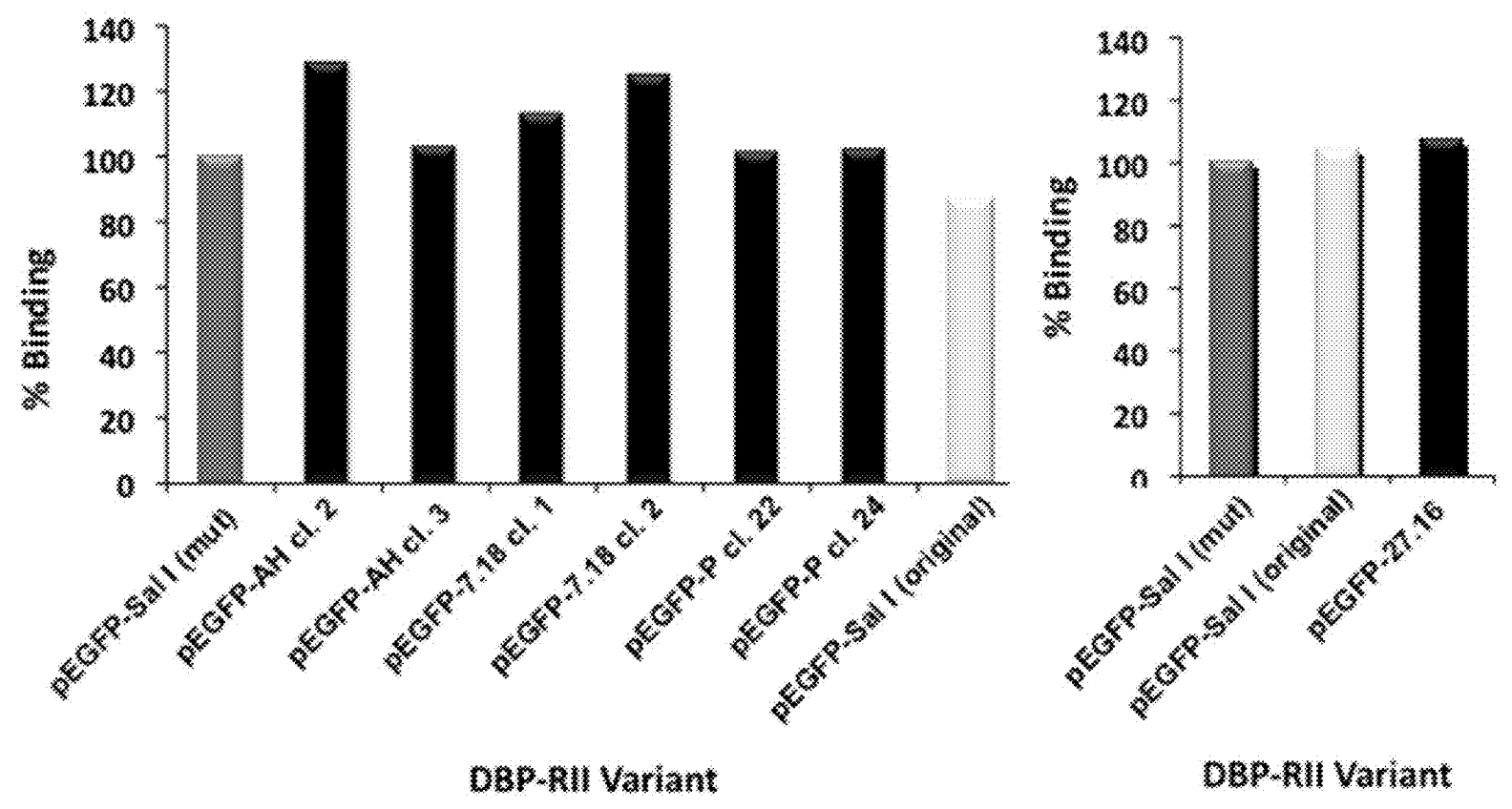

Antisera pooled by cohort were tested for their ability to inhibit binding of human erythrocytes to five genetically modified COS7 cell lines, each expressing a PvDBP-RII variant immunogen, i.e., Sal 1, 27.16, 7.18, AH or P. The variant immunogen were chosen as representing a divergent polymorphism and to have a geographically and genetically diverse sample set (see Table 3). All COS7-expressed PvDBP-RII variants were validated for their abilities to bind erythrocytes before using, as shown in FIG. 13). FIGS. 25A-26B show the molecular steps used to create the COS7 PvDBP-RII constructs. There was no correlation between the reactivity of the antisera by ELISA (i.e, titer) and functional inhibitory capacity of each antiserum in the COS7 erythrocyte binding inhibition assay (anti-PvDBP-RII Sal 1 p=0.12, anti-PvDBP-RII 7.18 p=0.46, anti-PvDBP-RII P p=0.91, anti-PvDBP-RII DEKnull p=0.96, anti-PvDBP-RII Sal 1/7.18/P p=1.0).

The minimum dilution of anti-PvDBP-RII sera to inhibit 50% of binding of human erythrocytes was determined for each COS7-expressed PvDBP-RII variant, as shown in FIGS. 14A-14E. The anti-(PvDBP-RII Sal 1/7.18/P) sera had a higher overall inhibitory response than any of the single variant anti-PvDBP-RII sera, even against PvDBP-RII variants not included in the mixed variant vaccination. However, although the anti-PvDBP-RII DEKnull sera had lower titers, the sera recognized and inhibited binding to the natural PvDBP-RII variants, indicating the presence of antibodies to shared neutralizing epitopes.

Figure 15:
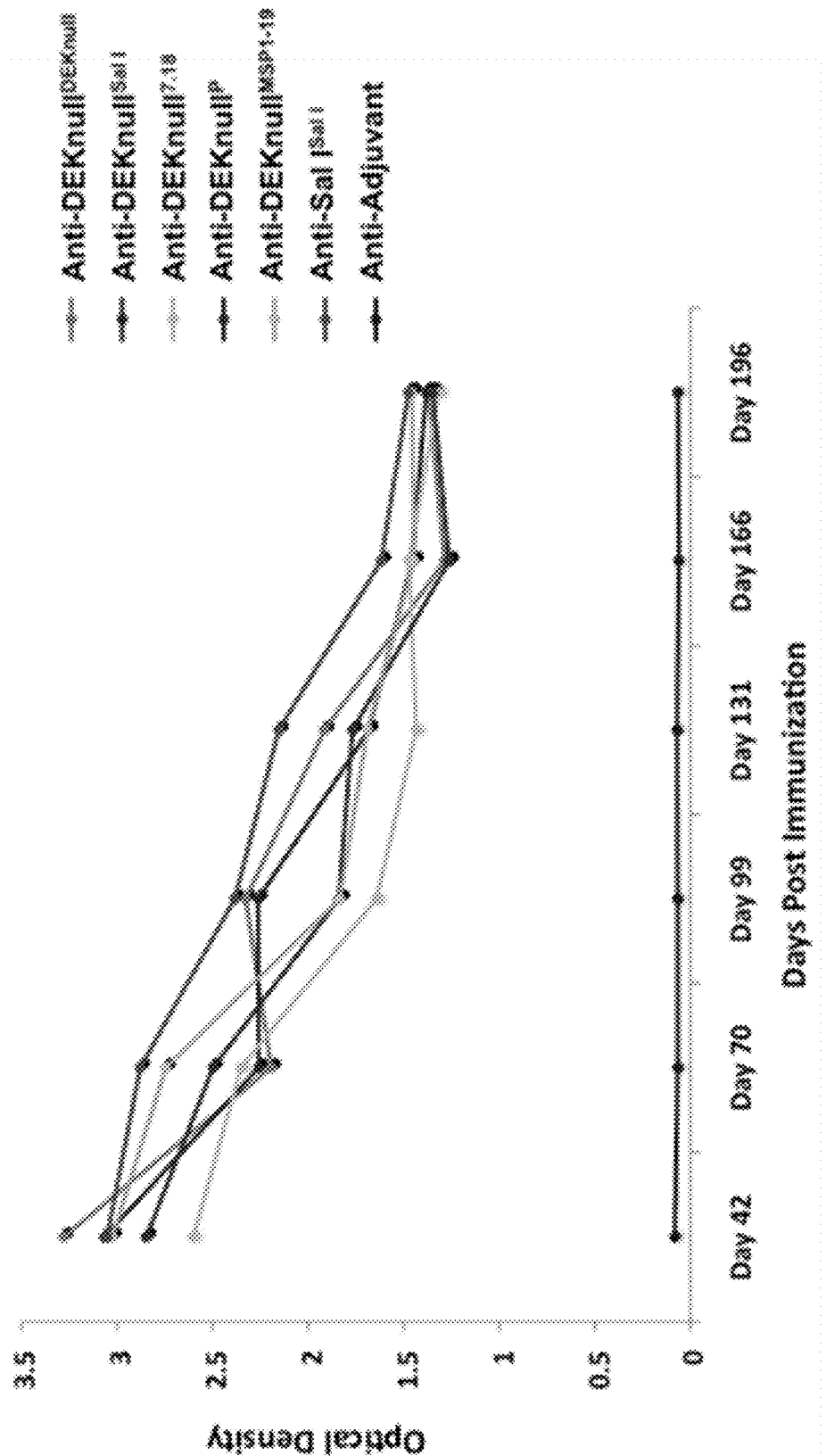
FIG. 15 is a graph illustrating the monitoring of IgG levels of anamnestic boost mice (Group 2). Following the initial homologous boost of each cohort on Day 21, mice were monitored with monthly test bleeds starting on Day 42 to determine when their IgG levels had fallen sufficiently to perform the anamnestic boost.
Figure 16:
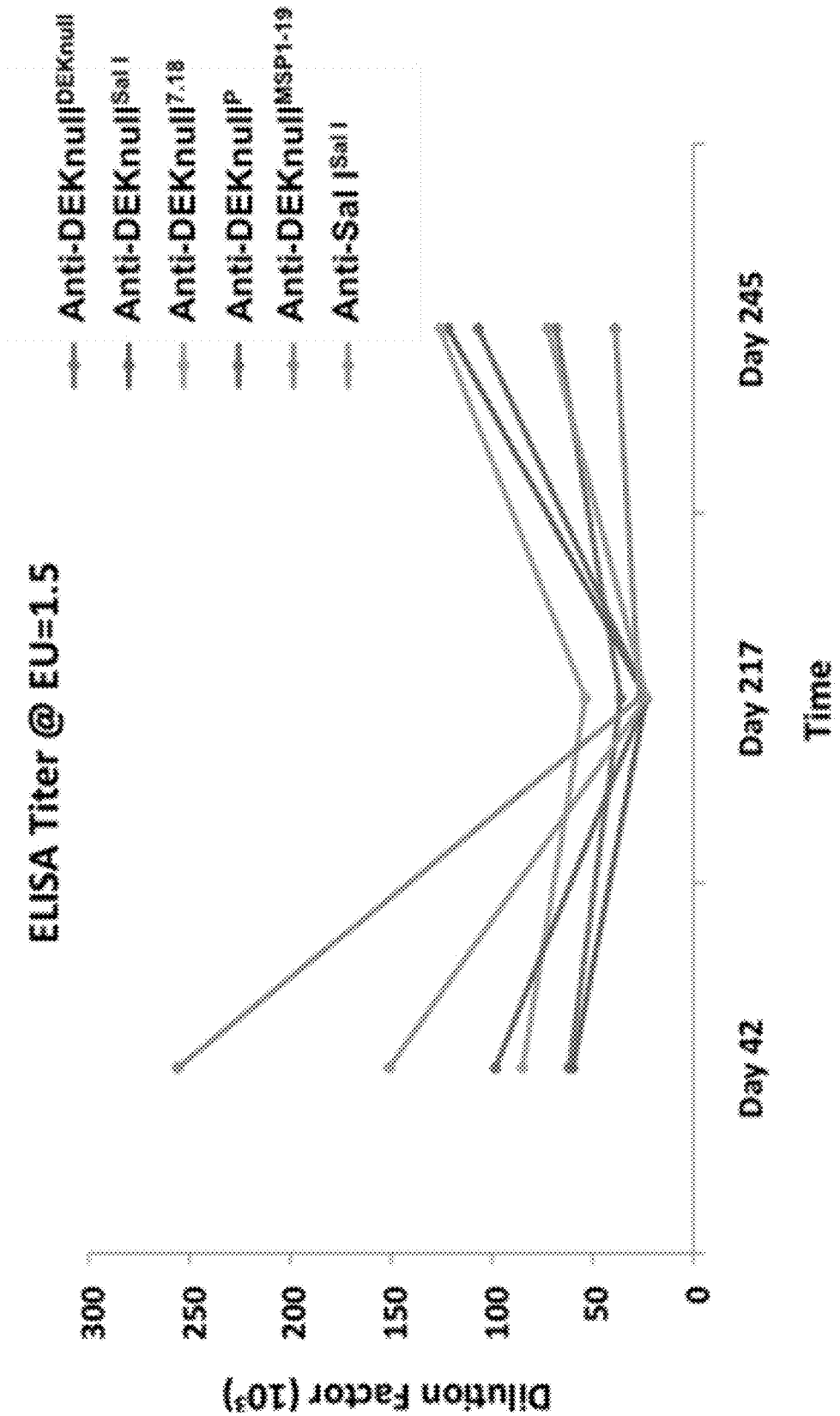
FIG. 16 is a graph illustrating the time course of IgG levels of each cohort of anamnestic boost anti-sera measured at EU=1.5 on Day 42, 217 and 245. There was a significant drop in IgG levels from Day 42 to Day 217 for all cohorts (p=0.0007). IgG levels on Day 42 and Day 245 were not significantly different (P=0.4) indicating a memory response (with the exception of anti-DEKnull$^{MSP1-19}$). Anti-sera on Day 42 and 217 were tittered against the prime immunization antigen. Anti-sera on Day 245 were tittered against the anamnestic boost antigen.

To assess anamestic boost, six cohorts of mice received initial immunizations with either PvDBP-RII Sal 1 or PvDBP-RII DEKnull. They each received a prime boost with their homologous antigen on Day 21, and an anamnestic boost with either homologous or heterologous antigen on Day 224. Test bleeds were taken initially on Day 42 and subsequently every month until the IgG levels had fallen approximately 50% (Day 217), as shown in FIG. 15, after which the anamnestic boost was given at Day 224, and the final bleeds taken at Day 245. Serum samples were then analyzed by ELISA.

Figure 17:
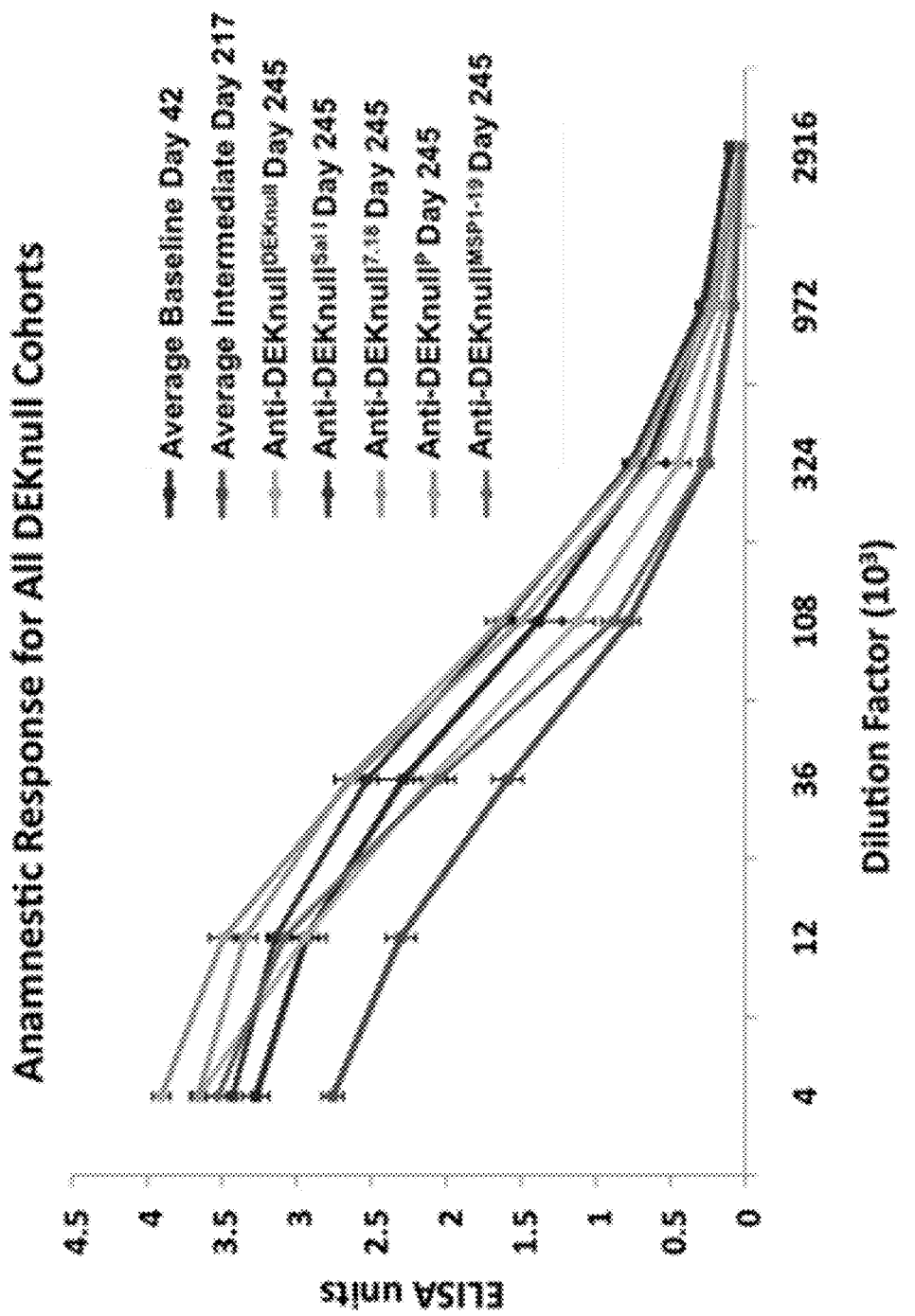
FIG. 17 is a graph illustrating the anamnestic response for all DEKnull cohorts. The average baseline curve (Day 42) for all cohorts initially immunized with DEKnull is shown in dark blue. The average intermediate curve (Day 217) for all cohorts initially immunized with DEKnull is shown in red. Other curves indicate the IgG levels of each cohort of final bleed sera (Day 245) tittered against their respective anamnestic boost antigens.
Figure 18:
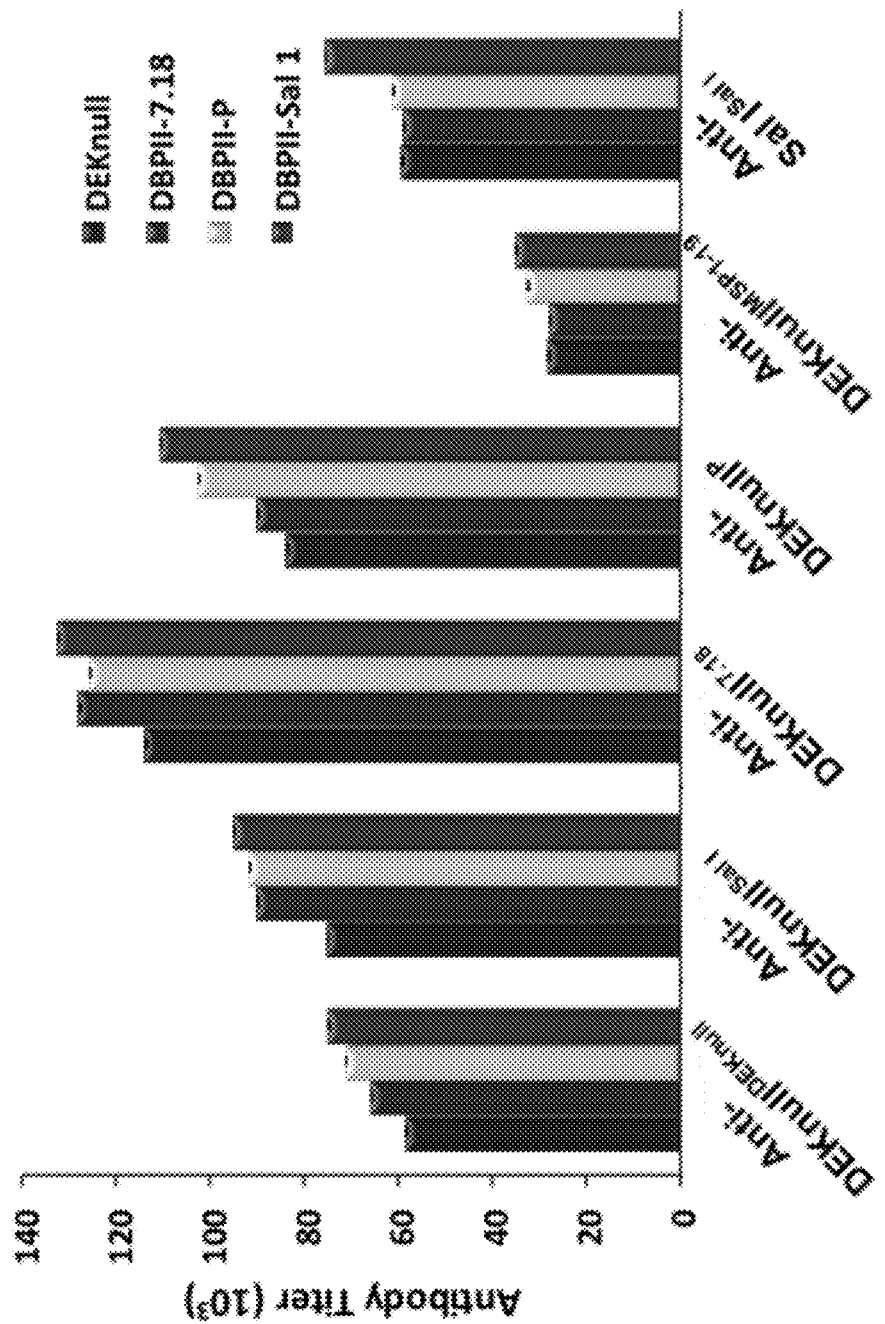
FIG. 18 is a graph illustrating the anamnestic boost antisera react equally well to each PvDBP-RII antigen. IgG responses of anamnestic boost anti-sera to PvDBP-RII antigens at EU=1.5. Antibody titers shown were determined in pooled sera (n=14) from each immunized cohort measured against the different PvDBP-RII variants as coating antigen. ELISA titers were calculated values as interpolated titers at an ELISA Unit of 1.5. Bars represent mean ELISA titers of two independent experiments carried out in triplicate.
Figure 19A:
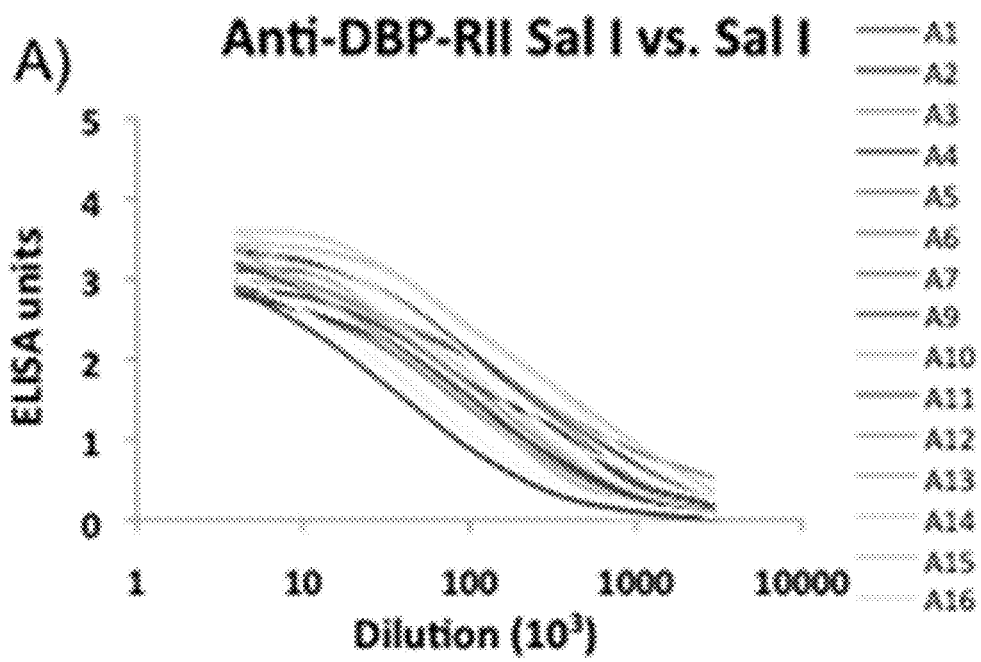
FIGS. 19A and 19B are graphs illustrating the assessment of immunogenicity of anti-PvDBP-RII Sal 1 sera against homologous antigen PvDBP-RII Sal 1
Figure 19B:
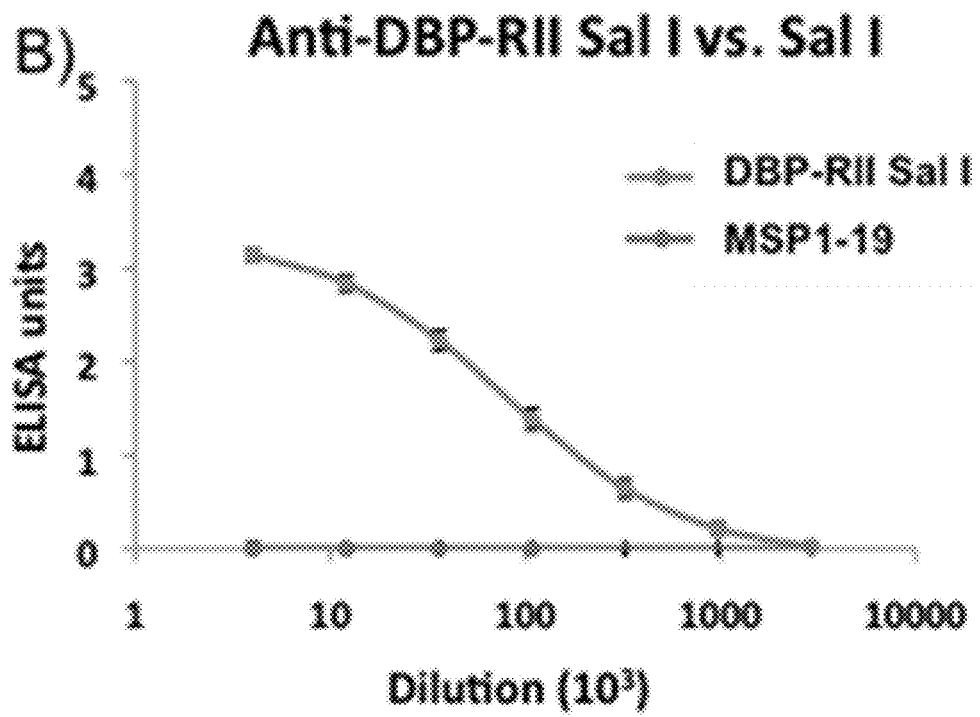
Figure 20A:
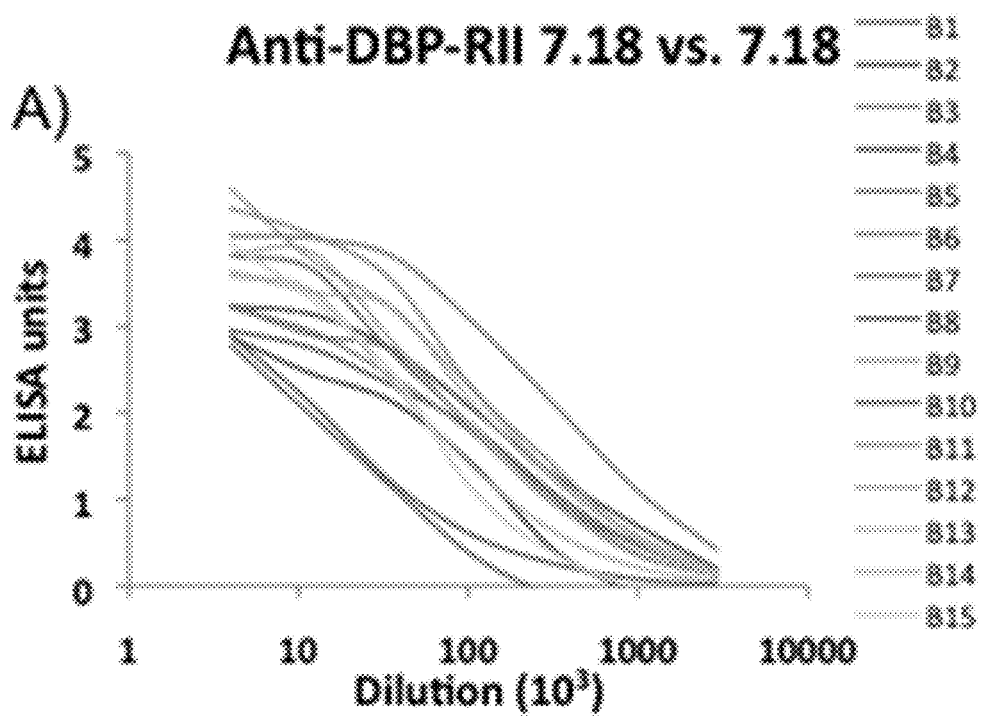
FIGS. 20A and 20B are graphs illustrating the assessment of immunogenicity of anti-PvDBP-RII 7.18 sera against homologous antigen PvDBP-RII 7.18.
Figure 20B:
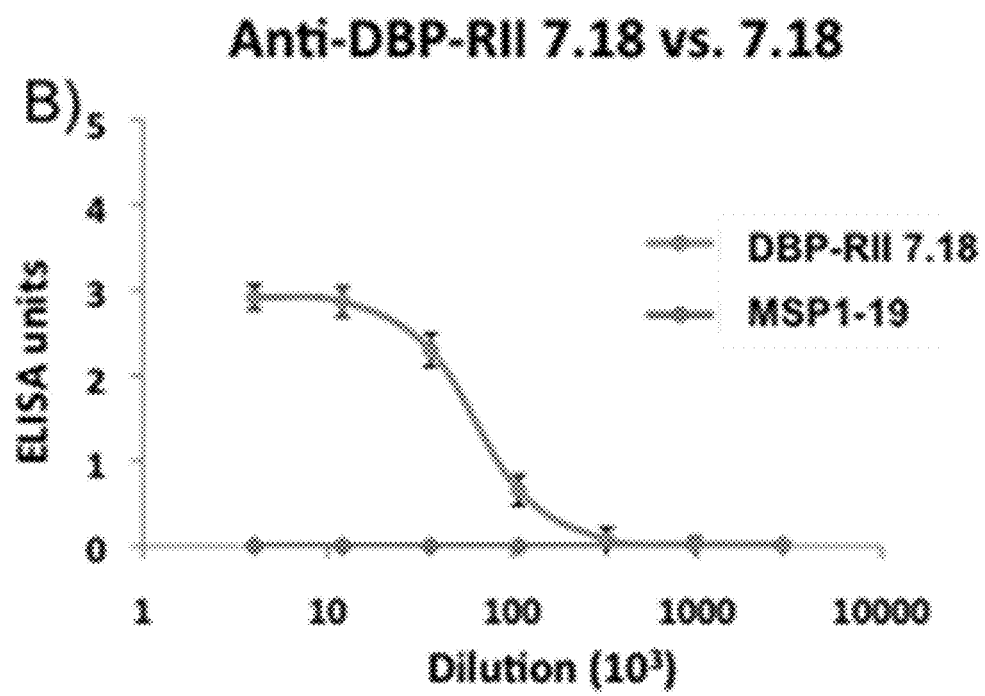
Figure 21A:
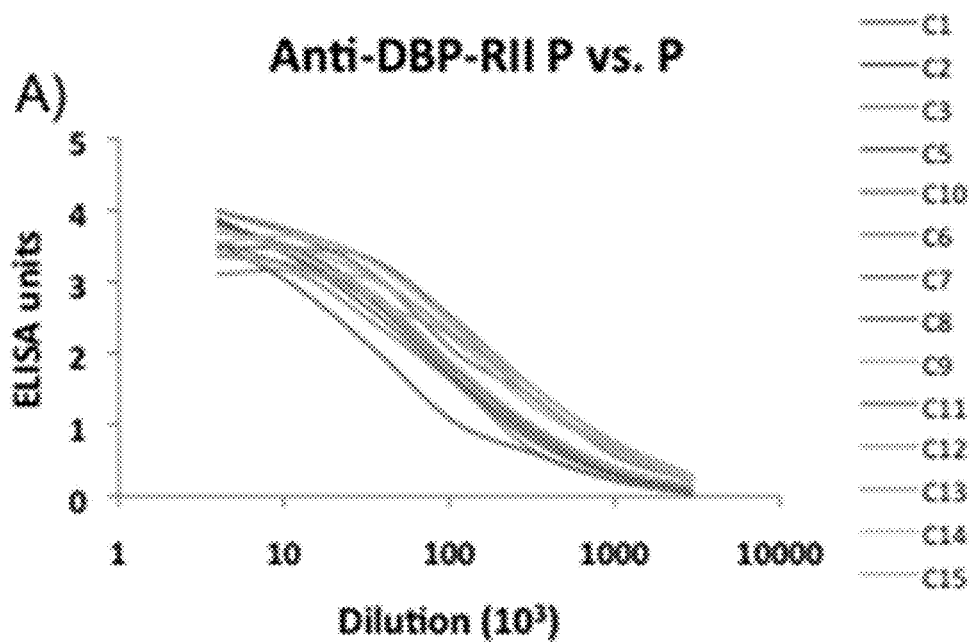
FIGS. 21A and 21B are graphs illustrating the assessment of immunogenicity of anti-PvDBP-RII P sera against homologous antigen PvDBP-RII P.
Figure 21B:
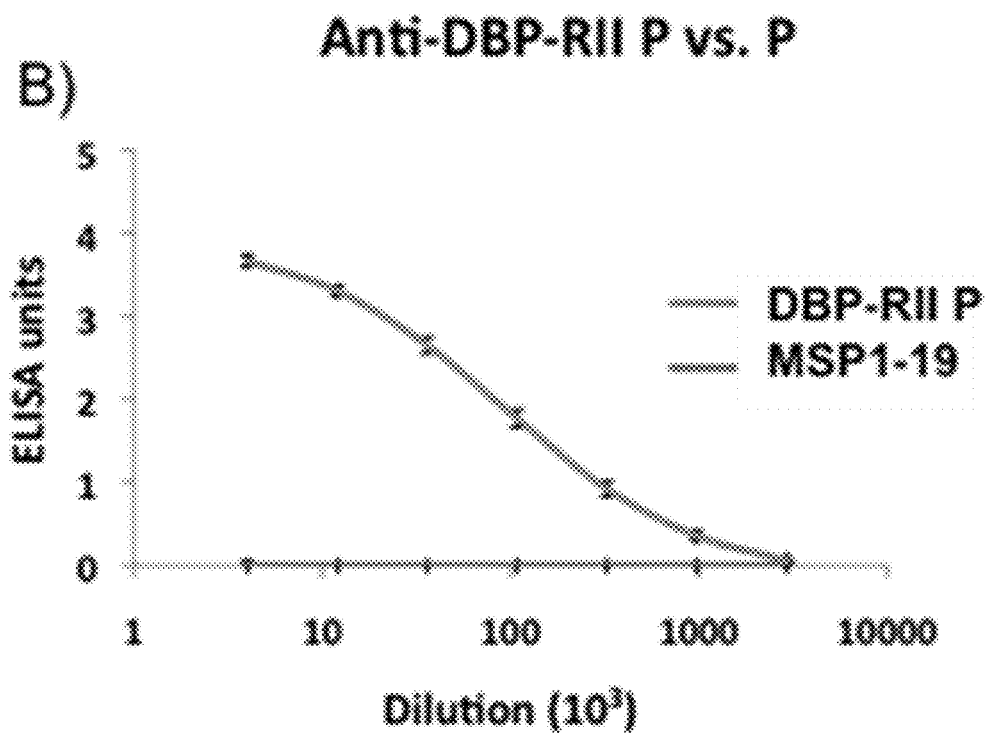
Figure 22A:
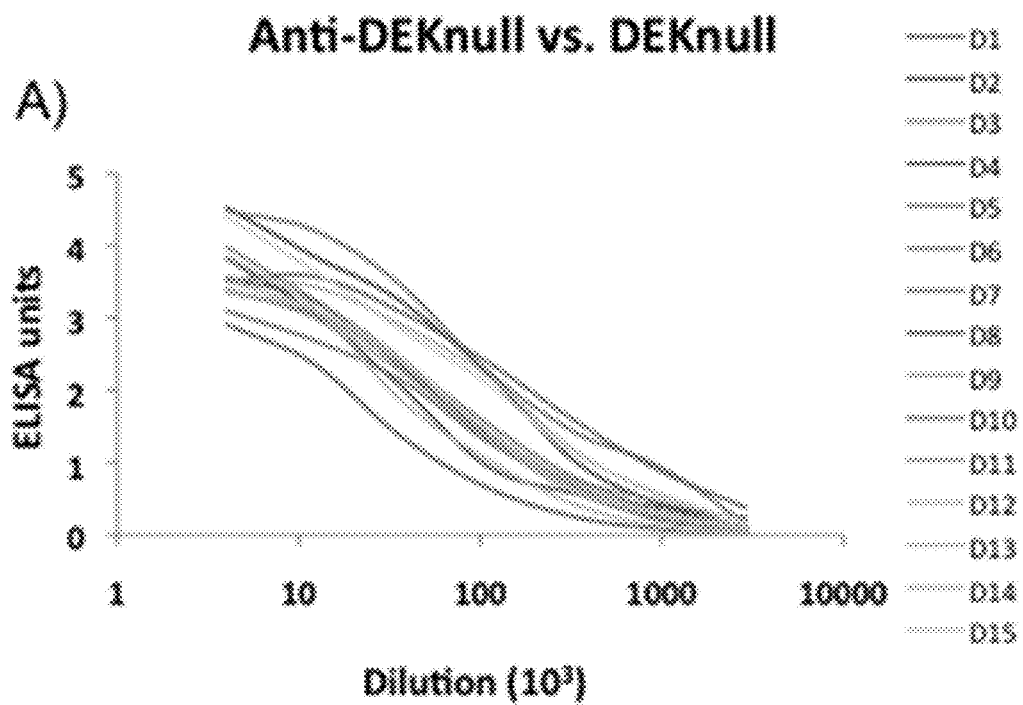
FIGS. 22A and 22B are graphs illustrating the assessment of immunogenicity of anti-DEKnull sera against homologous antigen DEKnull.
Figure 22B:
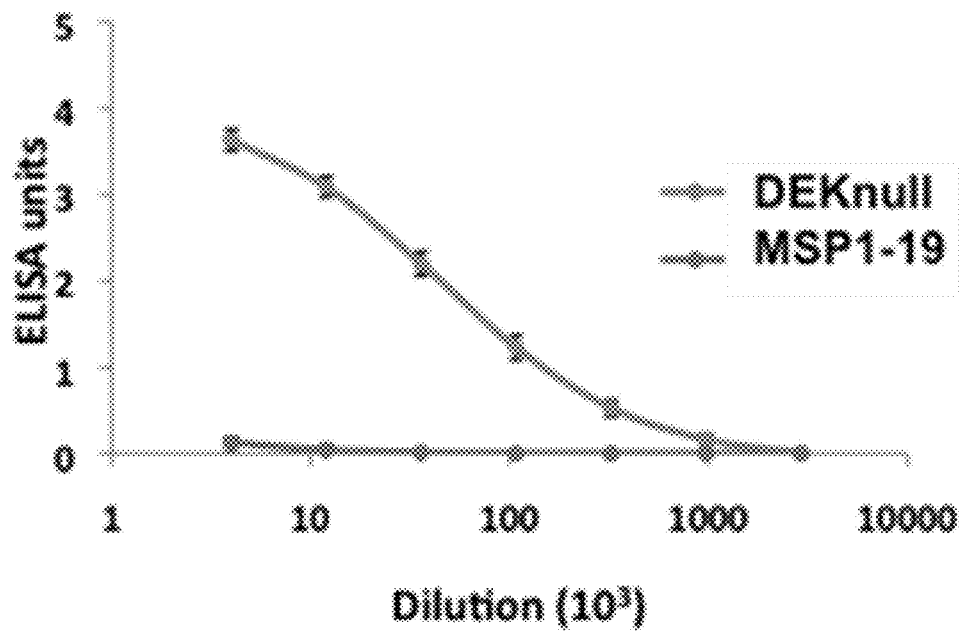
Figure 23A:
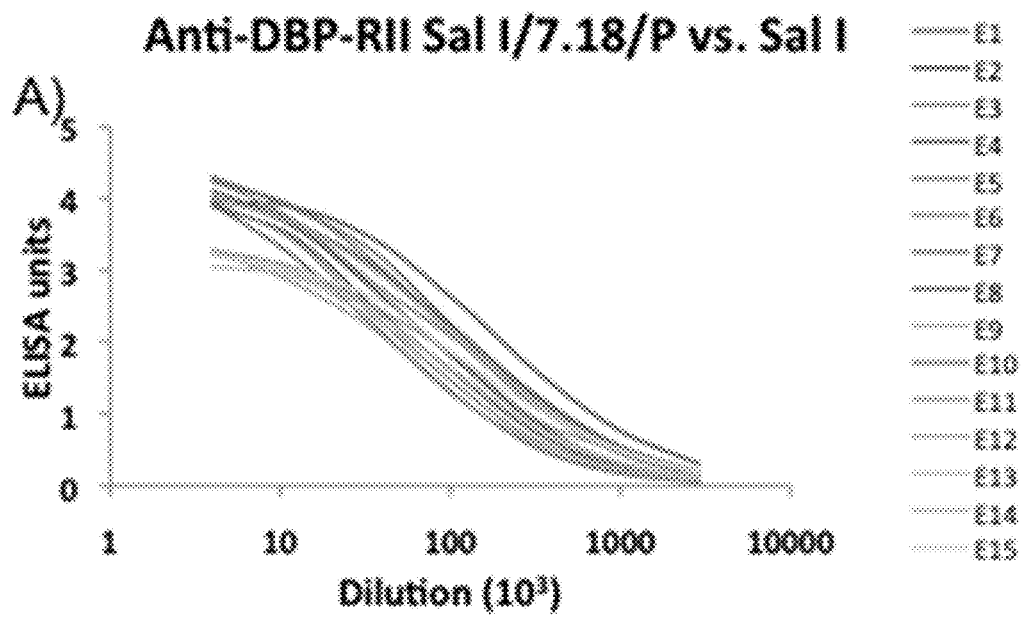
FIGS. 23A-23F are graphs illustrating the assessment of immunogenicity of anti-PvDBP-RII Sal 1/7.18/P sera against homologous antigens PvDBP-RII Sal 1, PvDBP-RII 7.18 and PvDBP-RII P.
Figure 23B:
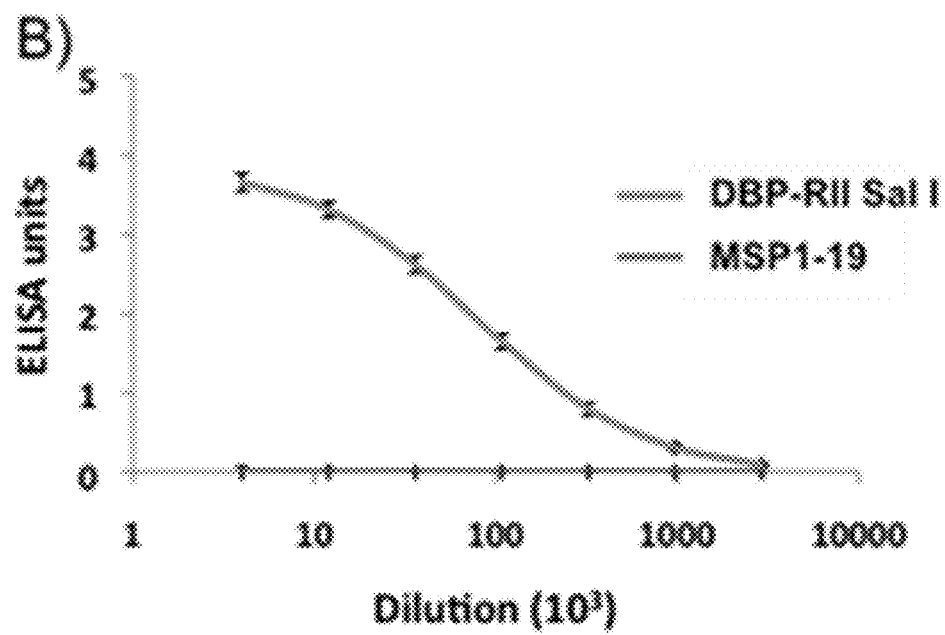
Figure 23C:
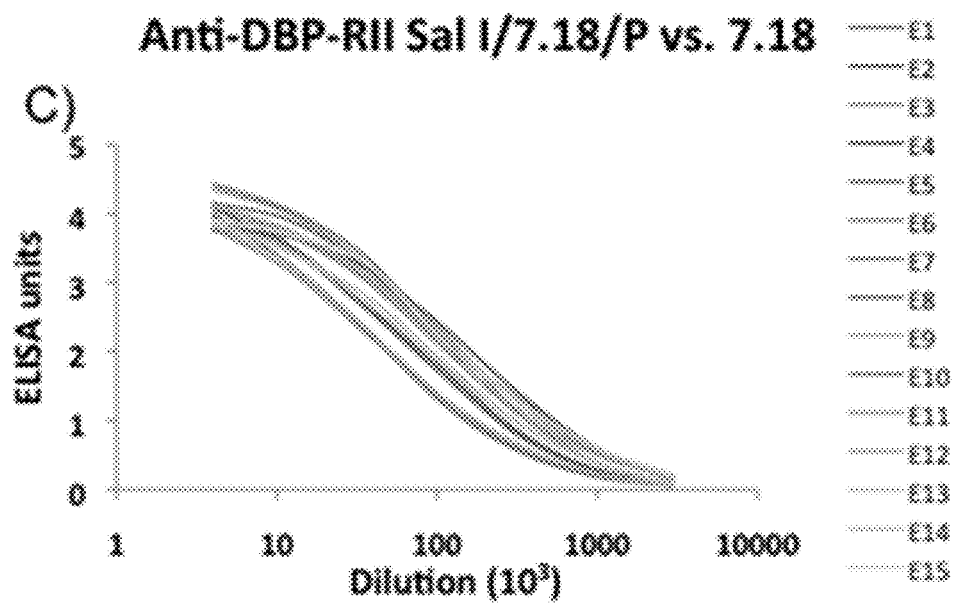
Figure 23D:
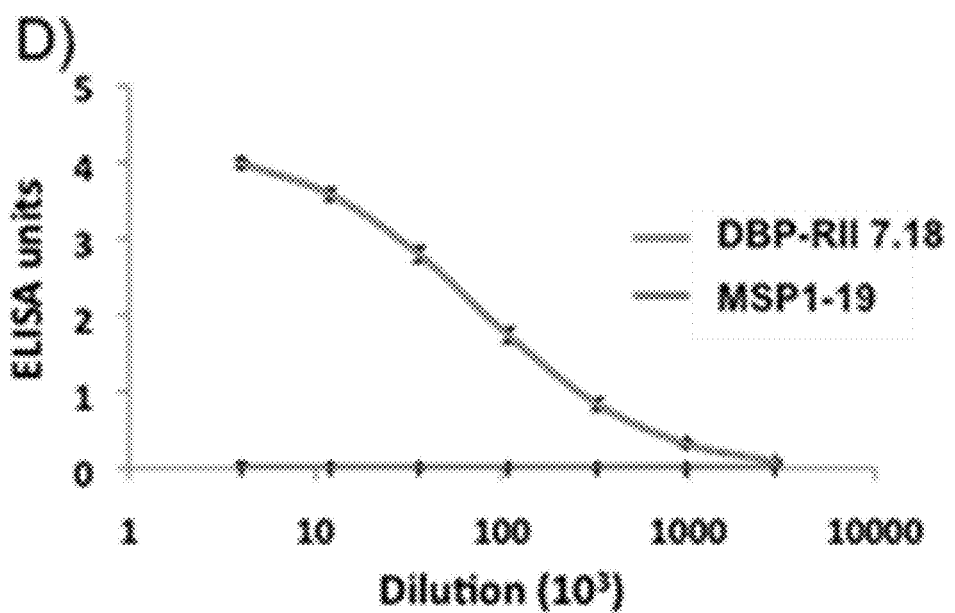
Figure 23E:
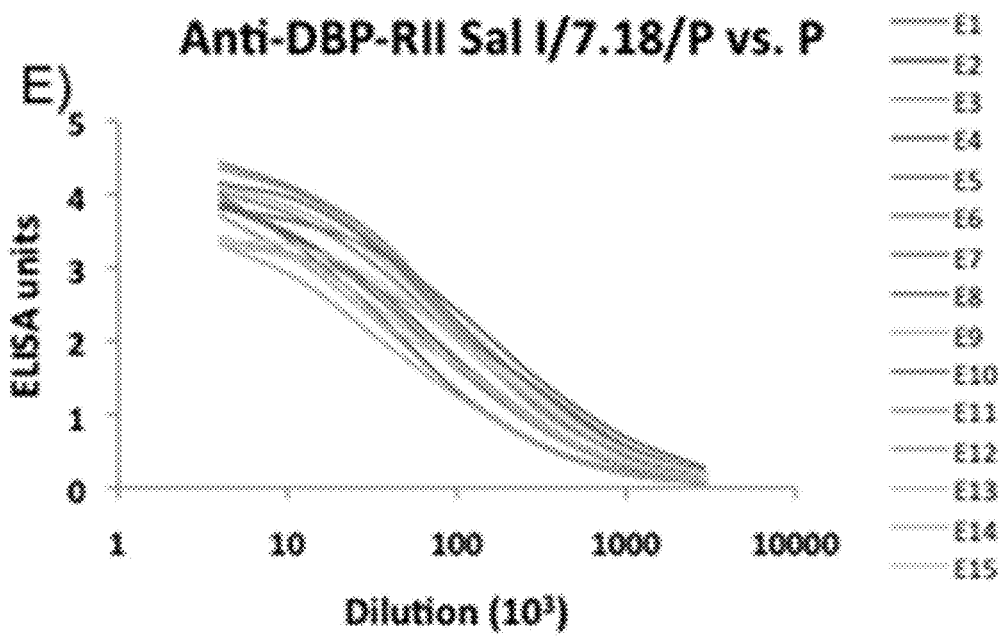
Figure 23F:
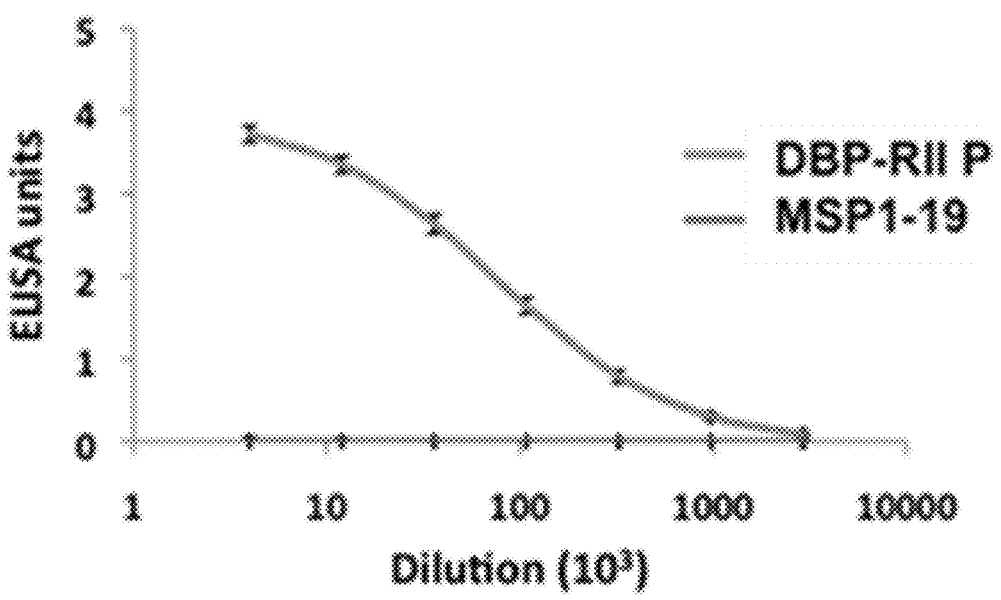

All PvDBP-RII cohorts produced a strong memory response upon anamnestic boost, as shown in FIGS. 16-18, 44A-44F. All PvDBP-RII DEKnull anamnestic responses were higher than with Sal $1^{Sal\ 1}$ immunization. Antibodies within each PvDBP-RII cohort had similar heterologous PvDBP-RII reactivity but differences were observed in antibody responses between cohorts (see FIG. 18). Anamnestic boost with a heterologous antigen resulted in a significantly stronger memory response than boosting with the homologous antigen (FIG. 18).

One aspect of the disclosure, therefore, encompasses embodiments of an engineered *Plasmodium vivax* Duffy Binding Protein (PvDBPII) having a modified region corresponding to an dominant immunogenic polymorphic B-cell epitopic region of a native PvDBPII, where the modified region has reduced immunogenic dominance when compared to the corresponding region of a native PvDBPII, and where the engineered PvDBPII can generate in a recipient animal or human subject an immune response having increased binding specificity for conserved Duffy binding epitopes of a *Plasmodium* Duffy Binding Protein when compared to an immune response generated by a natural PvDBPII variant.

In embodiments of this aspect of the disclosure, the dominant immunogenic polymorphic B cell epitopic region of the native PvDBPII can comprise an amino acid sequence having at least about 80% sequence similarity with the sequence DEKAQQRRKQWWNESK (SEQ ID No.: 3).

In embodiments of this aspect of the disclosure, the modified region of the engineered PvDBPII can have fewer polymorphic amino acids when compared to an dominant immunogenic polymorphic B-cell epitopic region of a native PvDBPII.

In embodiments of this aspect of the disclosure, the modified region of the engineered PvDBPII can have fewer polymorphic polar or charged residues when compared to an dominant immunogenic polymorphic B cell epitopic region of a native PvDBPII.

In embodiments of this aspect of the disclosure, the modified region of the engineered PvDBPII can comprise the amino acid sequence ASTAATSRTS (SEQ ID No.: 4).

In embodiments of this aspect of the disclosure, the modified region of the engineered PvDBPII can consist essentially of the amino acid sequence ASTAATSRTS (SEQ ID No.: 4).

In embodiments of this aspect of the disclosure, the amino sequence can have at least about 80% sequence similarity with the sequence SEQ ID No.: 2.

In embodiments of this aspect of the disclosure, the engineered PvDBPII can be expressed from a recombinant nucleic acid inserted into an expression vector.

In embodiments of this aspect of the disclosure, the recombinant nucleic acid can be codon optimized for expression of the PvDBPII in a genetically modified host cell.

Another aspect of the disclosure encompasses embodiments of a composition formulated for the generation in a recipient animal or human of an immune response, the composition comprising an engineered *Plasmodium vivax* Duffy Binding Protein (PvDBPII) having a modified region corresponding to an dominant immunogenic polymorphic B-cell epitopic region of a native PvDBPII, where the modified region can have reduced immunogenic dominance when compared to the corresponding region of a native PvDBPII, and where the engineered PvDBPII can generate in a recipient animal or human subject an immune response having increased binding specificity for conserved Duffy binding epitopes of a *Plasmodium* Duffy Binding Protein when compared to an immune response generated by a natural PvDBPII variant, and further comprising a pharmaceutically acceptable carrier.

In embodiments of this aspect of the disclosure, the pharmaceutical carrier can comprise an immunoadjuvant.

In embodiments of this aspect of the disclosure, the modified region of the engineered PvDBPII can have fewer polymorphic amino acids when compared to the corresponding dominant immunogenic polymorphic B-cell epitopic region of a native PvDBP In embodiments of this aspect of the disclosure, the modified region of the engineered PvDBPII can have fewer polymorphic polar or charged residues when compared to the corresponding dominant immunogenic polymorphic B-cell epitopic region of a native PvDBPII.

In embodiments of this aspect of the disclosure, the dominant immunogenic polymorphic B cell epitopic region of the native PvDBPII can comprise the amino acid sequence having at least about 80% sequence similarity with the sequence DEKAQQRRKQWWNESK (SEQ ID No.: 3).

In embodiments of this aspect of the disclosure, the modified region of the engineered PvDBPII can comprise the amino acid sequence ASTAATSRTS (SEQ ID No.: 4).

In embodiments of this aspect of the disclosure, the modified region of the engineered PvDBPII can consist essentially of the amino acid sequence ASTAATSRTS (SEQ ID No.: 4).

In embodiments of this aspect of the disclosure, the engineered PvDBPII can have an amino sequence having at least about 80% sequence similarity with the sequence SEQ ID No.: 2.

In embodiments of this aspect of the disclosure, the engineered PvDBPII can be expressed from a recombinant nucleic acid inserted into an expression vector.

In embodiments of this aspect of the disclosure, the recombinant nucleic acid can be codon optimized for expression of the PvDBPII in a genetically modified host cell.

Yet another aspect of the disclosure encompasses embodiments of a method of eliciting in an animal or human subject an immune response, comprising administering to the subject an immunogenic composition comprising an engineered *Plasmodium vivax* Duffy Binding Protein (PvDBPII) comprising a modified region corresponding to an dominant immunogenic polymorphic B-cell epitopic region of a native PvDBPII, where the modified region can have reduced immunogenic dominance when compared to the corresponding region of a native PvDBPII, and where the elicited immune response has increased binding specificity for conserved Duffy binding epitopes of a *Plasmodium* Duffy Binding Protein compared to an immune response generated by a natural PvDBPII.

In embodiments of this aspect of the disclosure, the immunogenic composition can comprise the engineered PvDBPII and an immunoadjuvant.

In embodiments of this aspect of the disclosure, the engineered PvDBPII can have fewer polymorphic amino acids when compared to an dominant immunogenic polymorphic B-cell epitopic region of a native PvDBPII.

In embodiments of this aspect of the disclosure, the dominant immunogenic polymorphic B-cell epitopic region of a native PvDBPII can comprise the amino acid sequence having at least about 80% sequence similarity with the sequence DEKAQQRRKQWWNESK (SEQ ID No.: 3).

In embodiments of this aspect of the disclosure, the modified region of the engineered PvDBPII can comprise the amino acid sequence ASTAATSRTS (SEQ ID No.: 4).

In embodiments of this aspect of the disclosure, the modified region of the engineered PvDBPII can consist essentially of the amino acid sequence ASTAATSRTS (SEQ ID No.: 4).

In embodiments of this aspect of the disclosure, the engineered *Plasmodium vivax* Duffy Binding Protein can comprise the amino sequence having at least about 80% sequence similarity with the sequence SEQ ID No.: 2.

Still another aspect of the disclosure encompasses embodiments of a method of eliciting in an animal or human subject an immune response, comprising administering to the subject an immunogenic composition comprising a combination of *Plasmodium vivax* Duffy Binding Protein (PvDBPII) variants, wherein the elicited immune response has increased binding specificity for conserved Duffy binding epitopes of a *Plasmodium* Duffy Binding Protein compared to an immune response generated by a single natural PvDBPII.

In embodiments of this aspect of the disclosure, the immunogenic composition can comprise the *Plasmodium vivax* Duffy Binding Protein (PvDBPII) variants Sal 1, 7.18, and P, or immunogenic fragments thereof.

In embodiments of this aspect of the disclosure, the immunogenic composition can comprise the *Plasmodium vivax* Duffy Binding Protein (PvDBPII) variants Sal 1, 7.18, and P, having the amino acid sequences according to SEQ ID NOs.: 1, 6, and 7, respectively.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure and protected by the following claims.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

EXAMPLES

Example 1

Design of DEKnull

Analysis of coding sequences of available in public databases for the *P. vivax* DBPII ligand domain region (PvDBPII) revealed that most polymorphic residues were polar or charged. The most highly variant residues of PvDBPII occurred in the center of the ligand domain and were previously identified to be part of a dominant Bc epitope having the amino acid sequence (DEKAQQRRKQWWNESK) (SEQ ID No.: 3) that was also a target of inhibitory antibody.

DBPII-Sal1 was used as a template to design the novel synthetic antigen, DEKnull in which the polar/highly charged residues 384D, 385E, 386K, 388Q, 389Q, 390R, 392K and 393Q within the dominant B-cell epitope (H3) identified from our previous study (Chootong et al., (2010) *Infect. Immun.* 78: 1089-1095) were replaced by 384A, 385S, 386T, 388A, 389T, 390S, 392T and 393S, respectively as shown in FIG. 1.

Figure 2C:
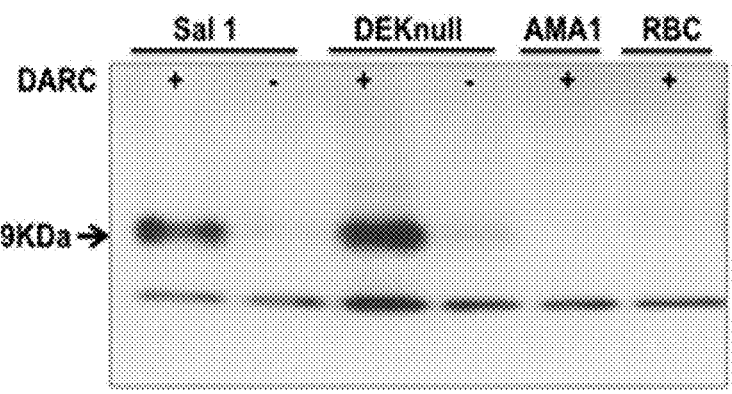
Figure 2B:
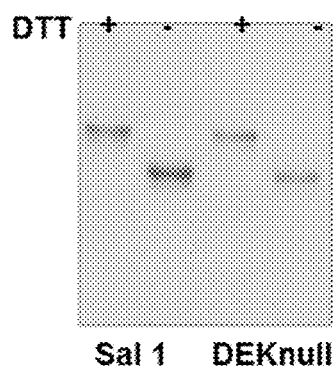

None of the residues mutated were critical for PvDBPII binding to erythrocytes. Recombinant proteins of DEKnull and PvDBPII were expressed in bacteria, purified from inclusion bodies and refolded by rapid dilution by the same protocol. Expression level and stability of the DEKnull product was similar to Sal1 and both refolded antigens migrated at expected size Of 30 kDa on SDS-PAGE (FIG. 2A). DEKnull and PvDBPII had similar sensitivity to the reducing agent DTT and a comparable mobility shift was observed with both refolded proteins (FIG. 2B).

Example 2

Cloning and Protein Expression

The nucleotide sequences encoding the ligand domain of *Plasmodium vivax* region II (PvDBP-RII) from three variants: DBPII-Sal 1, DBPII-7.18 and DBPII-P (accession numbers P22290 (SEQ ID NO.: 5), AAL79051.1 (SEQ ID NO.: 6), and AAL7907.3 (SEQ ID NO.: 7), respetively), the synthetic variant DEKnull (Ntumngia F B and Adams J H) as well as PvMSP1-19 were synthesized and codon-optimized for expression in *E. coli*. The synthetic genes were cloned into an expression vector, pET21a+(Novagen), containing a C-terminal histidine tag to facilitate purification by affinity chromatography. The resulting plasmids were transformed into BL21 (DE3) LysE *E. coli* (Invitrogen).

For the PvMSP1-19 construct, deletion mutagenesis was used to remove a highly hydrophobic GPI anchoring segment of the allele interfering with efficient expression. The primers used for the deletion mutagenesis were: 5'-CACCACCAC-CACCACCACTG-3' (SEQ ID No.: 5) and 5'-GCTA-CAAAAAACACCTTCAAACAGCG-3' (SEQ ID No.: 6). The deletion constructs were examined by restriction digest (confirming removal of the XhoI restriction site). All constructs were confirmed by sequencing. Constructs were transformed into the DH5a cloning cell line and glycerol stocks were made for future use.

Small Scale Expression

The pET21 constructs were transformed into BL21 (DE3) pLysE *E. coli* cells (Invitrogen, Cat # C6565-03) and single clones were chosen for small-scale pilot expression. Single clones were grown overnight at 37° C. in 2 mL of LB broth containing 50 ug/mL ampicillin. The 2 mL culture was then diluted 1:10 in LB broth containing 50 µg/mL ampicillin and grown for 2-3 hrs at 37° C. Samples were induced with 1 mM IPTG and grown for an additional 3 hrs. One mL samples were centrifuged and the cell pellet was heated at 65° C. for 5 min with 1 mL SDS-PAGE loading buffer. Ten µL samples were then separated by SDS-PAGE and, following transfer to nitrocellulose membrane, were probed with monoclonal antibody 3D10 and detected with HRP conjugated goat anti-mouse polyclonal IgG (KPL, Cat #04-18-06).

PvMSP1-19 Expression

Deletion mutagenesis was used to remove a highly hydrophobic GPI anchoring segment from the PvMSP1-19 construct interfering with efficient expression. Western analysis with an anti-His (C-term) monoclonal antibody from Invitrogen (Cat #46-0693) allowed detection of the deletion constructs in the presence or absence of the RigA plasmid (added to improve expression efficiency). Parasite genes in general (particularly, but not exclusively, *P. falciparum*) tend to have a codon bias. For *Plasmodial* species, this is due to the AT rich composition of their genomic DNA. Some codons commonly found in the parasite are rarely used by *E. coli*. The RigA plasmid encodes 3 tRNAs that are required for translation of certain rare codons. Co-transformation of RigA into the host *E. coli* allowed constitutive expression of these tRNAs and enhanced the overexpression of some recombinant parasite proteins. The PvMSP1-19 deletion constructs were used for large scale expression of the PvMSP1-19 antigen.

A pilot expression was carried out in shaker flask and frozen stocks of E. coli were stored at −80° C. An aliquot of frozen cells was used to set up an overnight starter culture. 250 ml of the starter culture was fed into a 7.5 L the bioreactor vessel (NewBrunswick) with 4 L of defined medium using a peristaltic pump and cells grown at 37° C. until a cell density of about 70 g/L was achieved. The temperature was then lowered to 23° C. and protein expression induced with IPTG at 1 mM final concentration for 3 hrs. The cells were harvested by centrifugation at 6000 rpm for 15 min and pellets stored at −80° C. until needed.

Expressed proteins were purified from inclusion bodies under denaturing conditions as described (Singh et al., (2001) *J. Biol. Chem.* 276: 17111-17116; Tran et al., (2005) *Cytometry* A63: 59-66; Yazdani et al., (2004) *Biotechnol. Lett.* 26: 1891-1895, incorporated herein by reference in their entireties) with modifications. Briefly, cells were re-suspended in pre-chilled lysis buffer (10 mM Tris buffer pH 8.0, 1 mM EDTA, 3% sucrose, 200 µg/ml lysozyme, 1 mM PMSF, 0.1 M NaCl, 20 µg/ml DNase), inclusion bodies recovered by centrifugation, washed two times (10 mM Tris-HCl, pH 8.0, 3 M Urea, 1 mM EDTA, 1 mM PMSF), solubilized (20 mM phosphate buffer, pH 7.8 containing 8 M Urea, 0.5 M NaCl) and recombinant proteins purified by Nickel Sepharose 6 affinity chromatography (GE Health). Eluted fractions were checked for purity by separation on SDS-PAGE. Fractions containing pure protein were pooled and refolded by rapid dilution as described by Singh et al., (2001) *J. Biol. Chem.* 276: 17111-17116. The refolded product was dialyzed against 50 mM phosphate buffer, pH. 6.5 containing 1 M Urea for 36 hrs with two buffer changes every 12 hrs. The dialyzed product was concentrated down, filtered through a 0.2 µm filter, dialyzed, adjusted to 1 mg/ml in PBS and stored at −80° C.

Endotoxin Removal from Purified Antigens

Endotoxins were removed from purified proteins using the Detoxi-Gel Endotoxin Removal Gel kit (Thermo Scientific), and the final endotoxin levels quantified by a Limulus Amebocyte Lysate (LAL) Assay using the ToxinSensor Chromogenic LAL Endotoxin Assay Kit (GenScript, N.J., USA), according to manufactures recommendations. Final protein concentrations were adjusted to 1 mg/ml and stored in aliquots at −80° C.

Purification of rPvMSP1-19

Recombinant PvMSP1-19 was expressed using the same protocol for rPvDBPII above but purified under native conditions since it was expressed as a soluble protein. Briefly, cell pellet was thawed from −80° C. on ice, resuspended in lysis buffer (10 mM Tris buffer pH 8.0, 1 mM EDTA, 3% sucrose, 200 ug/ml lysozyme, 1 mM PMSF, 0.1M NaCl, 20 ug/ml DNase) followed by brief sonication. The lysate was centrifuged at 15,000 rpm for 30 min at 4° C. and the supernatant collected, equilibrated in binding buffer (20 mM phosphate buffer, pH 7.8, 8M urea, 0.5M NaCl) for 15 mins. The equilibrated lysate was filtered through a 0.45 µm filter and protein purified by affinity chromatography using Nickel Sepharose 6 fast flow column (GE Health). The column was washed extensively with binding buffer containing 10 mM imidazole and bound protein eluted with binding buffer, containing 300 mM imidazole. Eluted fractions were separated on SDS-PAGE gel to check for purity and pure protein fractions were pooled and dialyzed against PBS.

Example 3

Functional Analysis of Refolded Antigens

Refolded antigens were tested for ability to bind Duffy positive human erythrocytes in an erythrocyte-binding assay. Duffy-positive erythrocytes treated with chymotrypsin were used as control. 20 µg of refolded antigens were incubated with previously washed erythrocytes or erythrocytes treated with chymotrypsin in PBS with 1% BSA for 4 hrs at room temperature. The reaction mixture was layered over silicone oil (Dow Corning) and centrifuged for 30 secs at 500×g. Bound antigen was eluted from cells with 300 mM NaCl. Eluted proteins in approximately 40 µl was diluted to 100 µl with SDS-PAGE buffer, heated at 65° C. for 3 mins and separated on SDS-PAGE. Bound antigens were detected by immunoblot analysis with MAb-3D10, an anti-DBPII specific monoclonal antibody. The antigens were tested for binding to human erythrocytes by flow cytometry as previously reported (Grimberg et al., (2007) PLoS Med 4: e33717, Tran et al., (2005) *Cytometry* A63: 59-66). Briefly, 3 µg of either antigen were incubated with 1 µl of Duffy-positive erythrocytes in 100 µl PBS with 1% BSA for 2 hrs at room temperature. Unbound antigen on red blood cells was washed off and erythrocytes incubated with a mouse anti-His monoclonal antibody conjugated to Alexa fluor 488 (Qiagen). After washing, cells were suspended in 300 µl of PBS with 1% BSA and 100,000 events were analyzed using an Accuri C6 flow cytometer on the FL 1 channel. Binding was quantified by measuring the mean fluorescent intensity (MFI) of each sample relative to cells without bound antigen serving as control.

Example 4

Antibody Production

Polyclonal antibodies were produced in rats by immunizing with purified refolded recombinant Sal1 and recombinant DEKnull. Rats in each group received 0.1 mg of either recombinant DEKnull or Sal1 emulsified in TITERMAX GOLD® three times, 3 weeks apart. Pre-immune sera were collected on day 0 and immune sera 3 weeks after last immunization. Serum samples were pooled within each group for analysis.

Animal Handling and Immunizations 6-8 weeks old female Balb/c mice were purchased from the Harlan-Animal Research Laboratories (Harlan Laboratories, Inc, USA). Six cohorts of 15 mice each were set up and about 100 ul of pre-immune sera collected from each mouse on Day 0. The first four cohorts were immunized with 25 µg/dose of recombinant Sal1, 7.18, P or rPvMSP1-19 respectively, while the fifth cohort received 25 µg/dose of a mixture (8.33 µg each) of recombinant Sal1/7.18/P on day 0. A sixth cohort of 10 mice (control) received adjuvant alone. All antigens were formulated in TITERMAX GOLD® in a 1:1 (v/v) ratio and 50 ul injected subcutaneously at the base of the tail of each mouse. Antigen formulations were prepared just before immunization. All mice were boosted 21 days post-primary immunization with 50 ul (25 µg/dose) of same antigen, formulated 1:0.5 (v/v) in same adjuvant. Mice were bled for final sera on day 42-post immunization and sera separated and stored in individual bar coded tubes at −20° C. until needed.

Example 5

Immunoassays

ELISA was used to quantify the anti-DBPII total IgG antibody titers in each serum sample for recombinant Sal1 and recombinant DEKnull. Wells of 96-well microtiter plates were coated incubated overnight at 4° C. with 200 ng of either recombinant DEKnull or recombinant Sal1 diluted in PBS. After washing away unbound antigens with PBS-T (0.05% V/V), antigen-coated wells were blocked with 5% skim milk in wash solution. In triplicate half log serial dilutions of each serum sample were added to wells and incubated with shaking for 2 hrs at room temperature. Plates were again washed and wells incubated for 90 mins with a phosphatase-conjugated goat anti-rat monoclonal antibody (KPL Inc., Md., USA), diluted 0.5 µg/ml in wash buffer. Wells were washed, bound antibodies were detected with an alkaline phosphatase substrate (PHOSPHO BLUE®, KPL Inc., USA) and absorbance readings measured at 630 nm on an automated microplate reader (Synergy II, Biotek Inc., USA). Antibody titer for each serum sample was determined as the reciprocal of the dilution required to give an absorbance of 1 ($OD_{630}$=1.0) in the same assay.

To determine the proportion of anti-DBPII antibodies specific to either recombinant Sal1 or DEKnull, plates were coated overnight with either recombinant Sal1 or recombinant DEKnull and blocked as described above. Each of the antisera was pre-incubated at a 1:4000 dilution with different concentrations of either soluble antigen for 2 hr before adding to the pre-coated and blocked wells. The soluble antigens were titrated 3-fold from 30 µg to 0.005 µg over 8 duplicate wells and the ninth sample well was left without soluble antigen. 100 µl of the appropriately diluted antiserum-soluble antigen was added to each of duplicate wells and incubated for two hours. Plates were developed as described above.

For immunoblot analysis, refolded and denatured forms of recombinant DEKnull and recombinant Sal1 were separated by SDS-PAGE and electrophoretically transferred onto nitrocellulose membranes (Millipore). Membranes were rinsed in wash buffer (PBS/0.05% Tween 20) and blocked in 5% skimmed milk in wash buffer overnight at 4° C. The membranes were rinsed in wash buffer and reacted with either 2.5 µg ml$^{-1}$ MAb-3D10 or rat antisera diluted 1:4000. After three washes, membranes were incubated in either HRP-conjugated goat anti-rat or goat anti-mouse monoclonal antibody (KPL Inc., Md., USA) at 0.5 µg ml$^{-1}$ in wash buffer. Bound antibody was then detected with ECL substrate (GE Healthcare).

Example 6

Inhibition of DBPII Binding to Human Erythrocytes by COS7 Assay

Functional DBPII was expressed on the surface of COS7 cells, using Herpes Simplex Virus signal and transmembrane targeting sequences, and with a C-terminal tag of GFP according to Chitnis et al., (1994) *J. Exp. Med.* 180: 497-506; McHenry et al., (2011) *PLoS One* 6:e20192; and Michon et al., (2000). *Infect. Immun.* 68: 3164-3171. The cloning of DBPII-Sal1 and DEKnull coding sequences into pEGFP-N1 plasmid (Clonetech) were as described in Chitnis et al., (1994) *J. Exp. Med.* 180: 497-506; Fraser et al., (1997) *Infect. Immun.* 65:2772-7; Michon et al., (2000) *Infect. Immun.* 68: 3164-3171; Michon et al., (2001) FEBS Lett. 495: 111-114; and Michon et al., (1998) Am. J. Trop. Med. Hyg. 59: 597-599, incorporated hereby reference in their entireties. DNA of each plasmid was purified using an endotoxin-free plasmid maxi kit (Qiagen). COS7 cells were transfected with 125 ng per well in a 24-well culture dish using lipofectamine 2000 reagent (Invitrogen) and inhibition assays were carried out 42 hrs post transfection. Each well incubated with a different dilution of antiserum for 1 hr at 37° C. before human erythrocytes (10% hematocrit) were added to each well and incubated for another 2 hrs. Non adherent cells were washed off with PBS containing $Ca^{2+}$, $Mg^{2+}$ and binding quantified by counting rosettes observed in 30 microscope fields at 200× magnification. Binding inhibition of each antiserum was determined by accessing the percentage of rosettes in wells of transfected cells in the presence of antisera relative to wells with transfected cells in the presence of pre-immune sera.

Example 7

DEKnull Erythrocyte Binding Activity

Figure 2D:
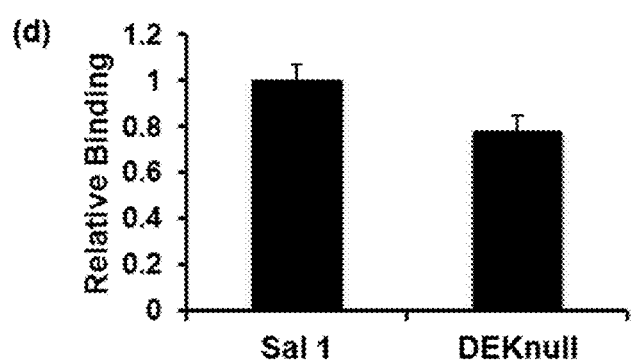

The purified refolded DEKnull was tested by two standard in vitro assays for binding specificity to Duffy antigen surface receptor on human erythrocytes. In a modified version of the original erythrocyte binding assay used to validate erythrocyte receptor specificity of malaria parasite ligands, purified refolded DEKnull and PvDBPII in isotonic buffer were tested for specificity of binding to Duffy positive erythrocytes and Duffy negative erythrocytes. Both recombinant proteins strongly bound to Duffy positive erythrocytes while only trace amounts of each recombinant protein could be detected eluted from Duffy negative erythrocytes. No bands of expected size were observed in lanes with erythrocytes incubated with *P. falciparum* AMA1 or control lanes with erythrocytes alone (FIG. 2C). Demonstration of binding of refolded DEKnull and PvDBPII to erythrocytes was repeated by a flow cytometry erythrocyte-binding assay that can quantify binding (37). With this assay we confirmed there was no significant quantitative difference in binding to Duffy positive erythrocytes between recombinant DEKnull and PvDBPII (FIG. 2D).

Example 8

Testing Immunogenicity of DEKnull

Figure 3A:
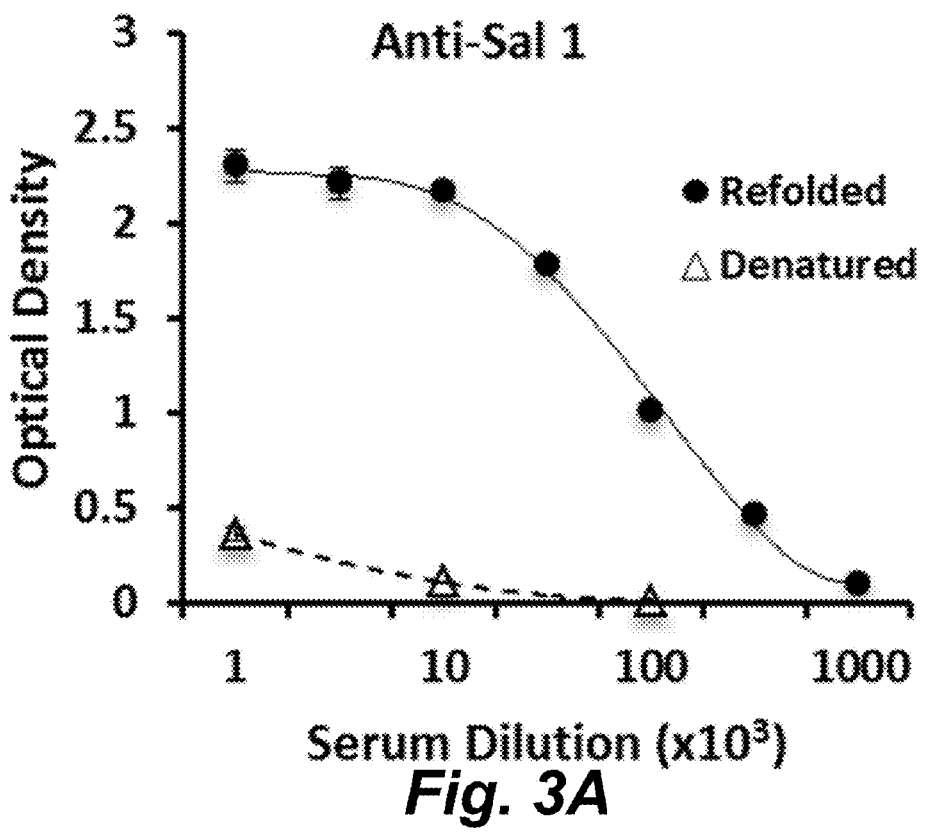
FIGS. 3A and 3B are graphs illustrating the reactivity of rat anti-Sal1 and anti-DEKnull sera with recombinant antigens. Antisera raised in rats against recombinant DBPII-Sal1 (FIG. 3A) and recombinant DEKnull (FIG. 3B) were tested by end point dilution for reactivity with homologous refolded (solid lines) and denatured (broken lines). Antigens preparations were adsorbed onto wells of a micro titer plate and allowed to react with different dilutions of the antisera. Each point on the curves represents the mean of triplicate wells, while error bars represent±standard deviation.
Figure 3B:
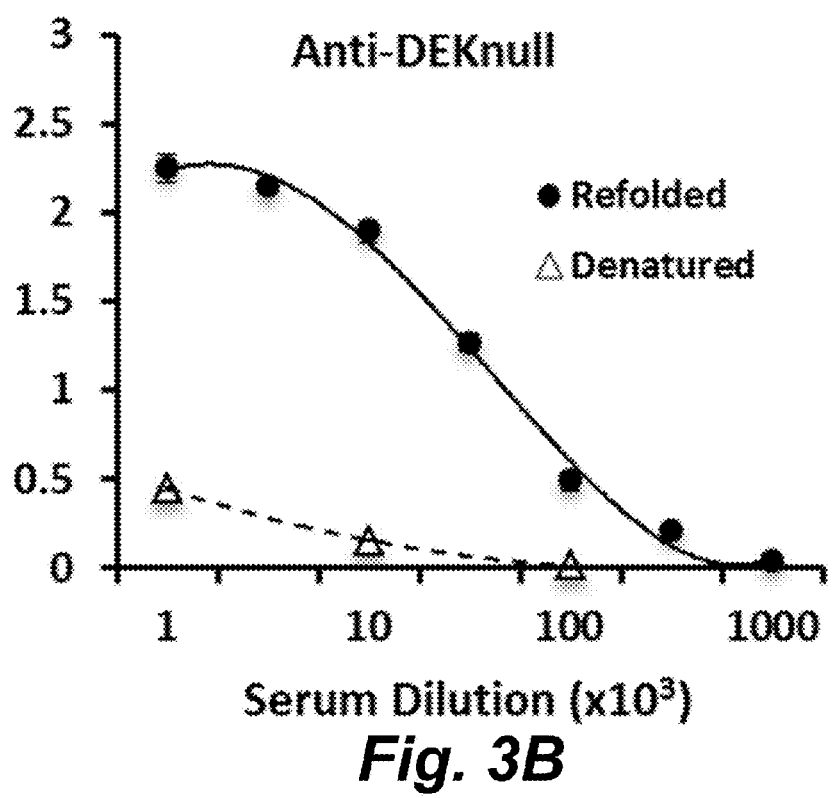

Serologic response to recombinant DEKnull was compared to recombinant Sal1 by laboratory immunizations of rats to evaluate the effect of the loss of the dominant Bc epitope in DEKnull. Immunogenicity was determined by ELISA end point titration reactivity against each homologous recombinant protein (FIGS. 3A and 3B).

Figure 4A:
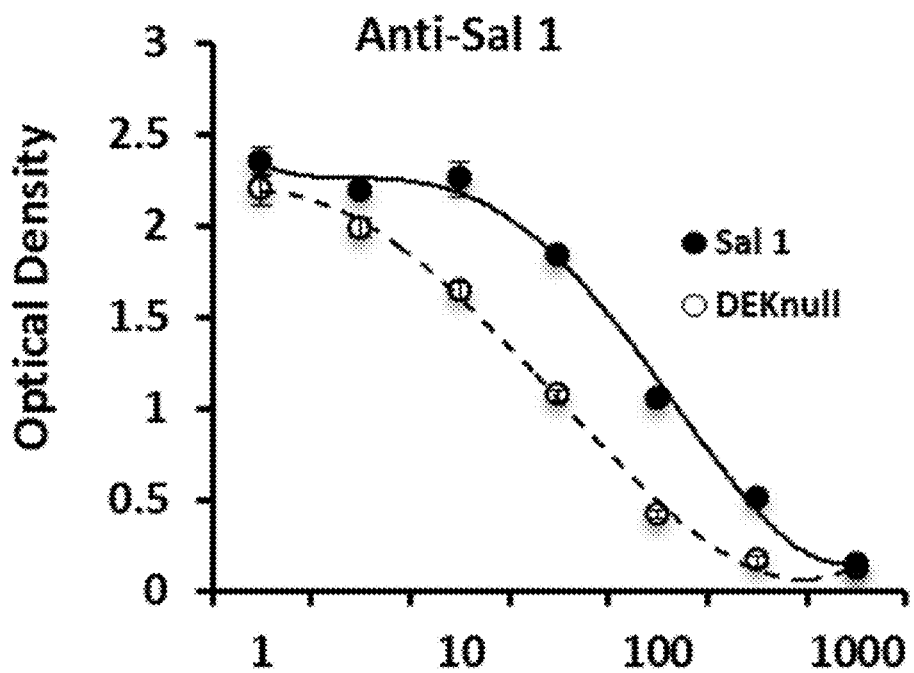
FIGS. 4A and 4B are graphs illustrating the reactivity profiles of anti-Sal1 and anti-DEKnull sera with recombinant antigens. Each antiserum was tested by end point dilution for cross reactivity with homologous and heterologous refolded antigens. Antigens preparations were adsorbed onto wells of a micro titer plate and allowed to react with different dilutions of the antisera. Solid and broken lines represent recombinant Sal1 (FIG. 4A) and recombinant DEKnull (FIG. 4B), respectively. Each point on the curves represents the mean of triplicate wells, while error bars represent±standard deviation.
Figure 4B:
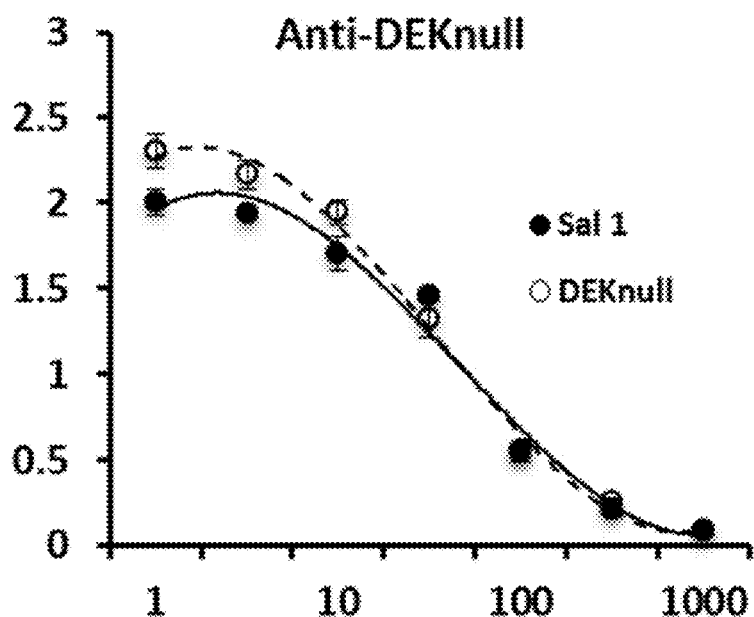

DEKnull appeared equally immunogenic to Sal1 in the rats, inducing high levels of anti-DBPII antibodies. In the same way, each antiserum had a strong bias towards reactivity to conformational epitopes. Comparing reactivity of anti-DEKnull and anti-PvDBPII sera to refolded and reduced homologous antigens demonstrated approximately 86% of the antibodies reacted to refolded antigens versus reduced homologous antigens (FIGS. 3A and 3B). Anti-DEKnull serum reacted to the same level with both antigens at an end point antibody titer of 1:65,000, while in contrast anti-Sal1 reactivity was significantly different (P<0.005) for the two antigens at 1:100,000 and 1:68,000 for recombinant Sal1 and recombinant DEKnull, respectively (FIGS. 4A and 4B).

Figure 5A:
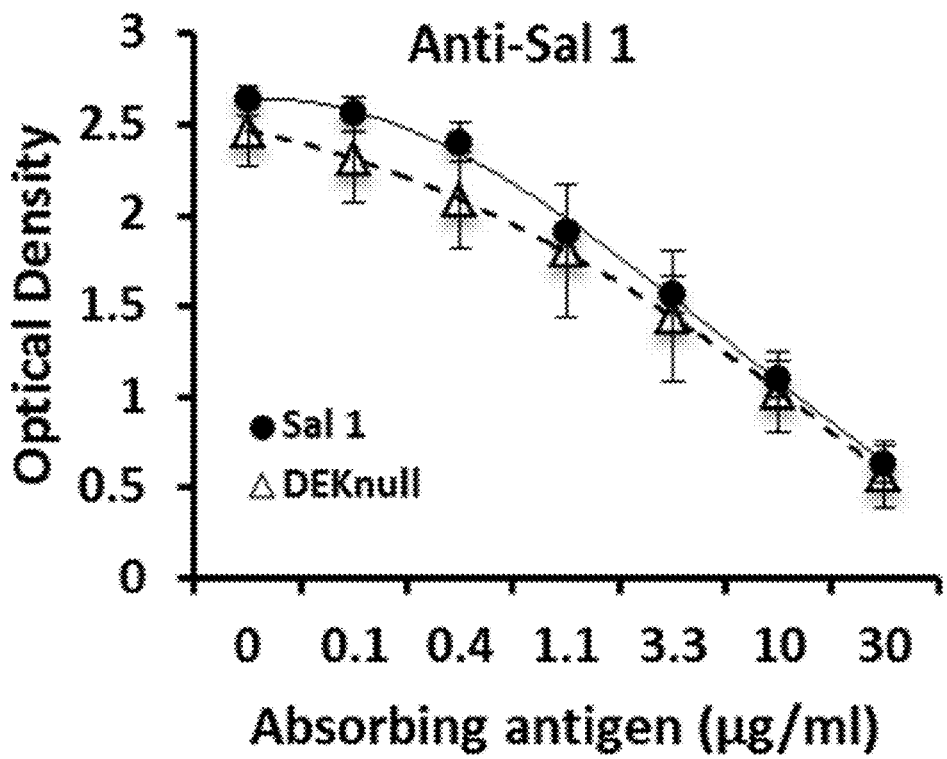
FIGS. 5A and 5B are graphs illustrating the proportion of cross-reacting and strain-specific antibodies. Antibodies specific for each antigen were pre-absorbed with either soluble recombinant DBPII-Sal1 (FIG. 5A) or recombinant DEKnull (FIG. 5B) prior to adding to antigen coated and pre-blocked wells. Curves represent averages of two independent assays and error bars represent±standard deviation of two independent experiments done in triplicate.
Figure 5B:
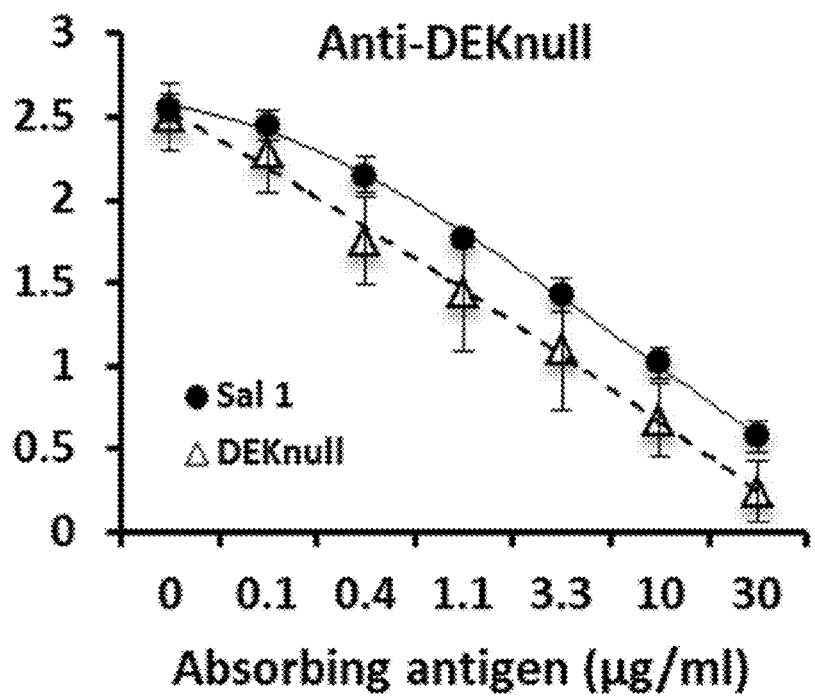

Further analysis using pre-absorption studies were conducted to determine the proportion of cross-reacting and strain-specific antibodies induced against either antigen. Antibodies specific to each antigen were depleted by incubating each antisera at a fixed dilution (1:4,000) with different concentrations of each soluble antigen before adding to the antigen pre-coated plates, prepared with either recombinant Sal1 or DEKnull as capture antigen. Although the reactivity of both antisera was higher when reacted to Sal1 antigen, the reactivity differences between each depleted polyclonal antisera were not significant (FIGS. 5A and 5B).

Example 9

Anti-DBPII Inhibition

Figure 6:
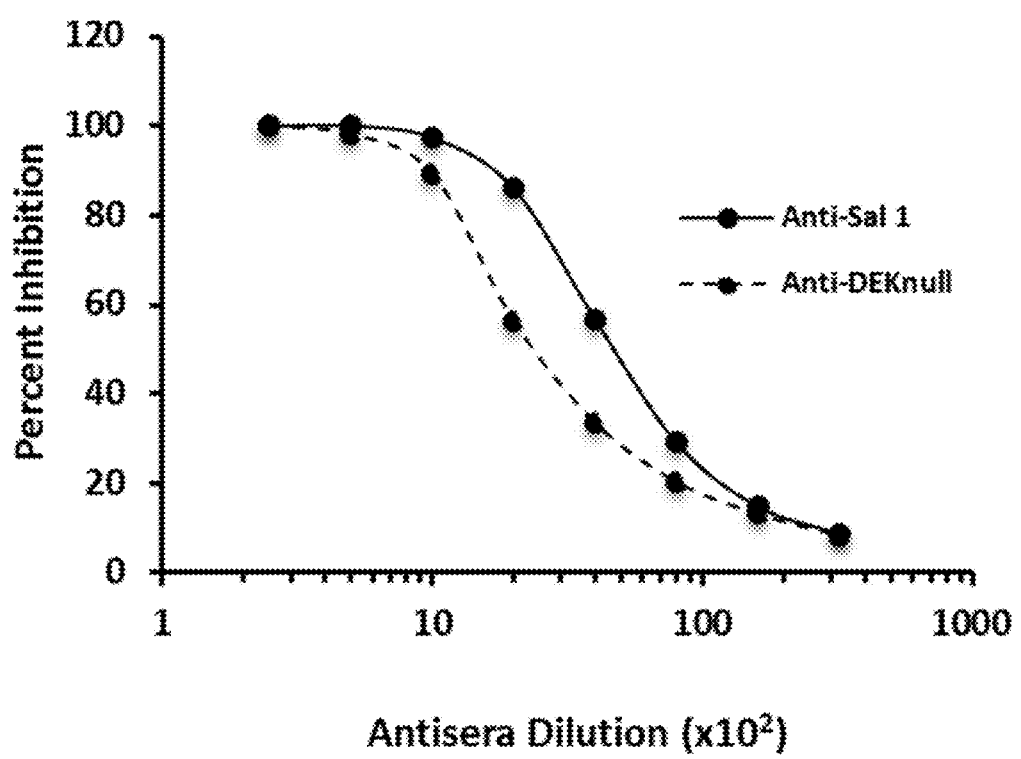
FIG. 6 is a graph illustrating the inhibition of erythrocyte binding to DBPII-Sal1 expressed on surface of COS7 cells by rat anti-DBPII-Sal1 and anti-DEKnull. A monolayer culture of COS7 cells expressing recombinant Sal1 on the cell surface was tested for binding to Duffy blood group antigen on human erythrocytes in the presence of anti-DEKnull and anti-Sal1 sera. Antibodies were tested by end point dilution and percent inhibition was quantified by comparing the number of rosettes bound to COS7 cells in 30 microscope fields (×200) in the presence test sera and pre-immune sera. Curves represent mean of three independent experiments done in duplicate. Error bars represent±standard deviation.
Figure 7:
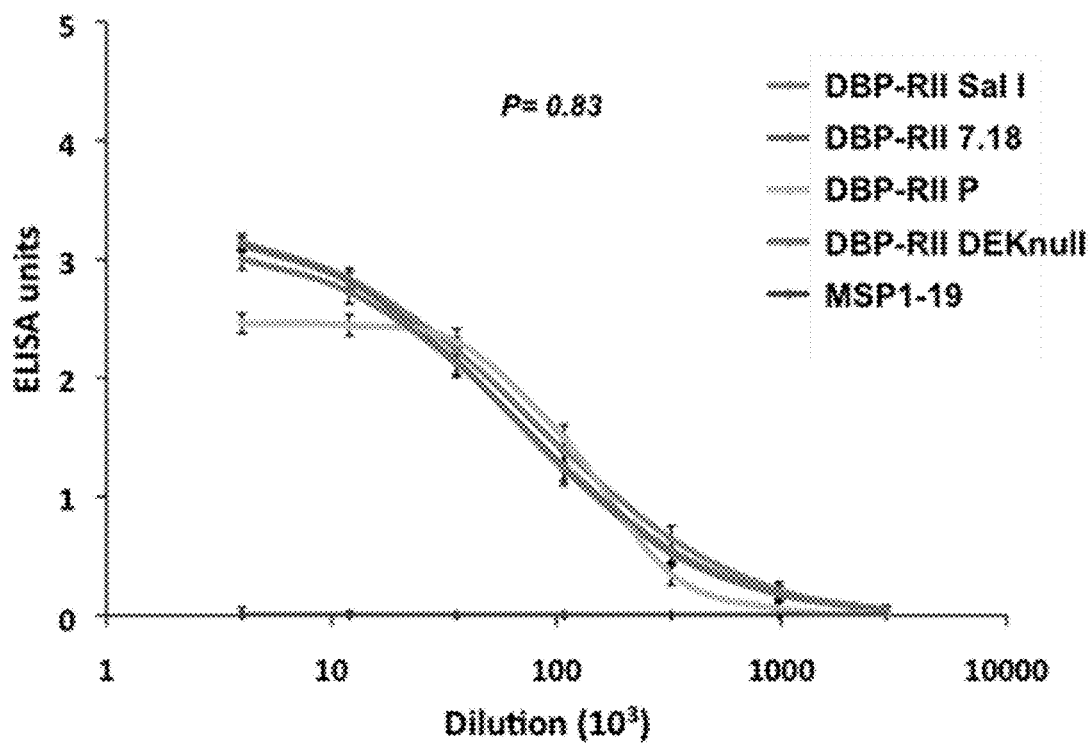
FIG. 7 is a graph illustrating an assessment of cross-reactivity of anti-PvDBP-RII Sal 1 sera against heterologous antigens. Individual mouse sera were assessed by ELISA for their reactivity to the heterologous PvDBP-RII antigens and logistic regression curves were plotted showing the reactivity of the entire cohort against each PvDBP-RII antigen and the PvMSP1-19 negative control antigen. Anti-PvDBP-RII Sal 1 sera reacts equally well to all of the PvDBP-RII antigens (p=0.83).
Figure 8:
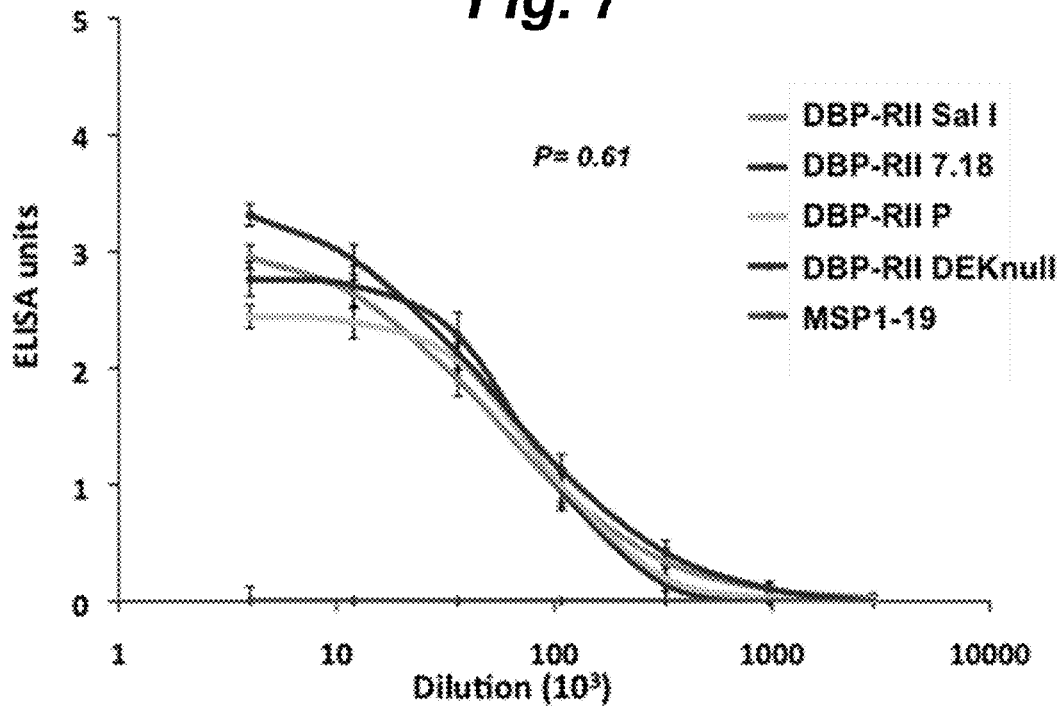
FIG. 8 is a graph illustrating an assessment of cross-reactivity of anti-PvDBP-RII 7.18 sera against heterologous antigens. Individual mouse sera were assessed by ELISA for their reactivity to the heterologous PvDBP-RII antigens and logistic regression curves were plotted showing the reactivity of the entire cohort against each PvDBP-RII antigen and the PvMSP1-19 negative control antigen. Anti-PvDBP-RII 7.18 sera reacts equally well to all of the PvDBP-RII antigens (p=0.61).
Figure 9:
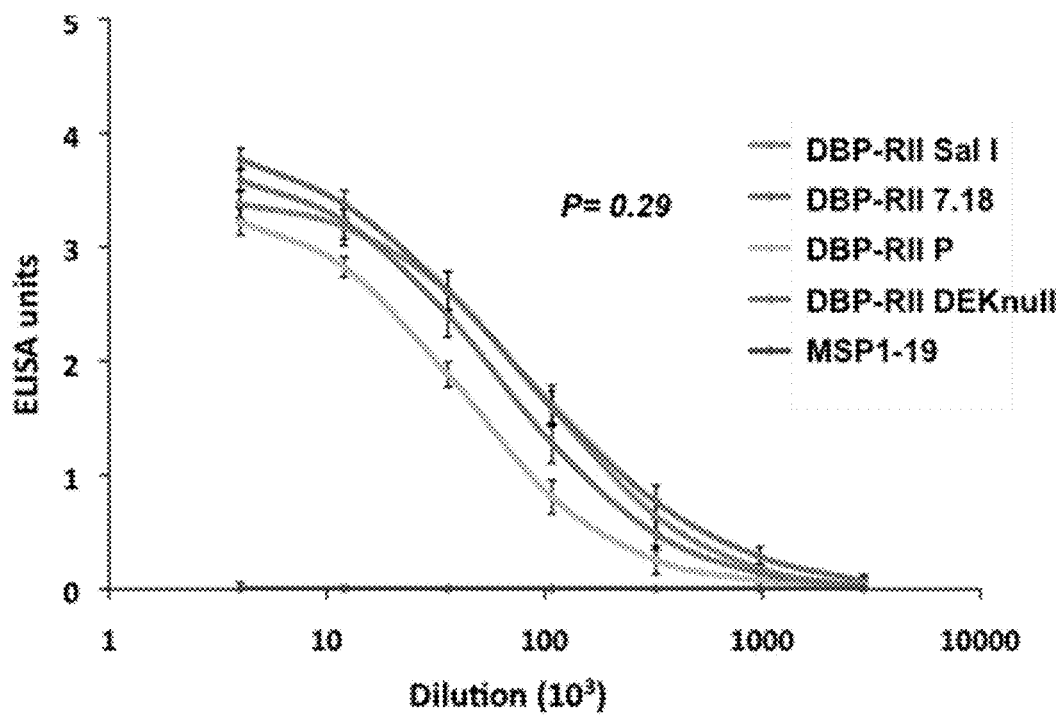
FIG. 9 is a graph illustrating an assessment of cross-reactivity of anti-PvDBP-RII P sera against heterologous antigens. Individual mouse sera were assessed by ELISA for their reactivity to the heterologous PvDBP-RII antigens and logistic regression curves were plotted showing the reactivity of the entire cohort against each PvDBP-RII antigen and the PvMSP1-19 negative control antigen. Anti-PvDBP-RII P sera reacts equally well to all of the PvDBP-RII antigens (p=0.29).
Figure 10:
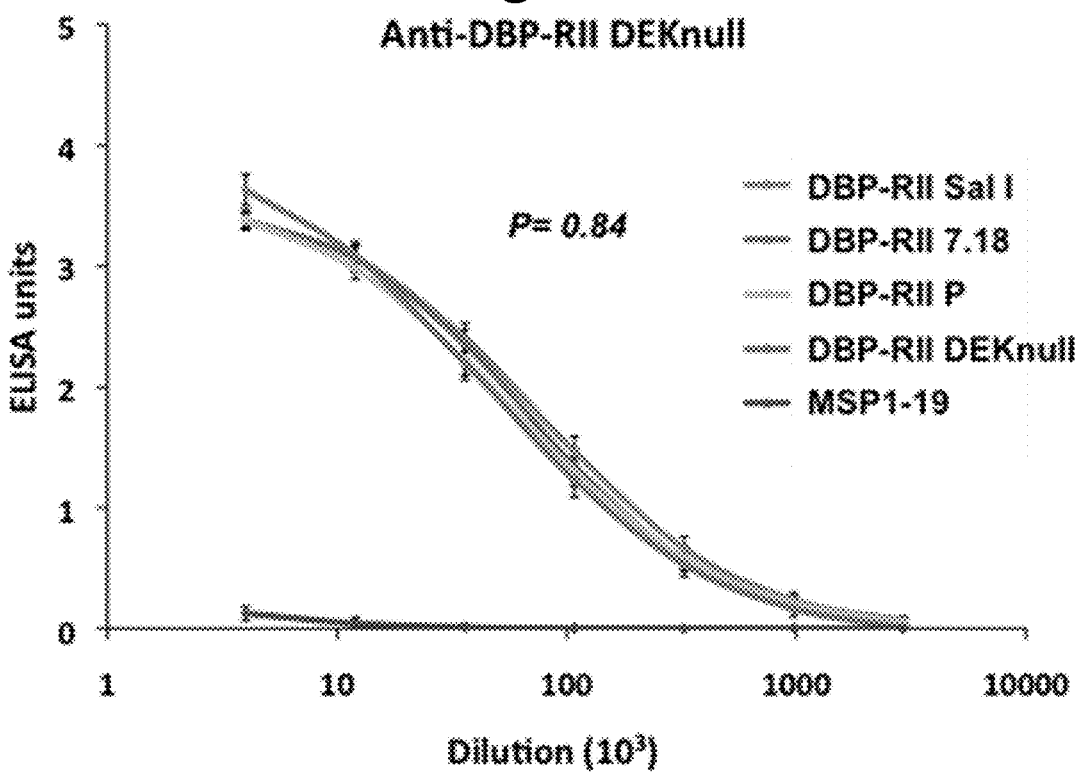
FIG. 10 is a graph illustrating an assessment of cross-reactivity of anti-PvDBP-RII DEKnull sera against heterologous antigens. Individual mouse sera were assessed by ELISA for their reactivity to the heterologous PvDBP-RII antigens and logistic regression curves were plotted showing the reactivity of the entire cohort against each PvDBP-RII antigen and the PvMSP1-19 negative control antigen. Anti-PvDBP-RII DEKnull sera reacts equally well to all of the PvDBP-RII antigens (p=0.84).
Figure 11:
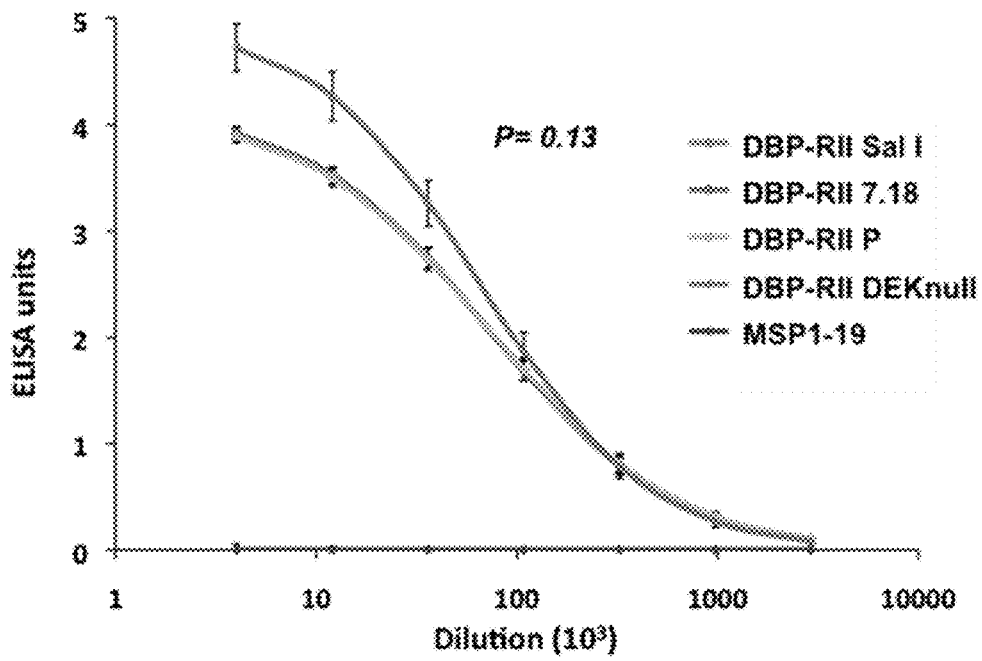
FIG. 11 is a graph illustrating an assessment of reactivity of anti-PvDBP-RII Sal 1/7.18/P sera against individual antigens. Individual mice serum samples were assessed by ELISA for their reactivity to the PvDBP-RII antigens and logistic regression curves were plotted showing the reactivity of the entire cohort against each PvDBP-RII antigen and the PvMSP1-19 negative control antigen. Anti-PvDBP-RII Sal 1/7.18/P sera reacts equally well to all of the PvDBP-RII antigens (p=0.13).

A standardized in vitro cell-based assay, which is used to evaluate erythrocyte-binding activity of PvDBPII and other Plasmodium ligands, provides a useful platform to measure anti-PvDBPII inhibition. Comparative effects of different antibodies can be evaluated against DBPII-erythrocyte binding by calculating 50% inhibitory concentration ($IC_{50}$) of each test antiserum, which is achieved by determining the inhibitory effects of serial dilutions ranging from 0 to 100% inhibition. Pre-immune sera tested at 1:1,000 showed no inhibition of binding and served as control for the experiments. As anticipated the antisera to DEKnull and PvDBPII were observed to inhibit DBPII-erythrocyte binding in a concentration dependent manner (FIG. 6). The $IC_{50}$ titer for anti-Sal1 at 1:5,000 was significantly more inhibitory than anti-DEKnull at 1:3,500 ($P<0.006$). This result confirms that the DEKnull epitope comprises a significant target of anti-DBPII inhibitory antibody but other more conserved epitopes also exist on DBPII.

Example 10

Western Blot Analysis

Antigens were separated on SDS-PAGE, transferred onto nitrocellulose membranes. Membranes were incubated in blocking buffer (PBS/5% Skimmed milk/0.05% Tween-20) overnight at 4° C. The next morning, membranes were rinsed in wash buffer (PBS/0.05% Tween-20) and incubated 2 hrs at room temperature with MAb-2D10 (anti-DBPII conformation dependent monoclonal antibody) diluted in blocking buffer. The membranes were rinsed in wash buffer before washing 3 times, 5 mins each with the same buffer. Membranes were incubated for 90 mins at room temperature in goat anti-mouse HRP conjugated secondary antibody (KPL) diluted 1:3000 in blocking buffer. All incubations were done on a rocker. After 3 washes, bound antibody was then detected with ECL substrate (GE Healthcare Life Sciences, USA).

Example 11

Expression and Refolding of Recombinant Antigens

Figure 49B:
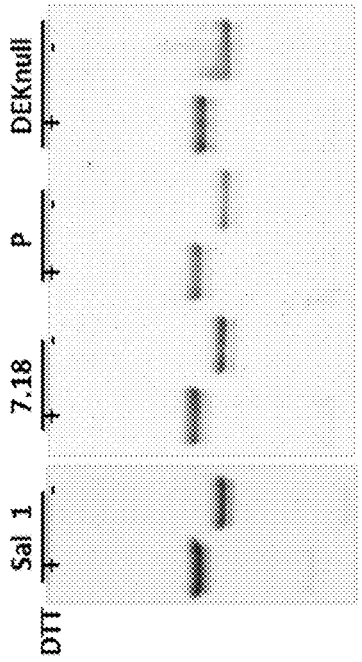
FIGS. 49A-49D are a series of digital images illustrating the purification, refolding, and functional analysis of rDBPII.
Figure 49D:
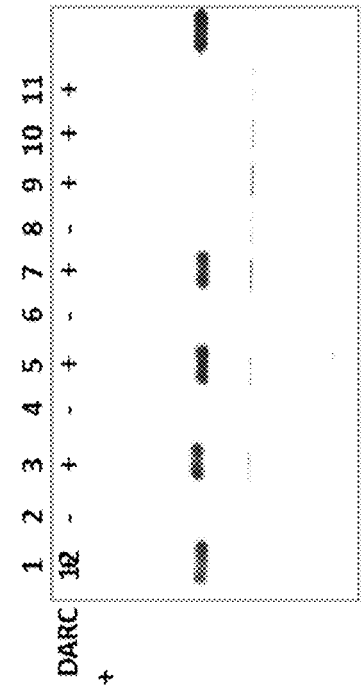
Figure 49A:
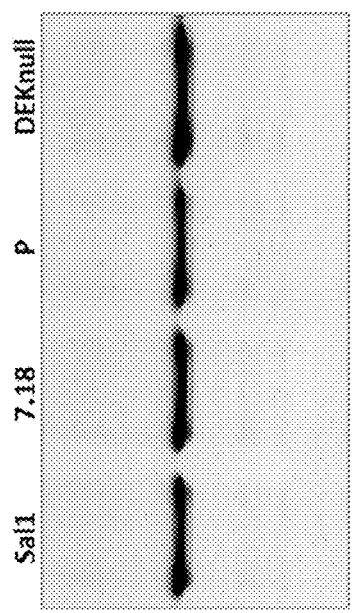
Figure 49C:
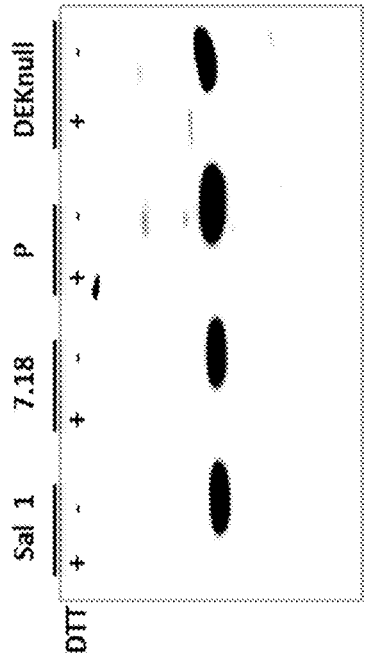

Recombinant PvDBP-RII proteins were purified to homogeneity from inclusion bodies under denaturing conditions by affinity chromatography. Purified antigens were refolded by rapid dilution and the refolded antigens were observed to move as a single band of 39 kDa on SDS-PAGE gel as expected. (FIG. 49A). Endotoxin levels in the purified antigens were determined by LAL assay and the final preparations contained less than ≤5EU per 100 μg of protein. A mobility shift was observed between refolded and denatured antigens on SDS-PAGE, a simple indicative of the presence of disulfide linkages and native conformation in the refolded antigens (FIG. 49B). Conformational structure of the purified antigens was confirmed by ELISA and Western analysis (FIG. 49C), by reactivity of the refolded but not the reduced antigens with MAb-2D10, previously demonstrated to specifically react only with conformational dependent epitopes in DBPII. A standard erythrocyte-binding assay was used to validate functionality and confirm native conformation of the purified proteins. The refolded antigens bound to Duffy-positive erythrocytes, but not to Duffy-negative cells (FIG. 49D). No binding was observed with PvMSP1-19, PfAMA1 and erythrocytes without bound antigen, which served as controls. This suggested that the antigens were correctly refolded, functionally active, with conformation similar to that of the native antigen.

Example 12

Immune Response of Mouse Anti-DBPII Antibodies to rDBPII

Three naturally occurring PvDBP-RII antigens (PvRII-Sal1, PvRII-7.18, and PvRII-P) and one synthetic PvDBP-RII antigen (DEKnull) were used to immunize mice to examine several different immunization strategies. Immunization with the synthetic DEKnull variant was compared to immunization with the individual naturally-occurring variants and also to immunization with a combination of the three naturally occurring variants (Group 1 mice). In addition, some mice were primed with two injections of the synthetic variant, followed by a third injection with a naturally occurring variant to determine if the natural variant was capable of generating a memory response in the immunized mice (Group 2 mice). The resulting reagents from Group 1 mice were tested for immunogenicity and cross reactivity in ELISAs and also for functional inhibition in the COS7 (green monkey kidney epithelial) cell erythrocyte-binding assay. Antisera from Group 2 mice were tested by ELISA to detect a memory response due to the anamnestic boost.

Figure 51:
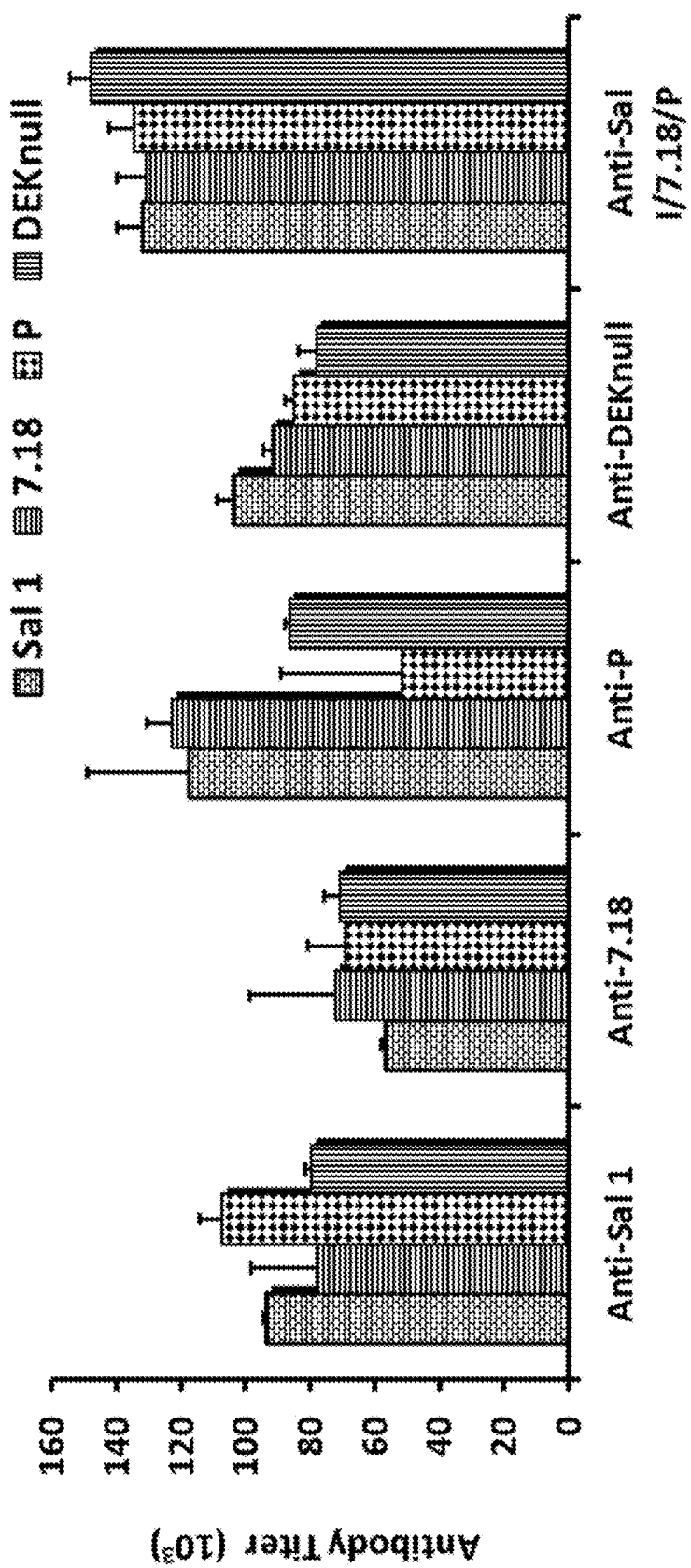
FIG. 51 is a bar graph illustrating IgG antibody responses in mice immunized with refolded rDBPII. Antiserum from individual mice from each group (n=15) were tittered by end point dilution against each antigen on plate. All OD values were converted to ELISA Units (EU) by normalizing against the OD of a standard. Antibody titers were determined from a regression curve for each immunization group at EU=1.5. The bars represent the ELISA titers for each immunization group against the different antigens. Error bars represent the standard deviation. Anti-MSP1-19 antiserum and rMSP1-19 served as negative control antiserum and antigen respectively

The immunogenicity of recombinant Sal1, 7.18, P and DEKnull was evaluated in BALB/c mice. Separate groups of mice were immunized simultaneously with either recombinant DEKnull, Sal1, 7.18, P or a combination of Sal1/7.18/P formulated in TiterMax gold. Control groups were immunized with rPvMSP1-19 or PBS/adjuvant alone. The specificity of binding and total IgG titers of each individual antisera was measured by ELISA against homologous antigens as well as cross reactivity with the heterologous antigens used in the immunization. All the single as well as the multiple variant immunization protocols produced high levels of anti-DBPII IgG responses in the mice against both homologous and heterologous antigens but no anti-DBPII response observed with the antisera against PvMSP1-19 and pre-immune sera as expected (FIGS. 50A-50E). Antibody titers at EU=1.5 was used as a quantitative measure for comparing the immune responses elicited by the mice against the various antigens (FIG. 51). The mixed variant vaccination strategy induced a significantly higher antibody response to all the individual antigens than the single variant vaccination and the level of antibody reactivity was the same for all the individual antigens used in the combination and also DEKnull, suggesting that a higher proportion of antibodies were produce to common epitopes in the mixed variant immunization compared to single variant immunization. With the exception of 7.18, there was no significant difference in the level of antibody response induced by the single variant immunization. Though not from a natural variant, anti-DEKnull reacted equally well with all the natural variants, and the level of antibody responses was similar to that of the naturally occurring variants, with the same level of antibody responses observed for both anti-DEKnull and the single variant vaccines.

Example 13

Functional Assessment of the Anti-DBPII Antibodies by COS7 Cell Assay

To assess the functional properties of the anti-DBPII antibodies raised in the mice against the various antigens, we measured the capacity of pool sera from each group to inhibit DBPII binding to DARC on the surface of human erythrocytes in a COS7 cell assay. Each antiserum titrated by end point dilution (100% to 0% binding inhibition range) was incubated with wells of transfected COS7 cells expressing five naturally occurring DBPII variants, two of which were not used for immunization (Table 3). There was a concentration dependent inhibition of erythrocyte binding with all tested antisera, with 100% inhibition observed at 1:500 and no inhibition observed with anti-PvMSP1-19 anti-sera at 1:1000. The reciprocal dilution of antisera that gave a 50% inhibition of binding ($IC_{50}$) to each DBPII variant was used as a quantitative measure for comparing anti-DBPII binding inhibitory responses against the different COS7 expressed variants by the Wilcoxon rank test (FIGS. 40A-40E).

Figure 52:
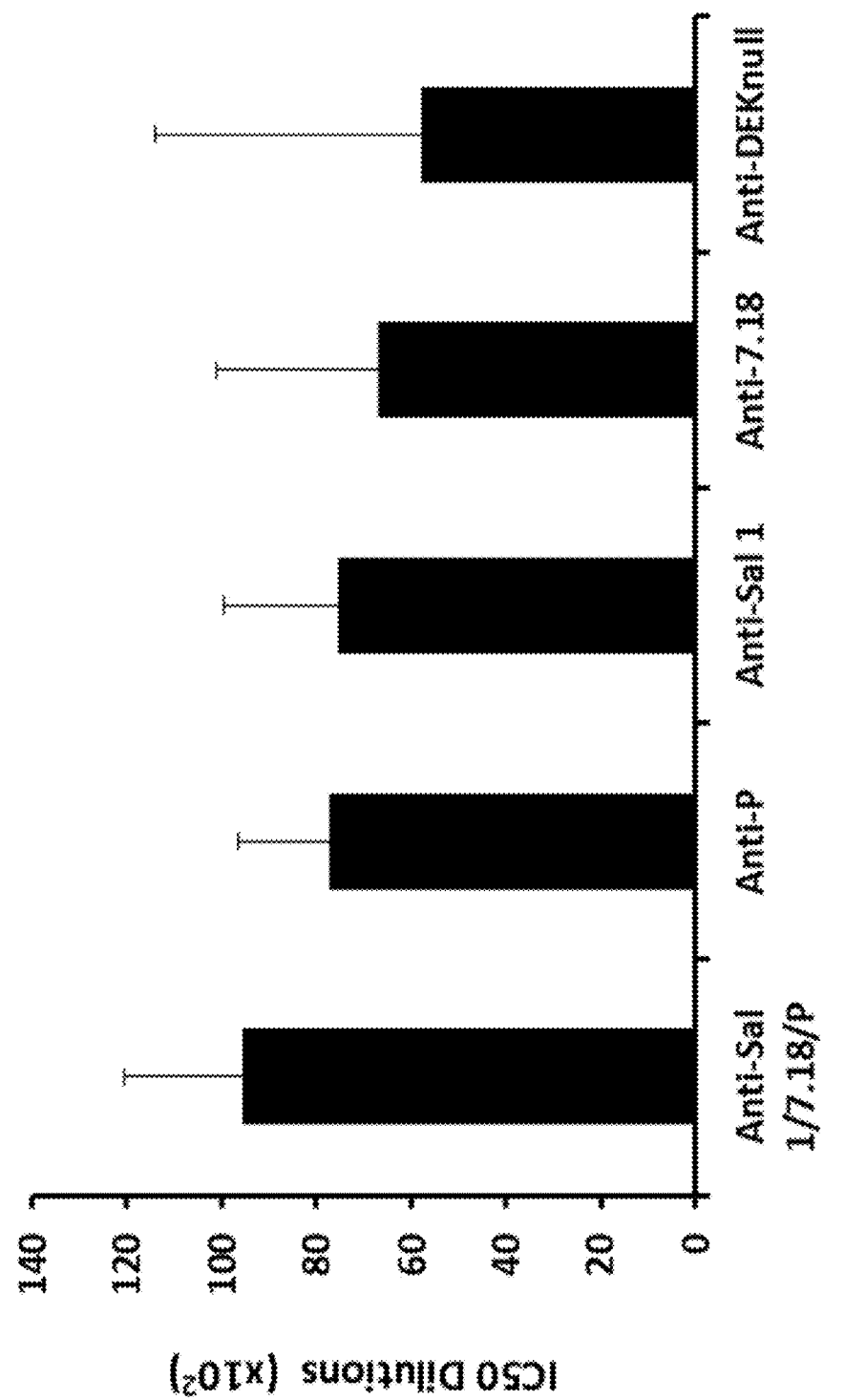
FIG. 52 is a bar graph illustrating a multiple comparison of anti-DBPII binding inhibitory response. The overall inhibitory responses of each antisera against all five COS7 expressed variants was compared with Benferroni multiple comparison adjustment. Bars represent the mean IC50 dilution of each antisera against all the natural isolates tested in the COS7 assay. Asterisk (*) indicates that compared to all the single variant antisera, there is a significant difference in binding inhibitory response between the mixed variant antisera and the 7.18 and DEKnull antisera. (P=0.05).

The inhibitory patterns seemed to classify the different variants into three antigenic groups: 7.18, AH, P in one group, then 27.16 and Sal1 in separate groups. Antibodies induced by the multiple variant immunization were skewed more towards a Sal1 inhibitory response, followed by P and then 7.18. Anti-DEKnull induced a lower but more consistent inhibitory response to all variants except with Sal1. There were significant differences in anti-DBPII inhibitory responses to the different antigens but no significant differences in inhibitory response observed between the single variant and the mixed variant vaccines. However, a multiple comparison test (Wilcoxon rank test with Benferroni multiple comparison adjustment) demonstrated that the multiple variant immunization strategy overall produces a broader binding-inhibitory antibody response, even to variants not included in the vaccine (FIG. 52). Quantitative analysis of both the ELISA and the in vitro binding-inhibition data failed to show any correlation between antibody titer and functional inhibition (P-value=0.12, 0.46, 0.91, 0.96 and 1.0 respectively for anti-Sal1, 7.18, P, DEKnull and the combination Sal1/7.18/P).

Example 14

Immunogenicity and Cross Reactivity (Group 1)

All PvDBP-RII immunogens produced high titers to homologous antigens; Single variant vaccines produced more strain-specific inhibitory responses; PvDBP-RII DEKnull elicited antibodies to shared neutralizing epitopes on PvDBP-R11; Mixed variant vaccine produced a higher inhibitory response than the single variant and DEKnull vaccines.

Three naturally occurring PvDBP-RII variants and one synthetic PvDBP-RII variant were chosen for immunization. The naturally-occurring PvDBP-RII variants were tested individually as well as in combination. PvMSP1-19 was chosen as a negative control antigen. Table 1 indicates the antigen administration plan for assessment of immunogenicity and cross reactivity. Each antigen or combination of antigens was administered to 4-6 week old female BALB/c mice in two doses (Day 0 and Day 21). Fifty μl of sterile antigen formulation (25 μg antigen in 25 μl aqueous solution emulsified 1:1 with 25 μL TITERMAX GOLD® commercial adjuvant) was injected subcutaneously into each mouse at the base of the tail. Survival serum samples (50 μuL) for ELISA were collected on days 0 and 35. Animals were euthanized and exsanguinated on day 42, and serum was stored for later testing.

TABLE 1

PvDBP-RII antigen administration strategy for immunogenicity and cross reactivity (Group I)

| Day 0 | Day 0 Primary immunization | Day 21 First Boost | Day 35 Test Bleed | Day 42 Final Bleed Euthanasia |
|---|---|---|---|---|
| Pre-immune bleed | PvDBP-RII-Sal 1 | PvDBP-RII-Sal 1 | Test Bleed | Final Bleed |
| Pre-immune bleed | PvDBP-RII-7.18 | PvDBP-RII-7.18 | Test Bleed | Final Bleed |
| Pre-immune bleed | PvDBP-RII-P | PvDBP-RII-P | Test Bleed | Final Bleed |
| Pre-immune bleed | PvDBP-RII-Sal1/7.18/P | PvDBP-RII-Sal1/7.18/P | Test Bleed | Final Bleed |
| Pre-immune bleed | PvDBP-RII-DEKnull | PvDBP-RII-DEKnull | Test Bleed | Final Bleed |
| Pre-immune bleed | PvMSP1-19 | PvMSP1-19 | Test Bleed | Final Bleed |
| Pre-immune bleed | Adjuvant only | Adjuvant only | Test Bleed | Final Bleed |

Example 15

Anamnestic Boost (Group 2)

All PvDBP-RII DEKnull anamnestic responses were higher than Sal 1 prime/Sal 1 boost (Sal $1^{sal\ 1}$) immunization; All PvDBP-RII cohorts produced a strong memory response to anamnestic boost; Antibodies within each PvDBP-RII cohort had similar heterologous PvDBP-RII reactivity but differences were observed in antibody responses between cohorts.

Table 2 indicates the antigen administration strategy for determining if antibodies against synthetic PvDBP-RII variant DEKnull were capable of being recalled after boosting with naturally occurring antigens. These mice received a two-injection primary course (Day 0 and Day 21) with synthetic PvDBP-RII variant DEKnull followed by injection with a native variant (Day 224). An initial test bleed on Day 42 was used to determine peak IgG levels. Small volume (50 μl) test bleeds were then carried out on a subset of the mice in each cohort on a monthly basis (beginning on Day 70) to determine when IgG levels had dropped sufficiently below their peak levels. When IgG levels had dropped by approximately 50% from their peak (Day 217) mice received an anamnestic boost injection (Day 224) with either PvDBP-RII-DEKnull, PvDBP-RII-Sal 1, PvDBP-RII-7.18, PvDBP-RII-P, or the negative control antigen (PvMSP1-19). A PvDBP-RII-Sal 1-primed cohort of mice was also homologously boosted with PvDBP-RII-Sal 1 as a positive control. Mice were euthanized and exsanguinated three weeks following anamnestic boost (Day 245) and serum was collected for later testing.

TABLE 2

PvDBP-RII antigen administration strategy for anamnestic boost

| Reference Name | Day 0 Primary immunization[a] | Day 21 First Boost | Day 42 Initial Test Bleed | Day 70-217 Monthly Test Bleeds | Day 224 Anamnestic Boost | Day 245 Final Bleed/ Euthanasia |
|---|---|---|---|---|---|---|
| DEKnull[DEKnull] | PvDBP-RII-DEKnull | PvDBP-RII-DEKnull | Test Bleed | Test Bleed | PvDBP-RII-DEKnull | Final Bleed |
| DEKnull[Sal 1] | PvDBP-RII-DEKnull | PvDBP-RII-DEKnull | Test Bleed | Test Bleed | PvDBP-RII-Sal 1 | Final Bleed |
| DEKnull[7.18] | PvDBP-RII-DEKnull | PvDBP-RII-DEKnull | Test Bleed | Test Bleed | PvDBP-RII-7.18 | Final Bleed |
| DEKnull[P] | PvDBP-RII-DEKnull | PvDBP-RII-DEKnull | Test Bleed | Test Bleed | PvDBP-RII-P | Final Bleed |
| DEKnull[MSP1-19] | PvDBP-RII-DEKnull | PvDBP-RII-DEKnull | Test Bleed | Test Bleed | PvMSP1-19 | Final Bleed |
| Sal 1[Sal 1] | PvDBP-RII-Sal 1 | PvDBP-RII-Sal 1 | Test Bleed | Test Bleed | PvDBP-RII-Sal 1 | Final Bleed |
| Adjuvant | Adjuvant only | Adjuvant only | Test Bleed | Test Bleed | Adjuvant only | Final Bleed |

[a]Day 0; Pre-immune bleed followed by primary immunization

Example 16

Assessment of Immunogenicity and Cross-Reactivity

Figure 12:
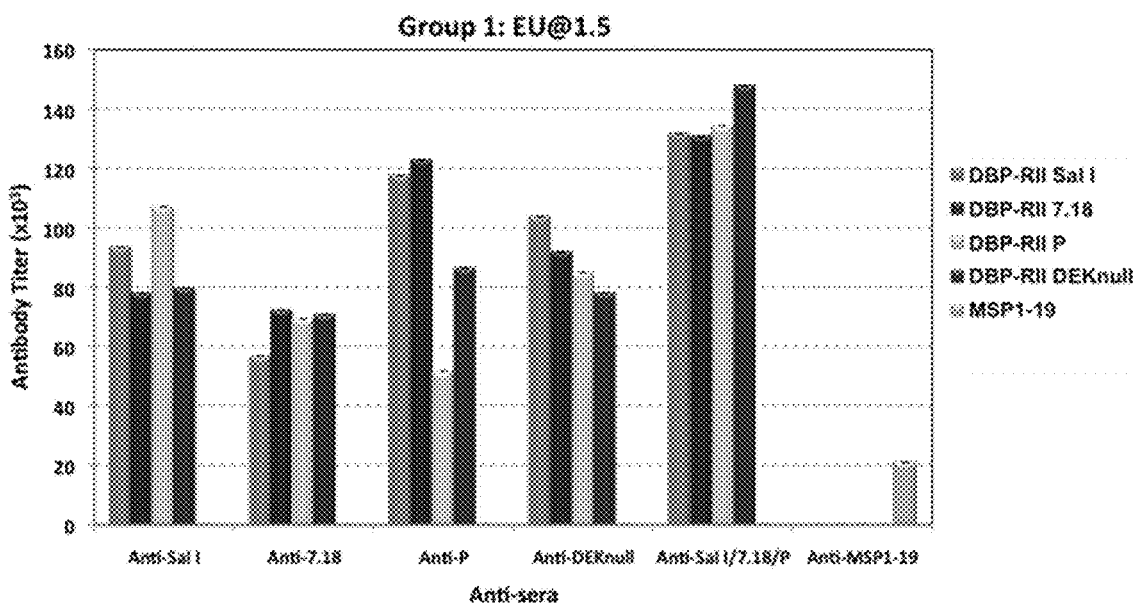
FIG. 12 is a bar graph summarizing the reactivity of all Group 1 anti-sera at 1.5 EU against PvDBP-RII antigens. Statistical analysis was performed comparing a single point (EU=1.5) on the log phase of each curve. Analysis indicates that all anti-sera reacted equally well to all of the PvDBP-RII variants and did not react to PvMSP1-19. The anti-PvDBP-RII Sal 1/7.18/P serum was more reactive overall than the anti-PvDBP-RII Sal 1, anti-PvDBP-RII 7.18 or anti-PvIDBP-RII DEKnull sera.

Serum samples from individual mice were initially tested by ELISA at seven dilutions for reactivity to the homologous antigen (i.e., the immunization antigen). A 4-parameter logistic regression curve was then plotted showing the reactivity of each cohort against its homologous antigen (shown in FIGS. 19A-23F). Each serum sample was then tested for reactivity to the heterologous PvDBP-RII antigens and the PvMSP1-19 negative control antigen. Logistic regression curves showing reactivity to the homologous and heterologous antigens for animals in each cohort were plotted (FIGS. 7-11). Statistical analysis was performed comparing a single point (EU=1.5) on the log phase of the curve (FIG. 12).

Figure 24:
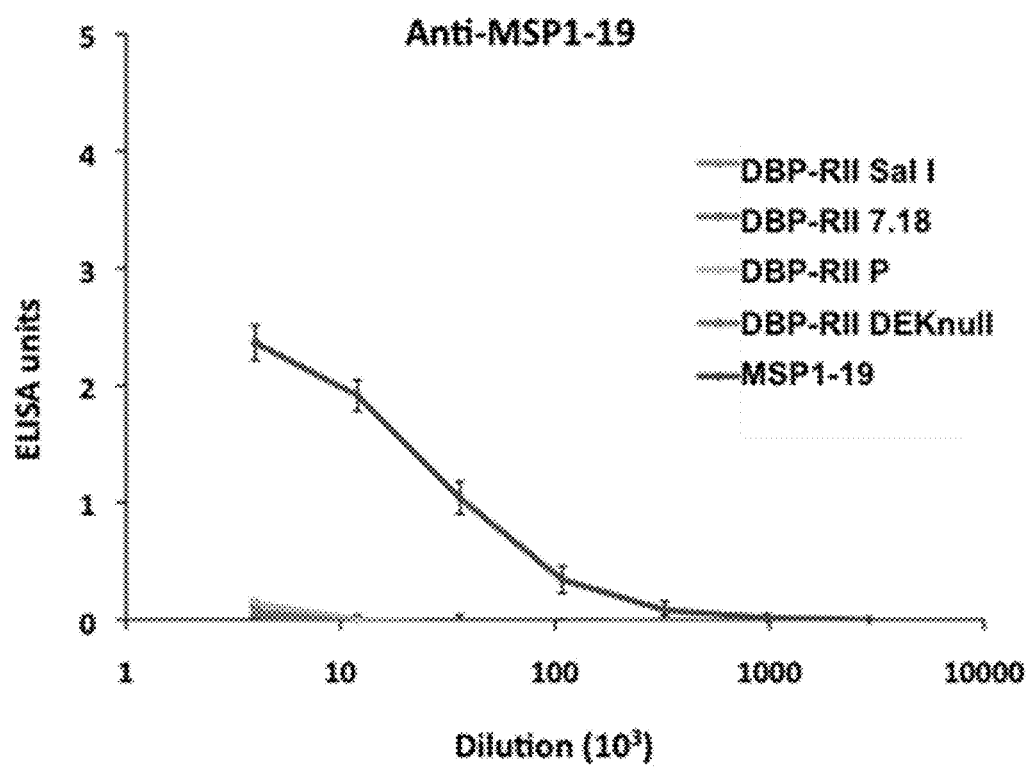
FIG. 24 is a graph illustrating the assessment of cross-reactivity of anti-MSP1-19 negative control sera against heterologous antigens.
Figure 25A:
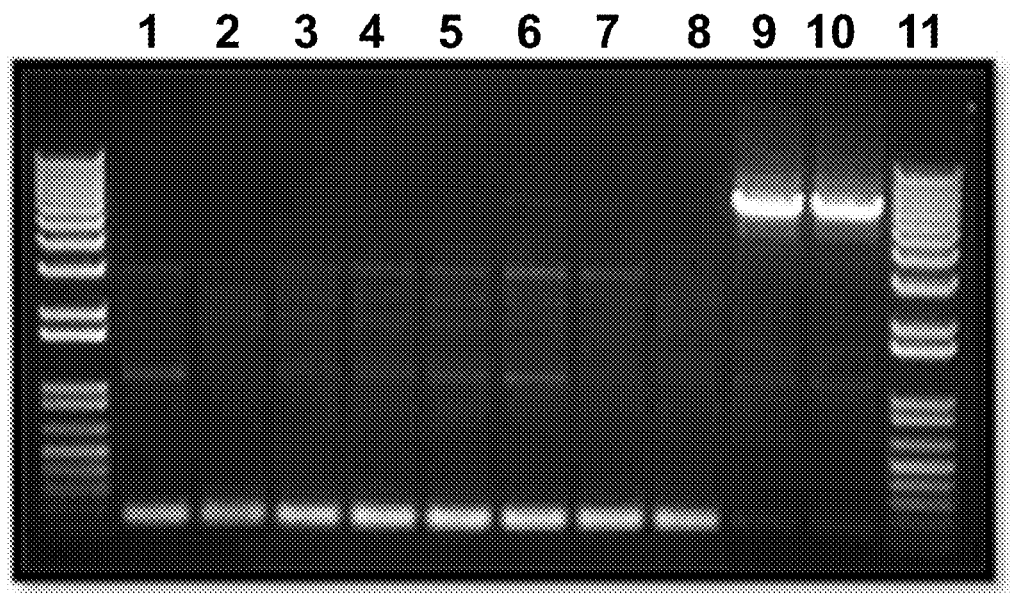
FIGS. 25A-25E are a series of digital images illustrating the cloning and validation of constructs used in the COS7 erythrocyte binding inhibition assay.
Figure 25B:
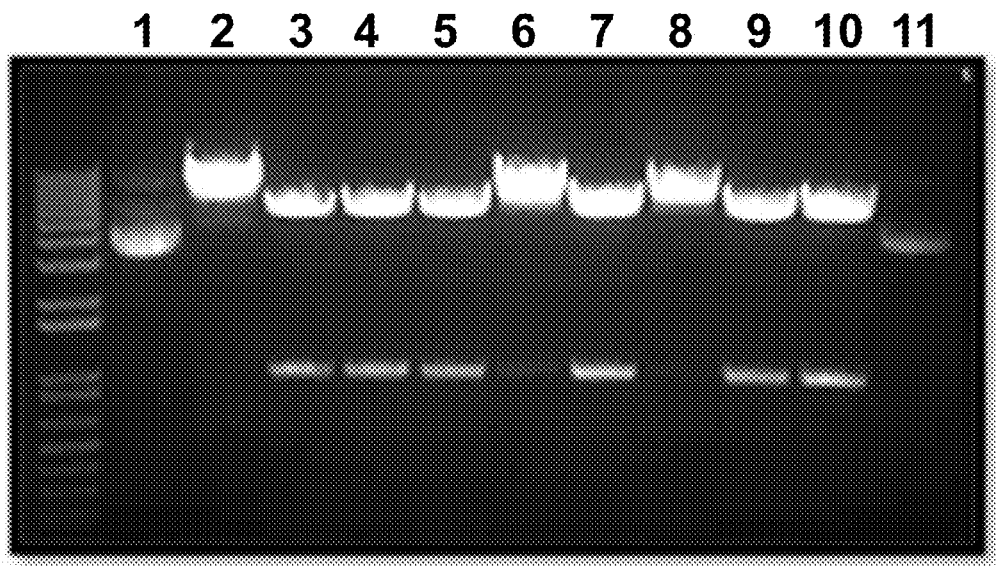
Figure 25C:
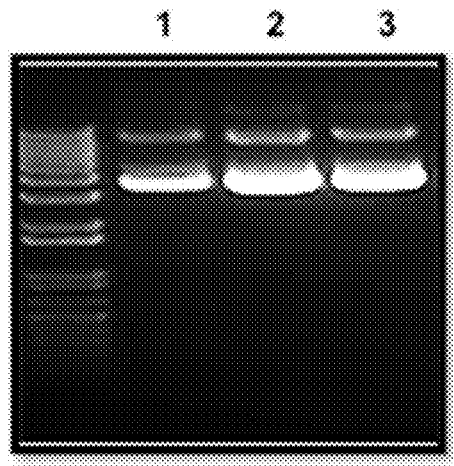
Figure 25D:
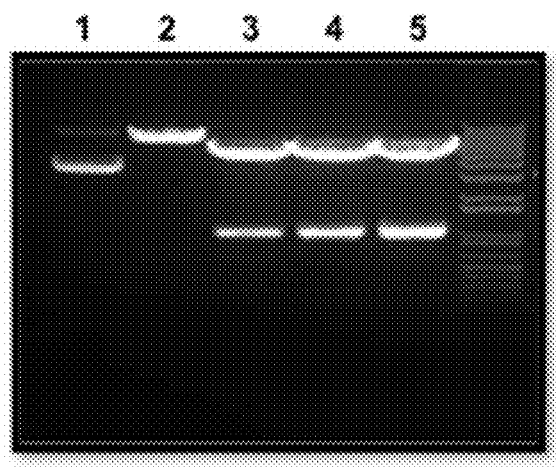
Figure 25E:
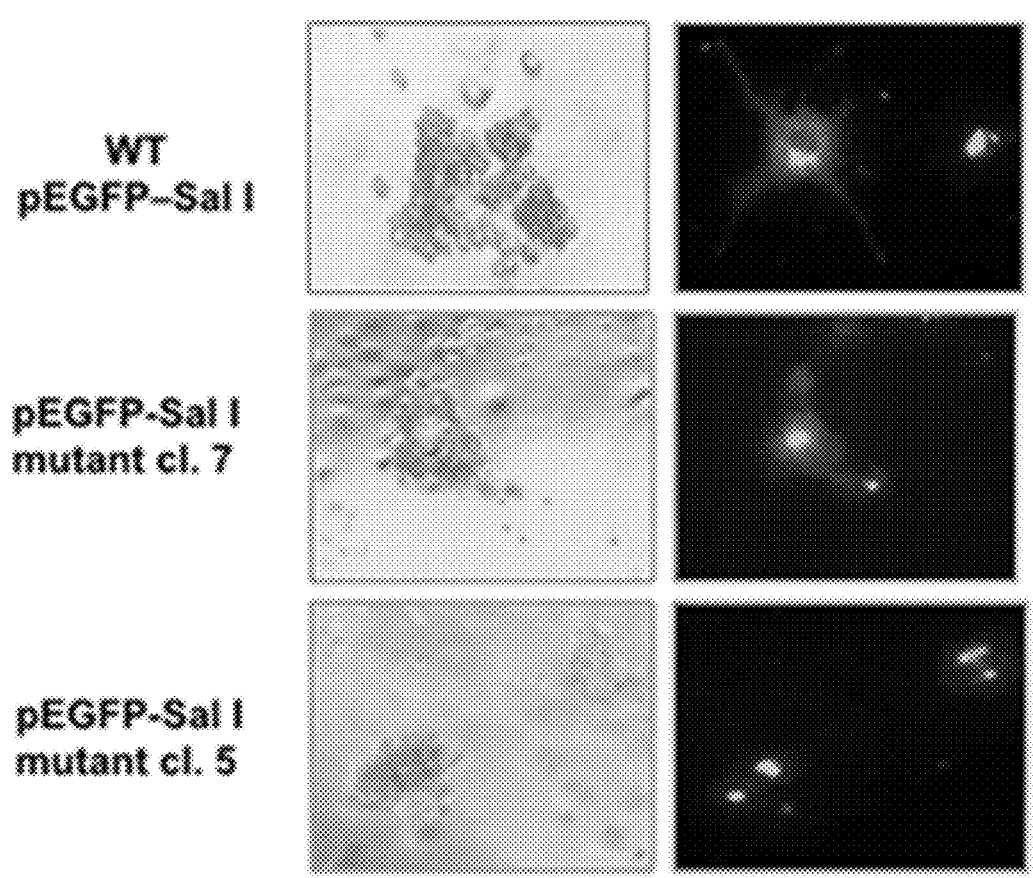
Figure 27A:
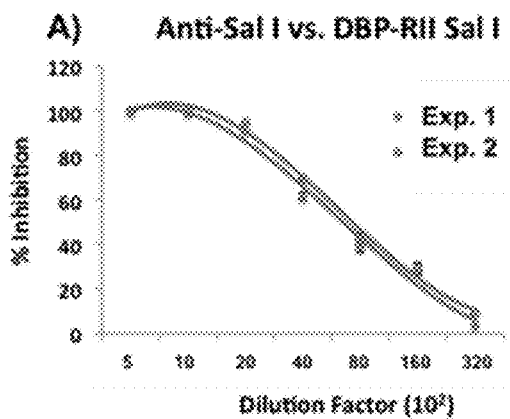
FIGS. 27A-27E are a series of graphs illustrating the inhibition of Duffy positive human erythrocyte binding to COS7-expressed PvDBP-RII variant Sal 1.
Figure 27B:
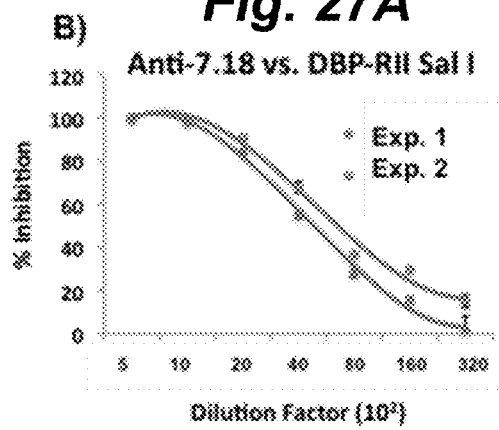
Figure 27C:
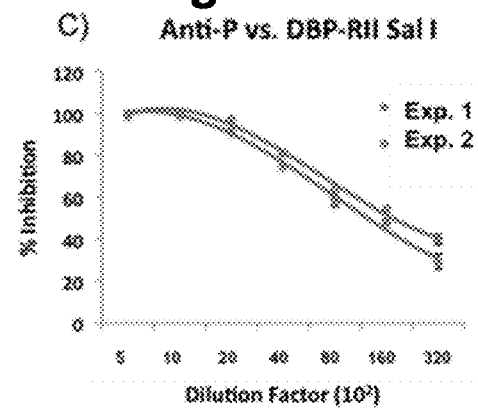
Figure 27D:
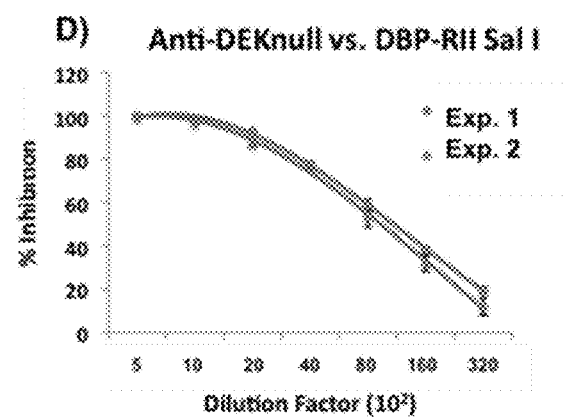
Figure 27E:
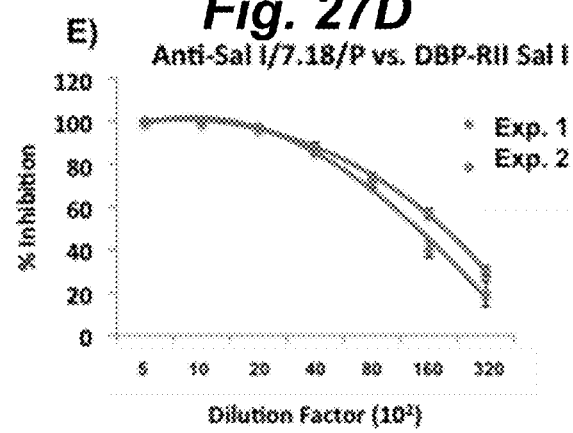
Figure 28:
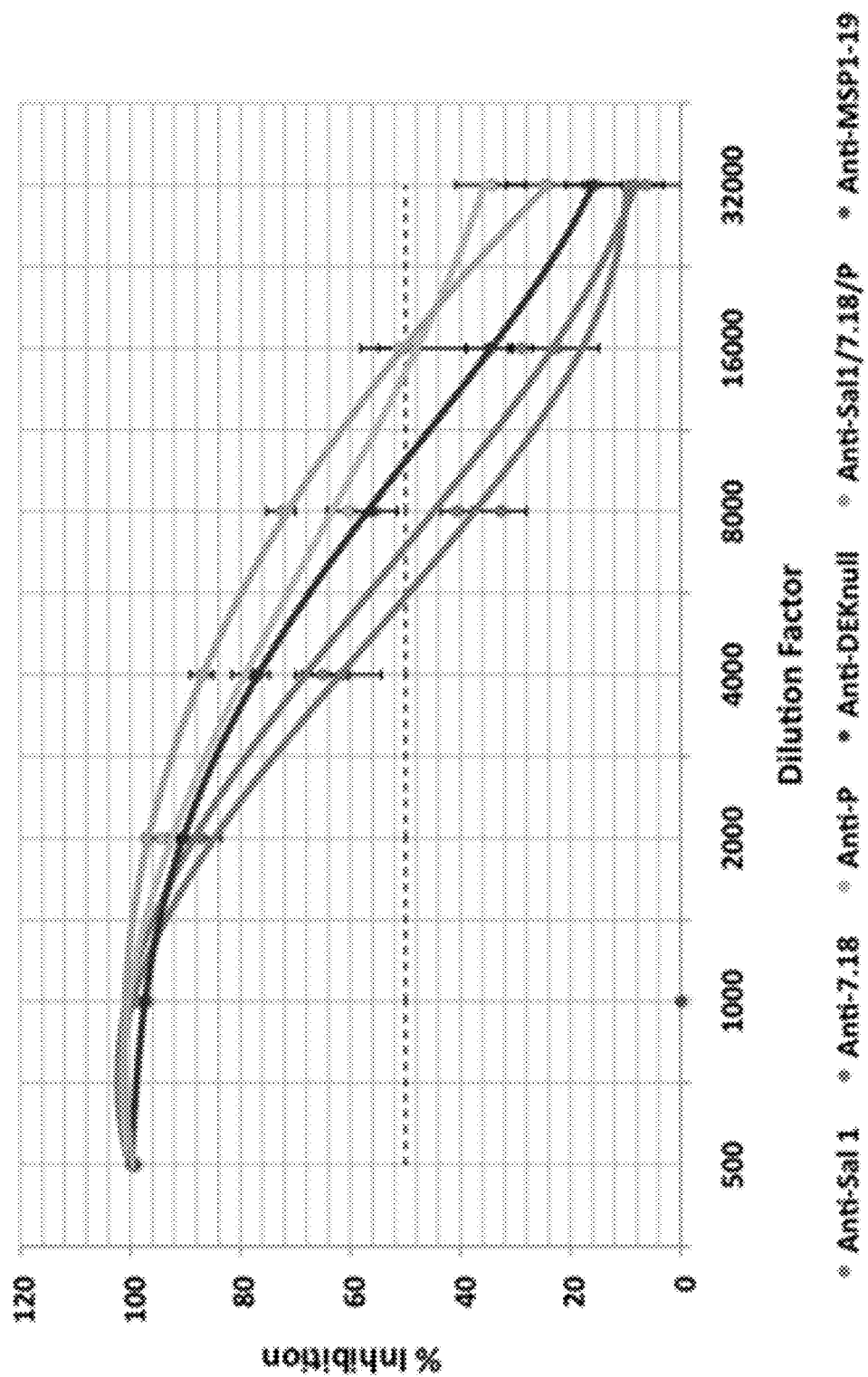
FIG. 28 is a graph illustrating the inhibition of Duffy positive erythrocyte binding to COS7-expressed PvDBP-RII Sal 1 variant.
Figures 29A, 29B, 29C, 29D, 29E:
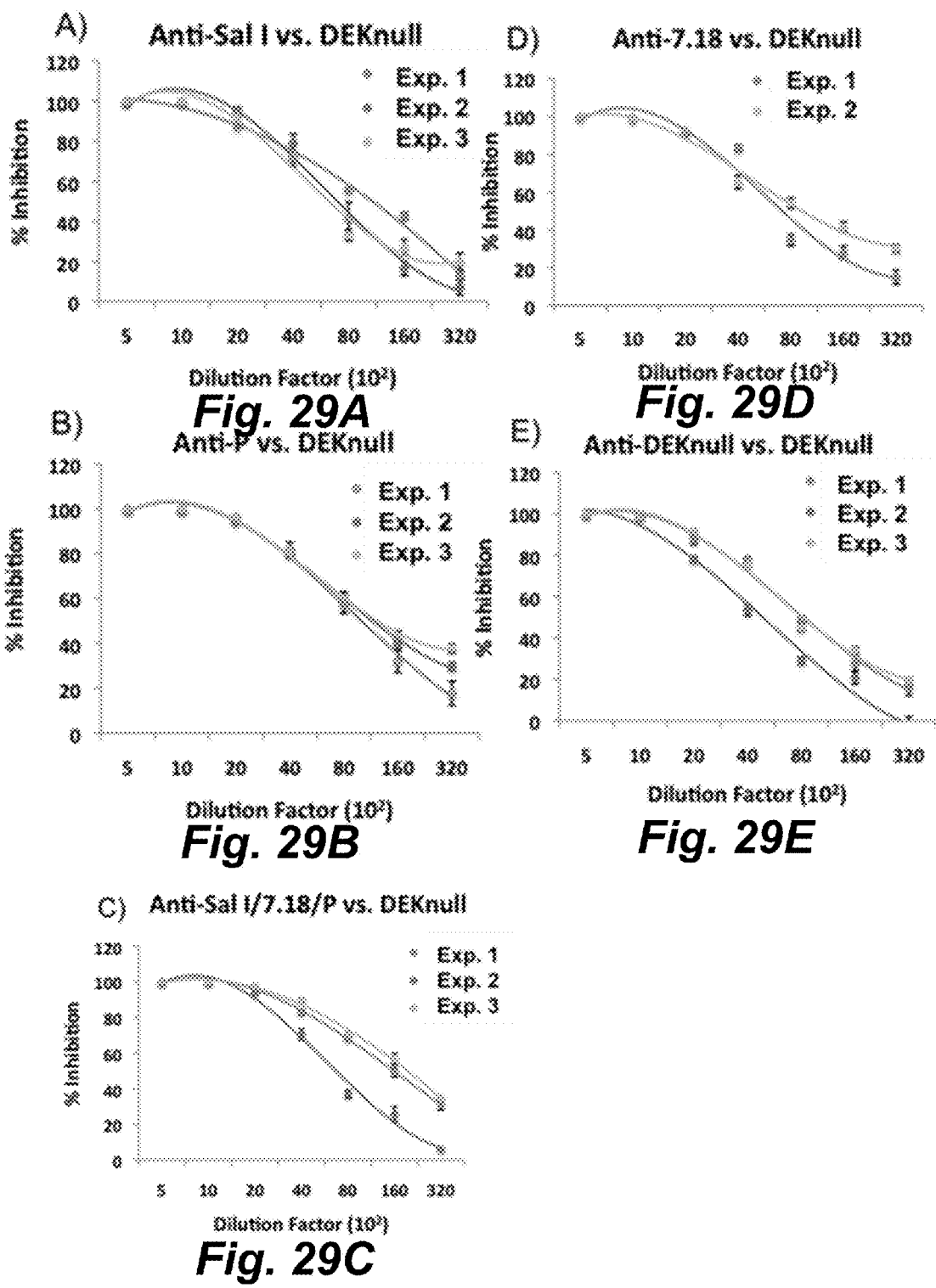
FIGS. 29A-29E are a series of graphs illustrating the inhibition of Duffy positive human erythrocyte binding to COS7-expressed PvDBP-RII variant DEKnull.
Figure 30:
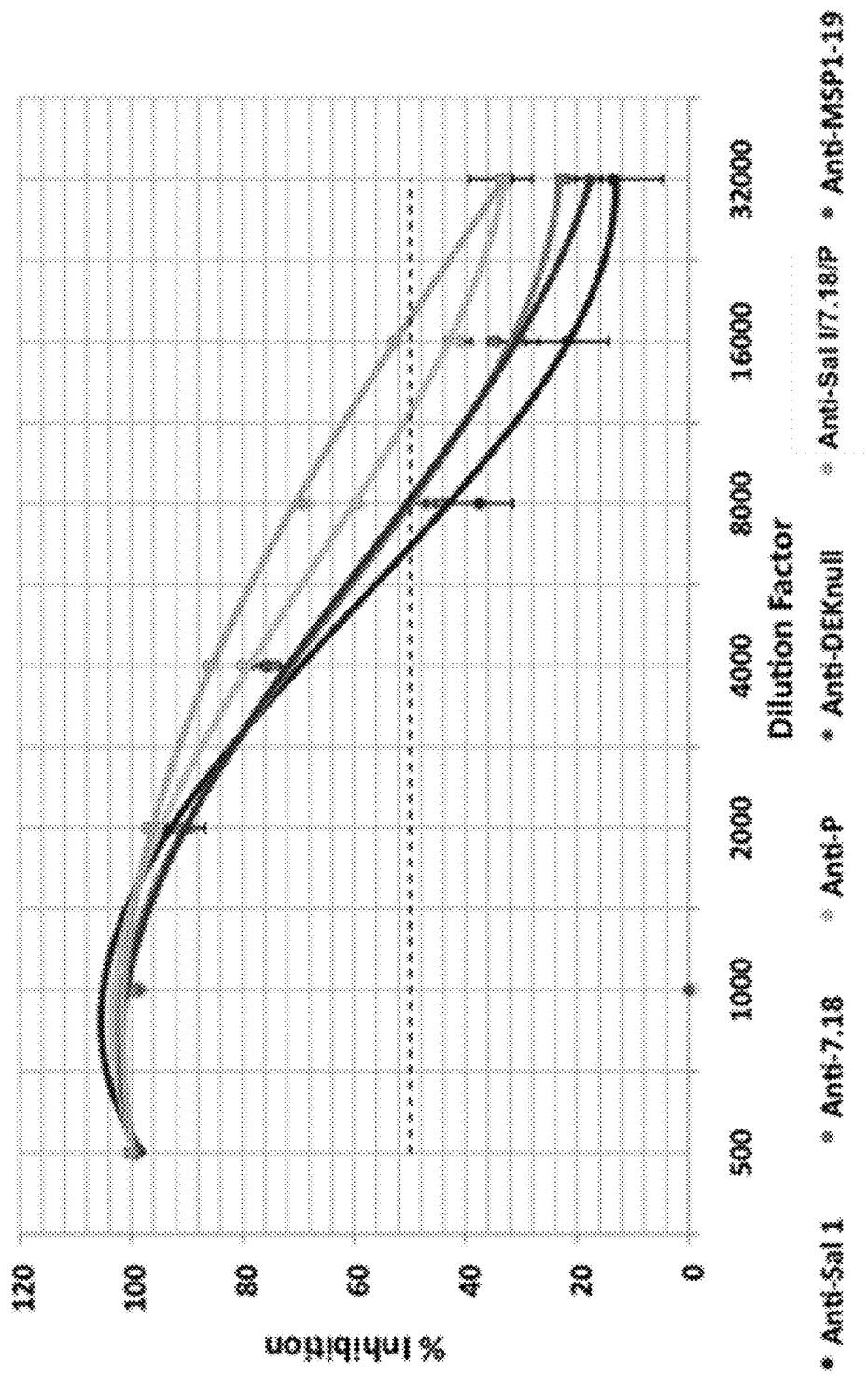
FIG. 30 is a graph illustrating the inhibition of Duffy positive erythrocyte binding to COS7-expressed synthetic PvDBP-RII variant DEKnull.
Figure 32:
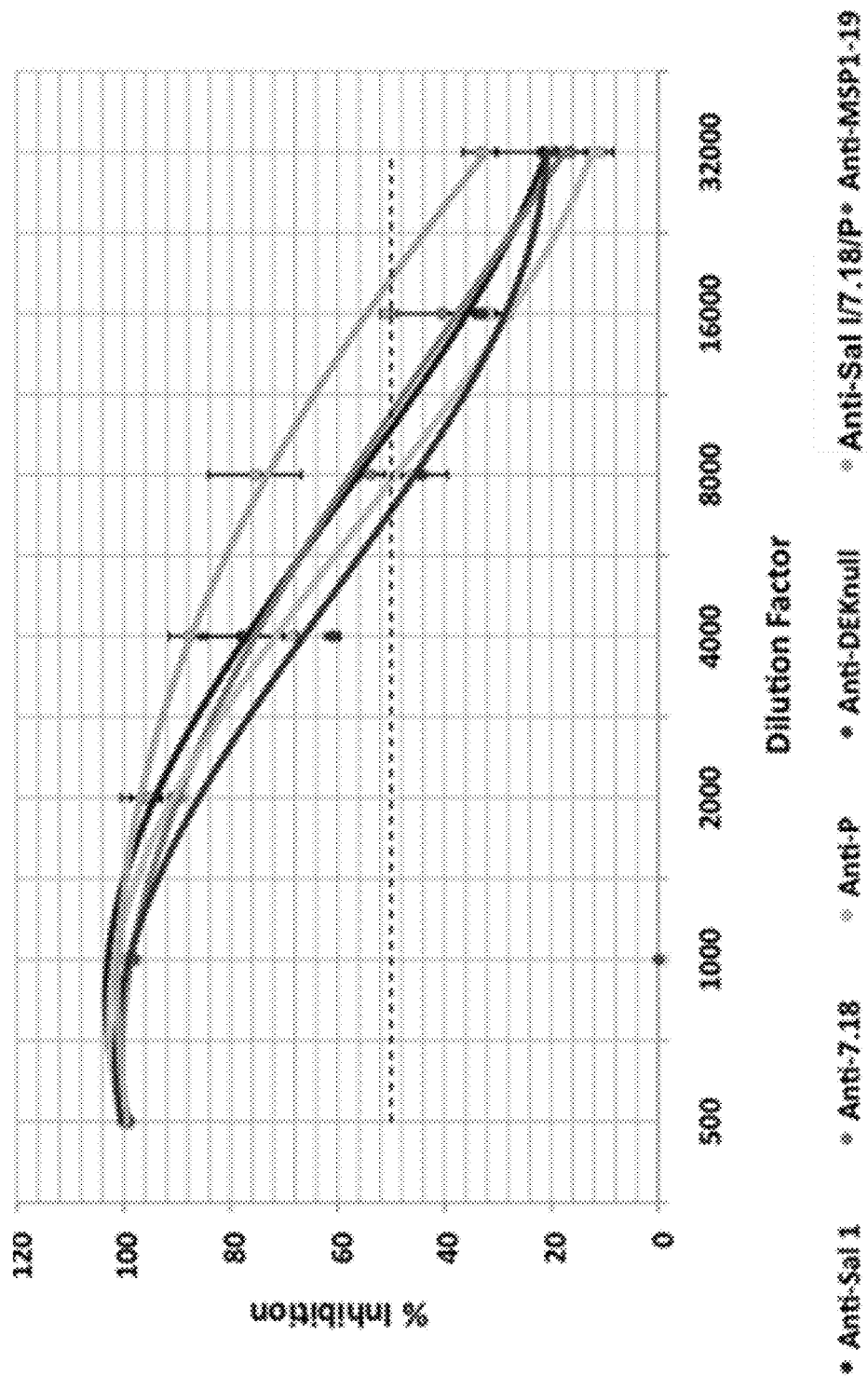
FIG. 32 is a graph illustrating the inhibition of Duffy positive erythrocyte binding to COS7-expressed PvDBP-RII 27.16 variant.
Figure 33A:
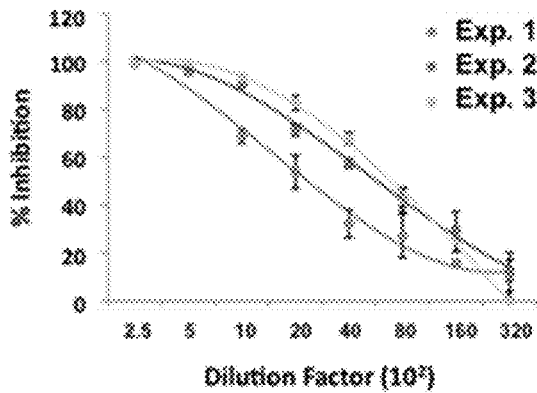
FIGS. 33A-33E are a series of graphs illustrating the inhibition of Duffy positive human erythrocyte binding to COS7-expressed PvDBP-RII variant 7.18.
Figure 33D:
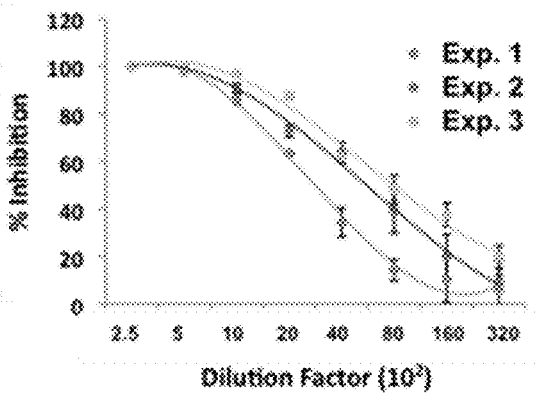
Figure 33B:
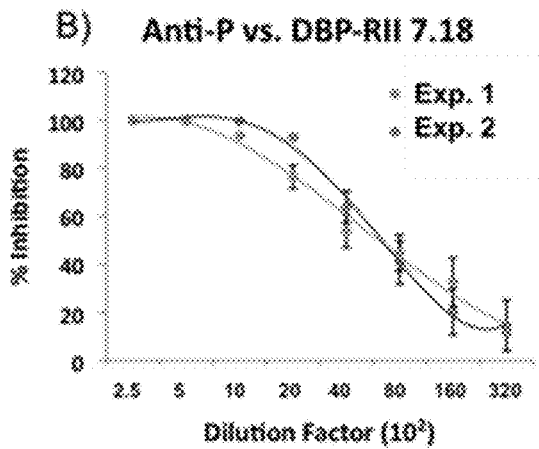
Figure 33E:
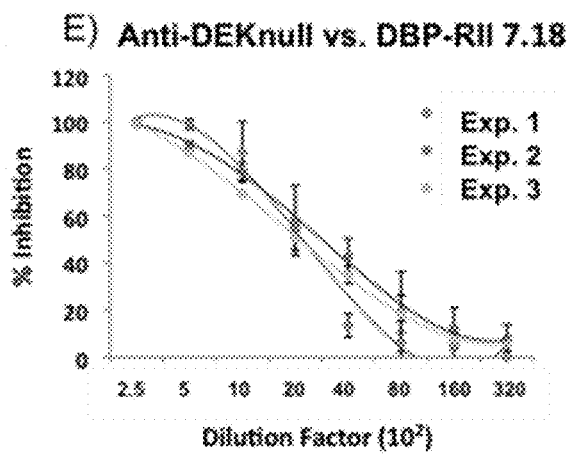
Figure 33C:
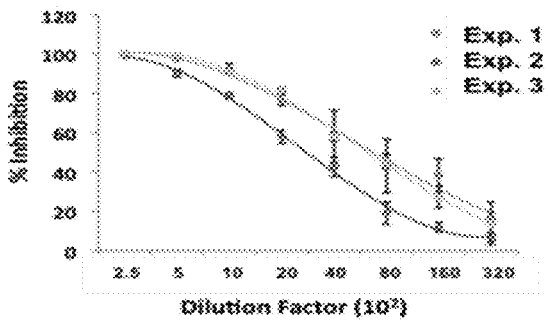
Figure 34:
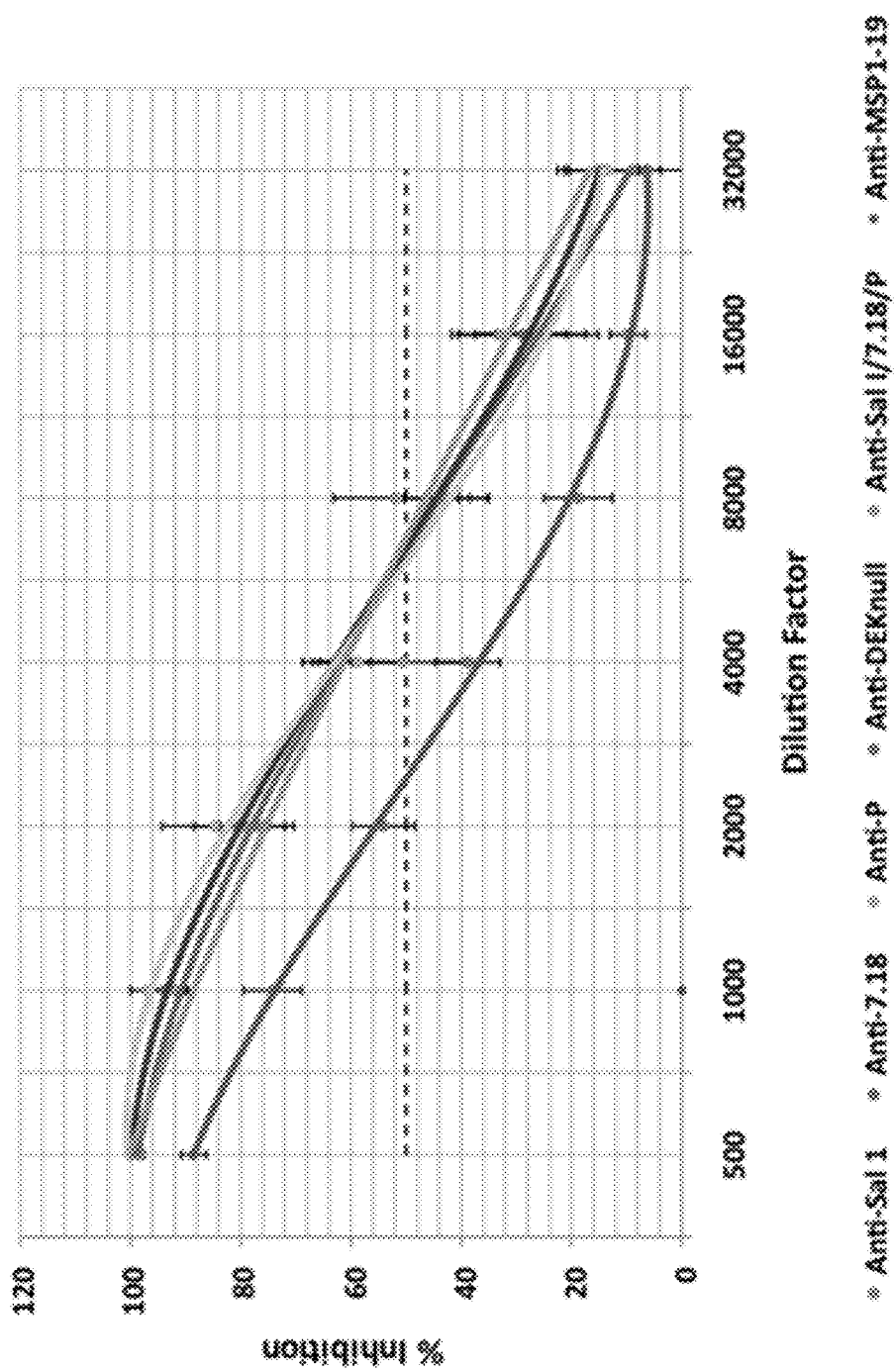
FIG. 34 is a graph illustrating the inhibition of Duffy positive erythrocyte binding to COS7-expressed PvDBP-RII 7.18 variant.
Figure 35:
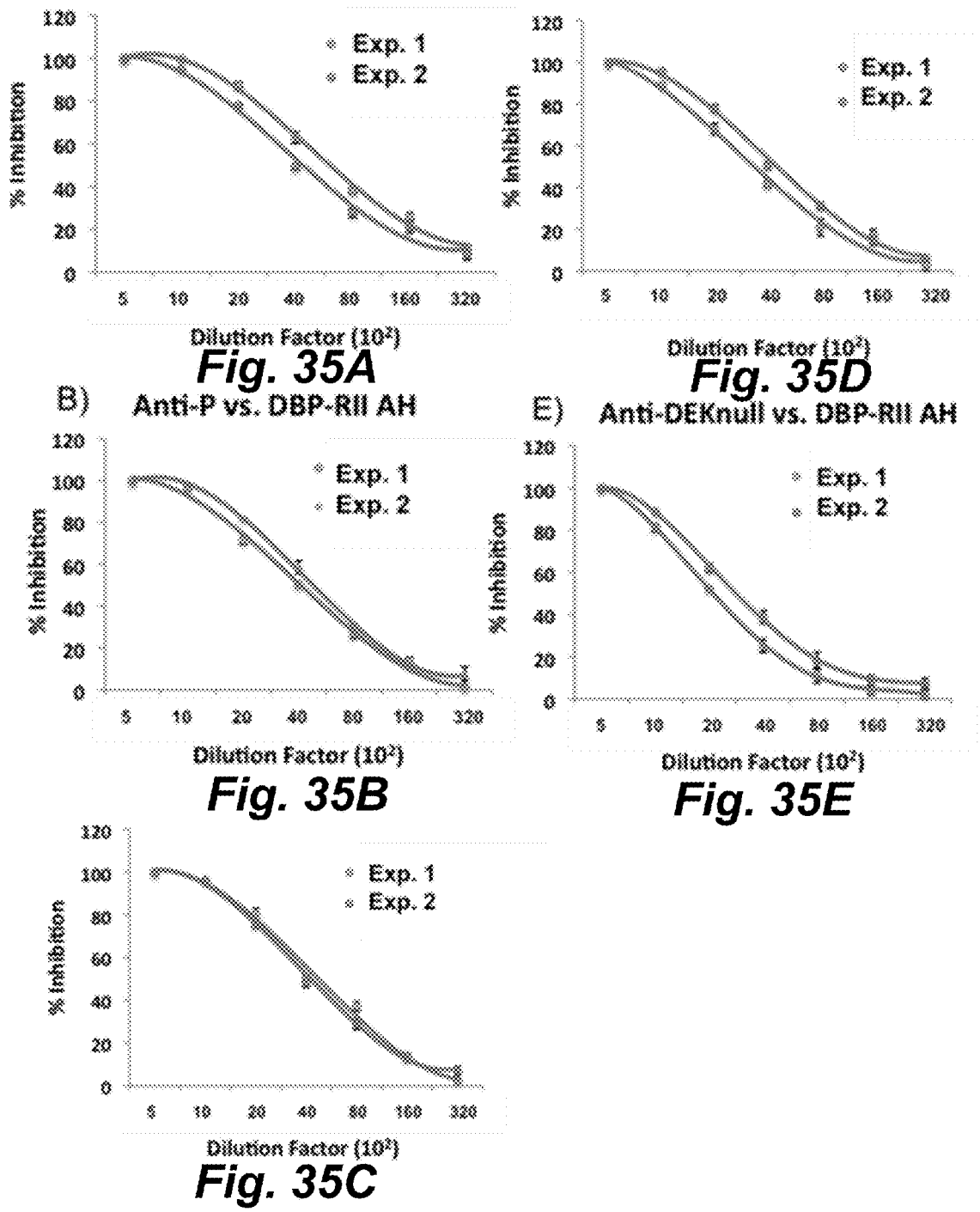
FIGS. 35A-35E are a series of graphs illustrating the Inhibition of Duffy positive human erythrocyte binding to COS7-expressed PvDBP-RII variant AH.
Figure 36:
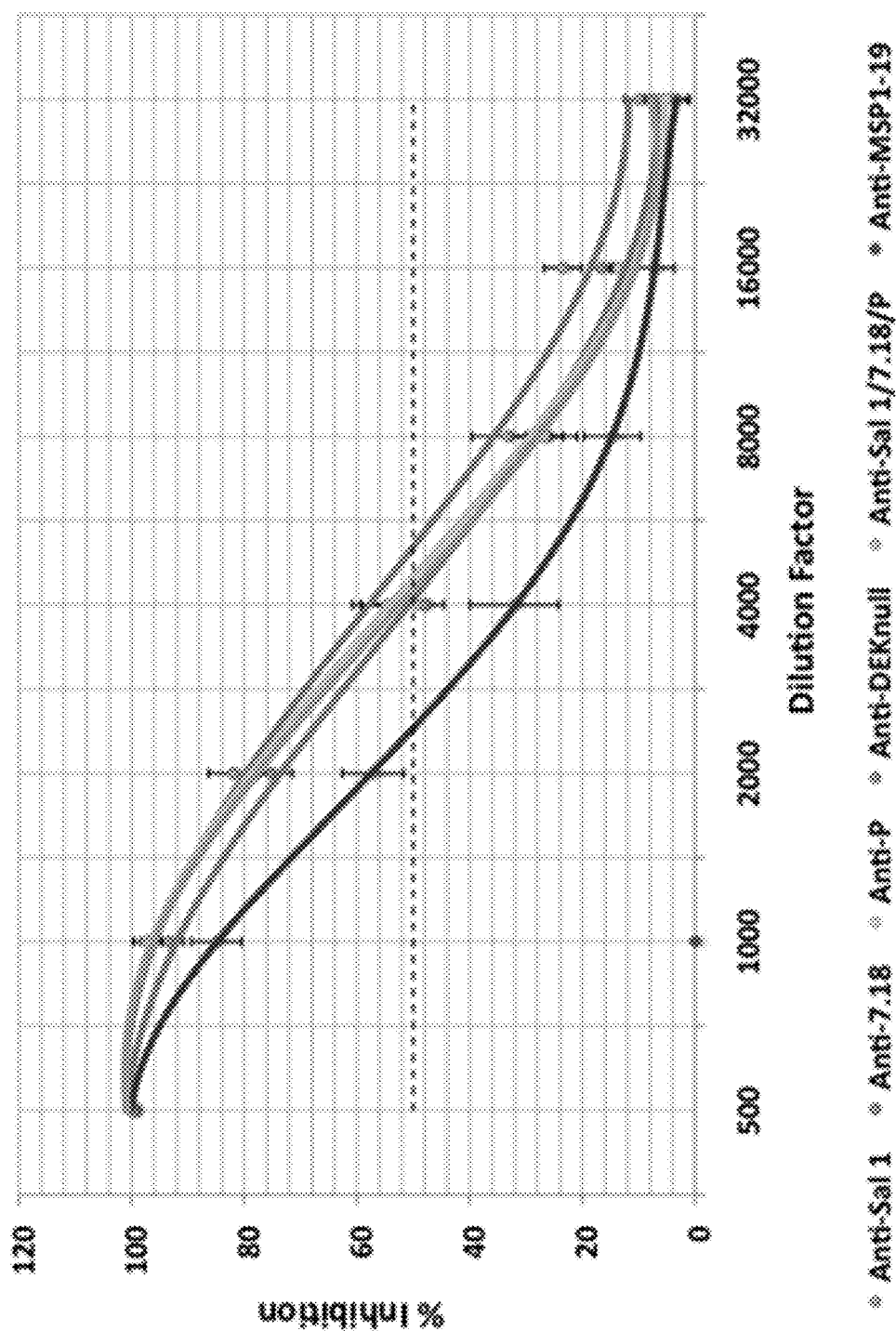
FIG. 36 is a graph illustrating the inhibition of Duffy positive erythrocyte binding to COS7-expressed PvDBP-RII AH variant.
Figure 37A:
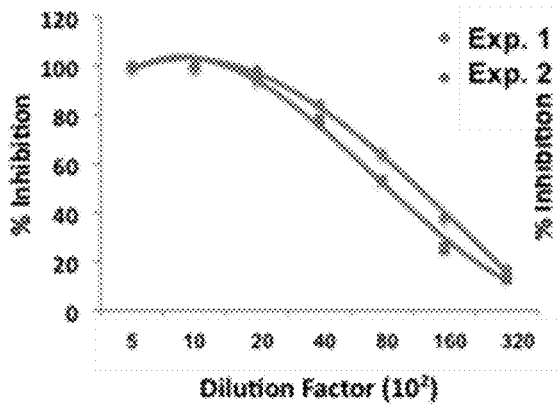
FIGS. 37A-37E are a series of graphs illustrating the inhibition of Duffy positive human erythrocyte binding to COS7-expressed PvDBP-RII variant P.
Figure 37D:
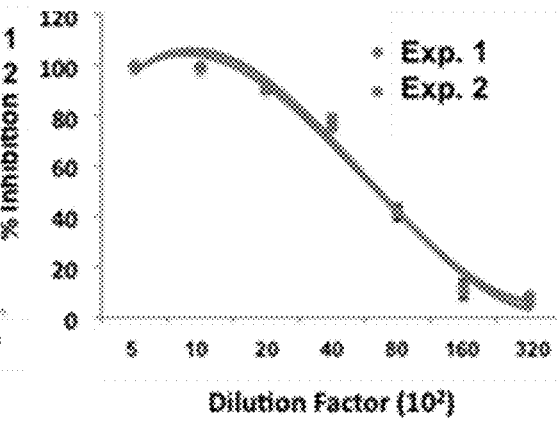
Figure 37B:
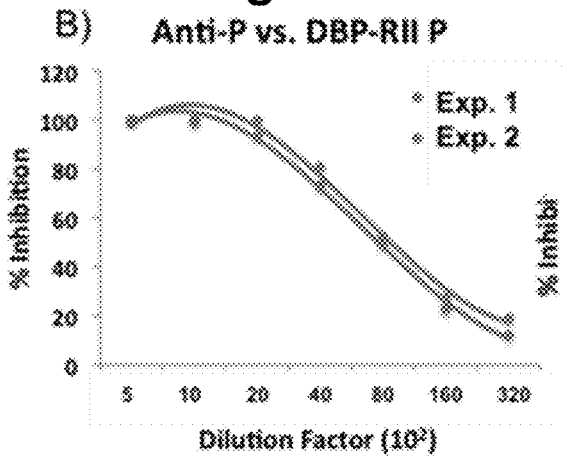
Figure 37E:
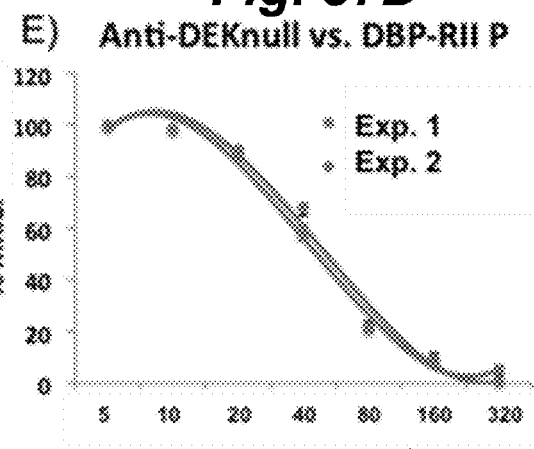
Figure 37C:
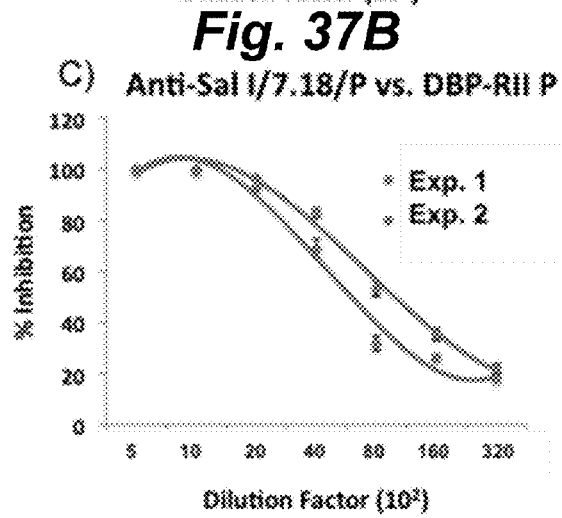
Figure 38:
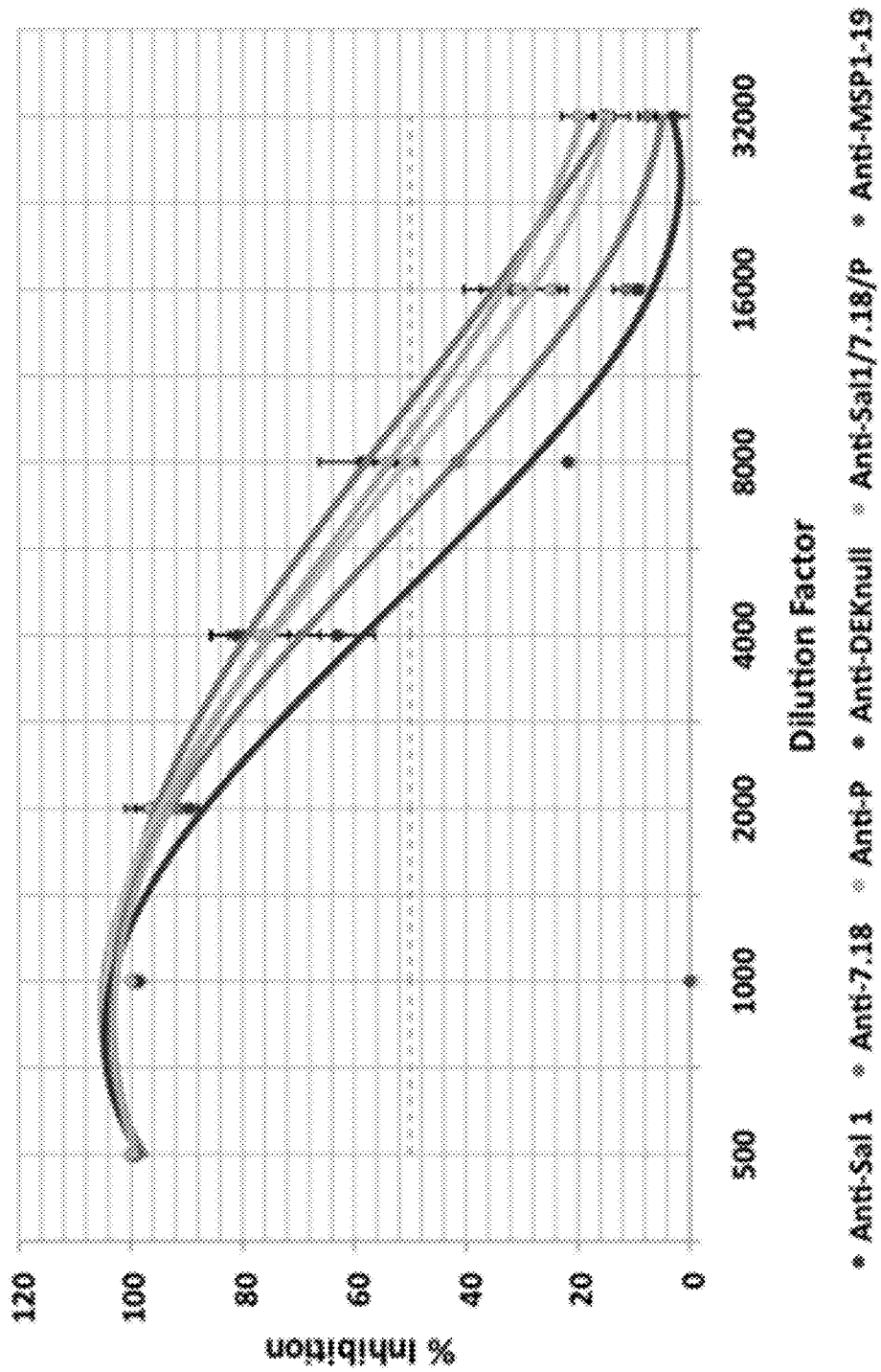
FIG. 38 is a graph illustrating the inhibition of Duffy positive erythrocyte binding to COS7-expressed PvDBP-RII P variant.

This analysis indicates that each of the anti-PvDBP-RII sera reacted equally well to each of the PvDBP-RII variants and did not react to PvMSP1-19. The anti-PvMSP1-19 sera reacted only with the PvMSP1-19 antigen and not with any of the PvDBP-RII variants (FIG. 24). Anti-PvDBP-RII DEKnull sera is equally immunogenic to the single variant vaccinations. The anti-PvDBP-RII Sal 1/7.18/P sera was more reactive in the ELISA assays overall than the anti-PvDBP-RII Sal 1, anti-PvDBP-RII 7.18 or anti-PvDBP-RII DEKnull sera, although all PvDBP-RII immunogens produced high titers to homologous antigens.

Antigen preparations were adsorbed onto microtiter plates at a concentration of 200 ng/well. Anti-serum from each mouse was titered by end-point dilution against each antigen on the plate (starting at 1:4000 dilution). All OD values were normalized against a standard anti-PvDBP-RII monoclonal antibody, which was run on each plate. Outliers were excluded from the logistic regression based on the following criteria. An ANOVA was performed for each cohort against each antigen. If the p-value was greater than 0.05, there was no significant difference between the samples in the cohort and all were included in further analysis. If the p-value was less than 0.05, a Bonferroni multiple comparisons test was performed to determine where the difference lay and samples that were shown to vary significantly were removed from further analysis. Using this criteria, five sera were excluded from further analysis: Serum AS from the anti-PvDBP-RII-Sal 1 cohort, serum B6 and serum B11 from the anti-PvDBP-RII 7.18 cohort, serum D5 from the anti-PvDBP-RII DEKnull cohort and serum E14 from the anti-PvDBP-RII Sal 1/7.18/P cohort. All were excluded because they reacted highly with the PvMSP1-19 negative control antigen.

Example 17

Assessment of Erythrocyte Binding Inhibition

Following analysis by ELISA, serum samples from each cohort of mice were pooled and tested for their ability to inhibit binding of Duffy positive human erythrocytes to PvDBP-RII variants expressed on COS7-cells. Variants were chosen for analysis in the erythrocyte binding inhibition assay based on their divergent polymorphism (particularly in the DEK region) to achieve a geographically and genetically diverse sample (Table 3).

TABLE 3

PvDBP-RII variants for analysis in the COS7 erythrocyte binding assay.

| DBP-RII Variant | Accession No. SEQ ID NO.: | |
|---|---|---|
| DBP-R11-Sal 1 | P22290.2 SEQ ID NO.: 1 | RRLYKNDEKAQQRRKQNLWSQKIV[a] |
| DEKnull | n/a | RRLYKNAATAATSRTSNLWSQKIV[a] |
| DBP-RII-27.16* | AAL79076 SEQ ID NO. 8 | SRLYKNGAKAQQHRKQNIWKQEIV[a] |
| DBP-RII-7.18 | AAL79051.1 SEQ ID NO.: 6 | SRLYKNGAQAQQRRKQKIRSQKKV[a] |
| DBP-RII-AH* | AAY34130.1 SEQ ID NO.: 9 | SRLYENGAQAQQRRKQKIRSQKKV[a] |
| DBP-P | AAL79073.1 SEQ ID NO.: 7 | RRFYKDGKNAQQHRKQKIWSQKKV[a] |

[a]residue positions: 308, 319, 333, 369, 371, 375, 384, 385, 386, 387, 388, 389, 390, 391, 392, 393, 417, 424, 437, 447, 454, 492, 503, and 505, respectively.
A dot (.) means a residue is the same as the residue in PvDBP-RII Sal 1.
*Variants used in the COS assay analysis only and not for recombinant antigen production.

Pooled antisera from mice in Group 1 (immunogenicity and cross reactivity) were tested at 6 dilutions to assess their ability to inhibit binding of Duffy positive human erythrocytes to PvDBP-RII variants expressed on the surface of COS7 cells (both homologous and heterologous antigens).

COS7 (green monkey kidney epithelial) cells were maintained in Dulbecco's modified Eagle's medium (DMEM, Sigma, St. Louis, Mo.) containing 10% fetal bovine sera (FBS). COS7 cells, between the passage numbers of 5 and 20, were plated in 24-well plates at a density of 35,000 cells per well and transiently transfected with endotoxin-free plasmid DNA using Lipofectamine 2000 (Invitrogen, Carlsbad, Calif.) according to the manufacturer's instructions. Forty-two hours post-transfection, COS7 cells were pre-incubated for 1 hour at 37° C. with antisera diluted in incomplete DMEM and then incubated with Duffy-positive human erythrocytes ($2.5 \times 10^7$ cells/well, previously washed three times with incomplete DMEM), for 2 hours at 37° C. Wells were washed three times with PBS to remove non-adherent erythrocytes and binding was scored by counting the number of rosettes (COS7 cells covered 50% or more by erythrocytes) per 30 fields of view at 200× magnification using inverted phase microscopy.

The pEGFP-Sal 1 (original) plasmid was altered to contain an EcoRI restriction site in the place of the original PvuII restriction site to allow synthetic variant PvDBP-RII variants to be cloned into the pEGFP-Sal 1 (mut) backbone (FIGS. 25A-26B). All constructs used in the COS7 erythrocyte binding inhibition assay were validated for binding to Duffy positive human erythrocytes as shown in FIG. 13

Each pool of antisera was tested at 7 different dilutions for inhibition of Duffy positive human erythrocyte binding to 5 divergent COS7-expressed PvDBP-RII variants: Sal 1, 27.16, 7.18, AH and P (as shown in FIGS. 27A-38).

Two COS7 experiments were run in triplicate for each combination of antisera and COS7-expressed variant. A rosette ratio was determined by dividing the average number of rosettes from the diluted pooled cohort sera for each experimental well and the average number of rosettes from the pooled pre-immune sera. The percent inhibition was calculated by subtracting the rosette ratio from one and multiplying that number by 100. There was no correlation between the reactivity of the anti-sera by ELISA titer and the functional inhibitory capacity of each anti-sera in the COS7 erythrocyte binding inhibition assay (anti-PvDBP-RII Sal 1 p=0.12, anti-PvDBP-RII 7.18 p=0.46, anti-PvDBP-RII P p=0.91, anti-PvDBP-RII DEKnull p=0.96, anti-PvDBP-RII Sal 1/7.18/P p=1.0).

Figure 39:
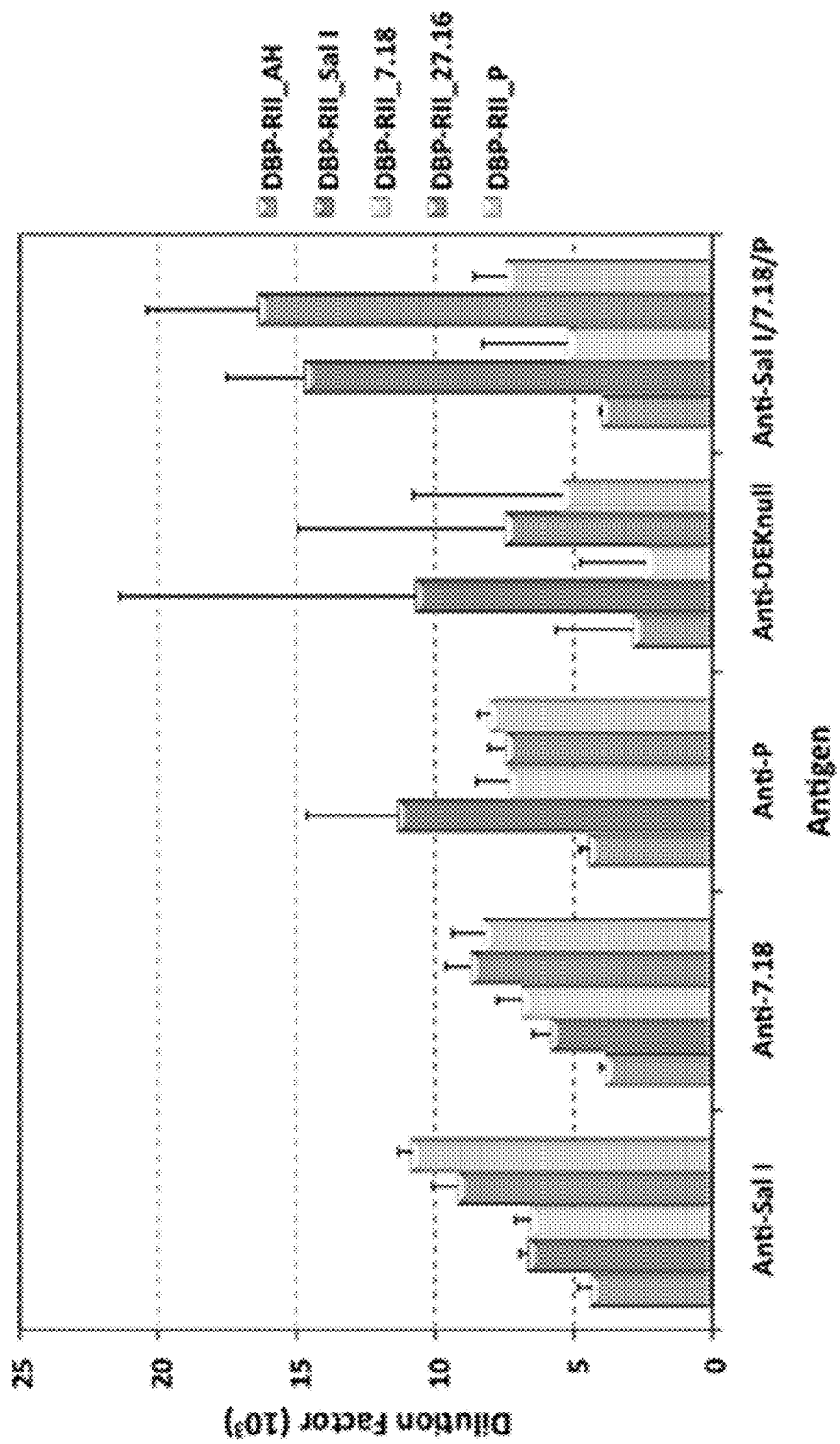
FIG. 39 is a graph illustrating the $IC_{50}$ of each PvDBP-RII antigen.
Figure 41A:
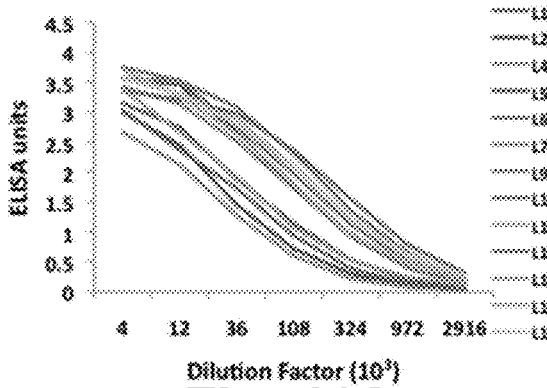
Figure 41B:
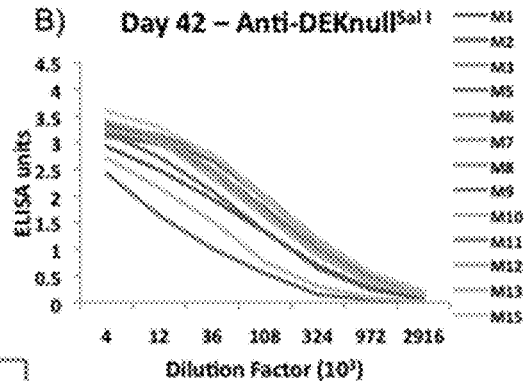
Figure 41C:
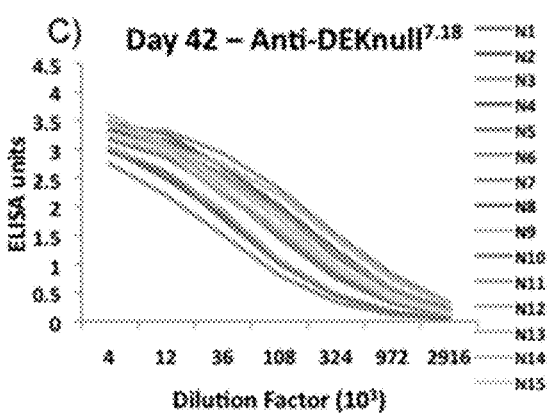
Figure 41D:
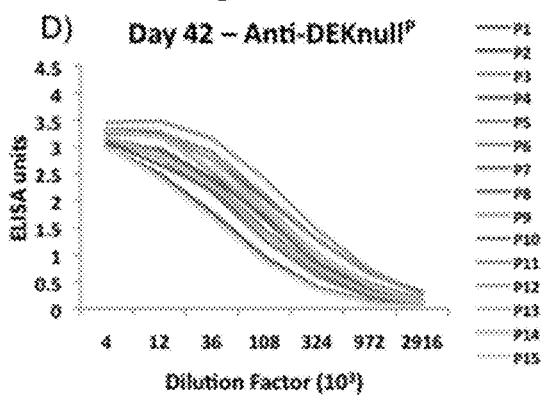
Figure 41E:
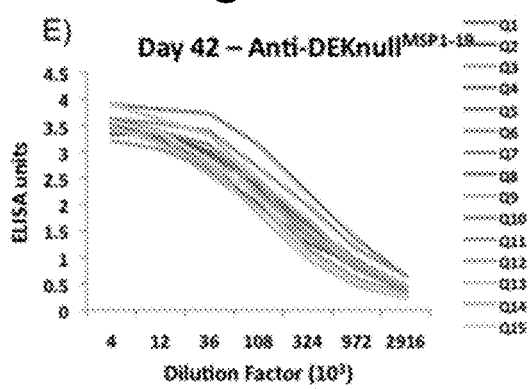
Figure 41F:
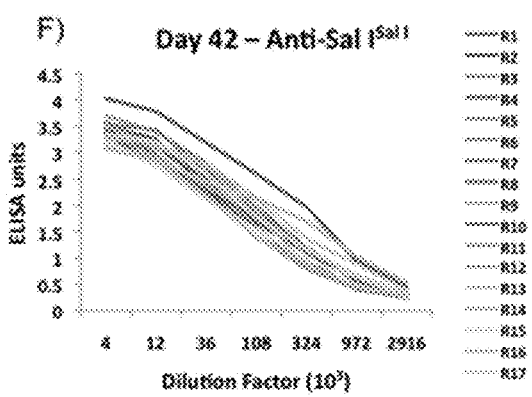
Figure 43A:
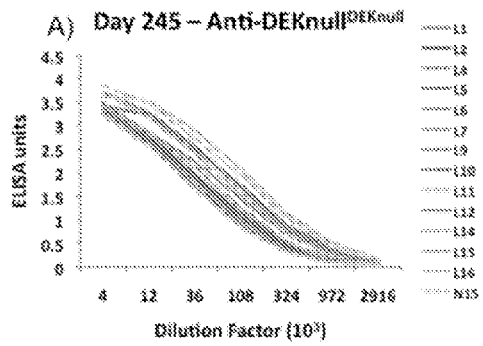
FIGS. 43A-43F are a series of graphs illustrating the day 245 final titers of anamenestic boost anti-sera to the anamenestic boost antigen.
Figure 43B:
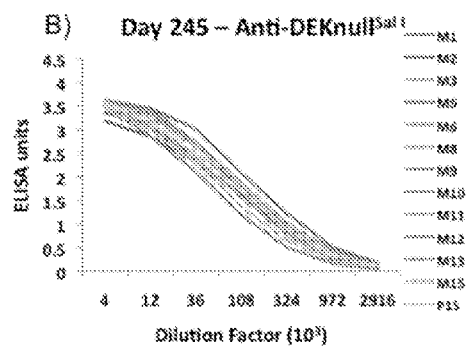
Figure 43C:
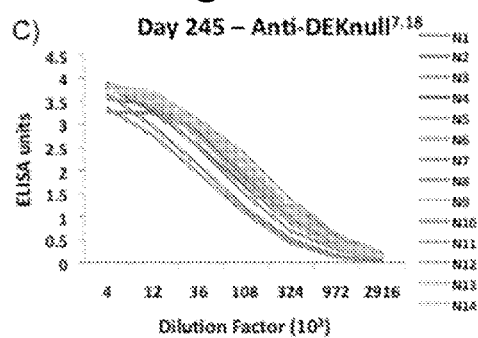
Figure 43D:
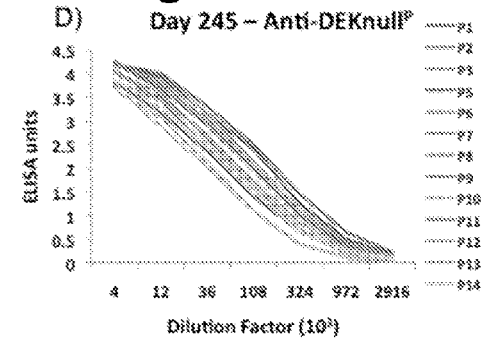
Figure 43E:
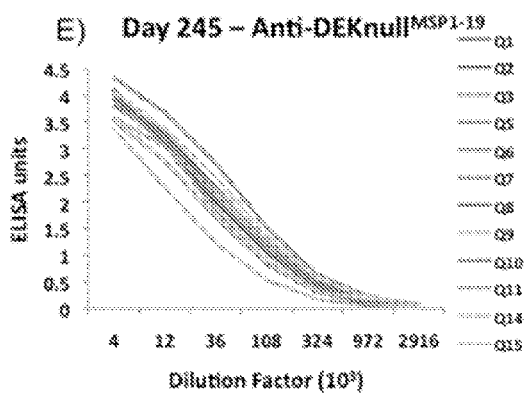
Figure 43F:
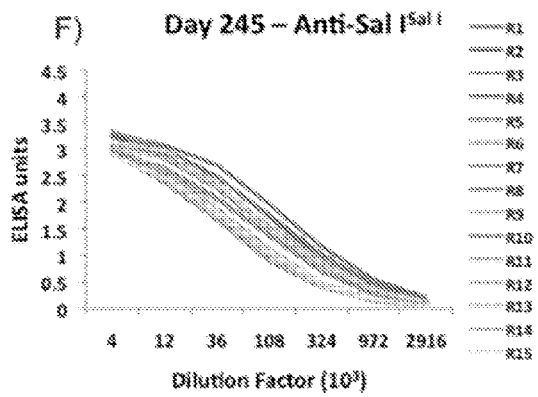

The minimum dilution of anti-PvDBP-RII sera to inhibit 50% of binding of human erythrocytes was determined for each COS7-expressed PvDBP-RII variant (FIGS. 14A-14E). The anti-PvDBP-RII Sal 1/7.18/P sera had a higher overall inhibitory response than any of the single variant anti-PvDBP-RII sera, even against PvDBP-RII variants not included in the mixed variant vaccination. Although it had a lower titer, the anti-PvDBP-RII DEKnull sera recognized and inhibited binding to the natural PvDBP-RII variants suggesting that it contains antibodies to shared neutralizing epitopes. FIGS. 39-40E show additional analysis comparing the $IC_{50}$ values of the anti-PvDBP-RII sera.

Example 18

Assessment of Anamnestic Boost

The anamnestic boost (Group 2) study determined if naturally occurring PvDBP-RII variants could elicit a memory response in mice initially immunized with synthetic variant PvDBP-RII DEKnull. Group 2 mice were immunized on Days 0 and 21 with either PvDBP-RII DEKnull or PvDBP-RII Sal 1 (control antigen). Initial test bleeds were taken on Day 42 to determine baseline IgG levels and were monitored on a monthly basis until peak IgG levels had dropped approximately 50% (FIG. 15). On Day 217 an intermediate test bleed was taken and mice received an anamnestic boost on Day 224, followed by sacrifice and final bleed on Day 245. ELISA analysis of the individual serum samples for Days 42, 217 and 245 can be seen in FIGS. 41A-43F. There was no significant difference between the serum samples from any test bleed day (Day 42 p=0.056; Day 217 p=0.067; Day 245 p=0.063). Serum samples on Day 42 and Day 217 were tittered against the prime immunization antigen (either PvDBP-RII DEKnull or PvDBP-RII Sal 1). Day 245 serum samples were tittered against their respective anamnestic boost antigens. FIGS. 44A-44F show the Day 42, 217 and 245 curves for each cohort. In all cases the IgG levels dropped significantly between Day 42 and Day 217.

Figure 44A:
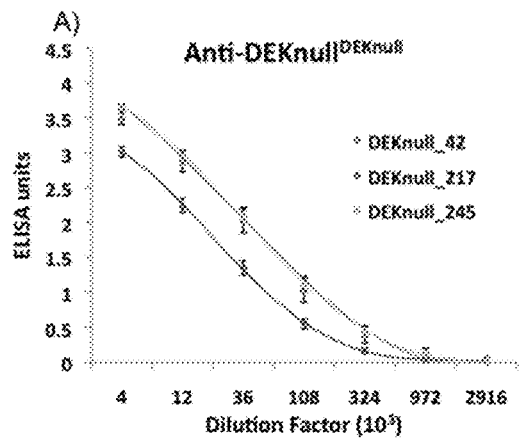
FIGS. 44A-44F are a series of graphs illustrating the memory responses following anamnestic boost.
Figure 44B:
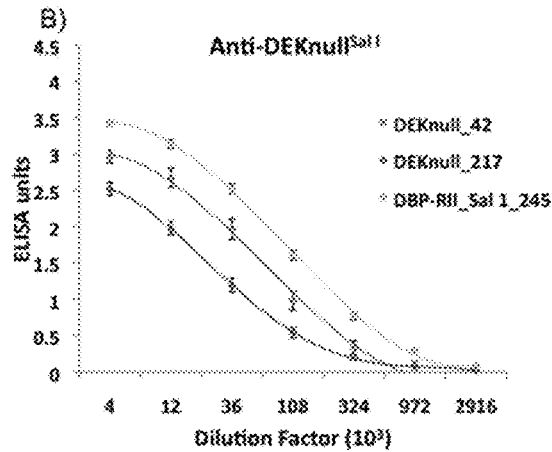
Figure 44C:
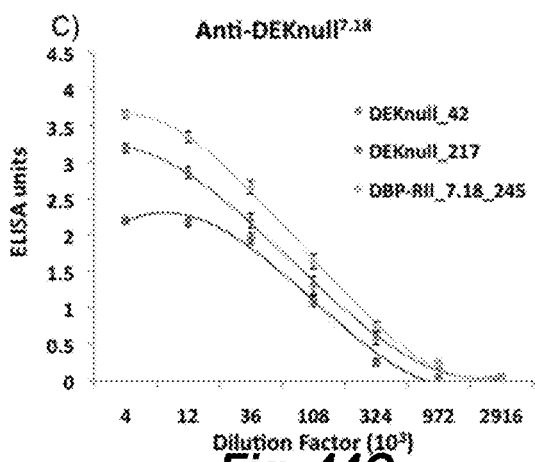
Figure 44D:
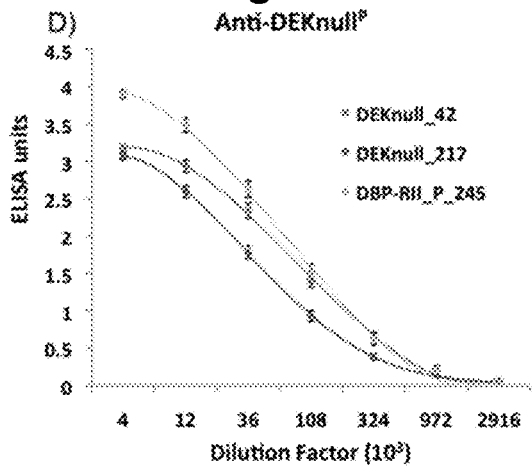
Figure 44E:
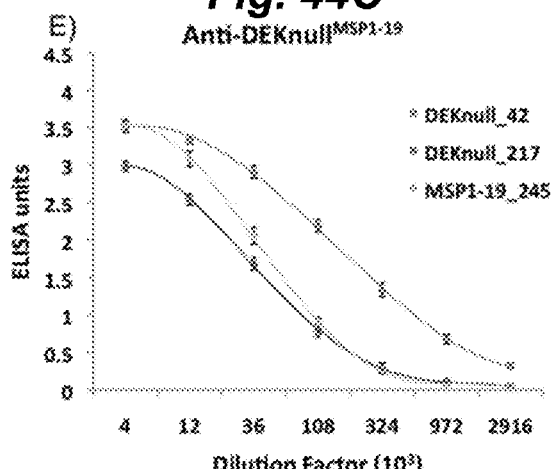
Figure 44F:
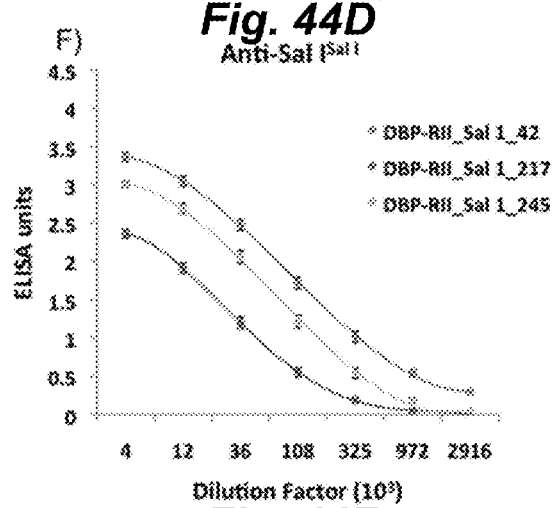
Figure 45:
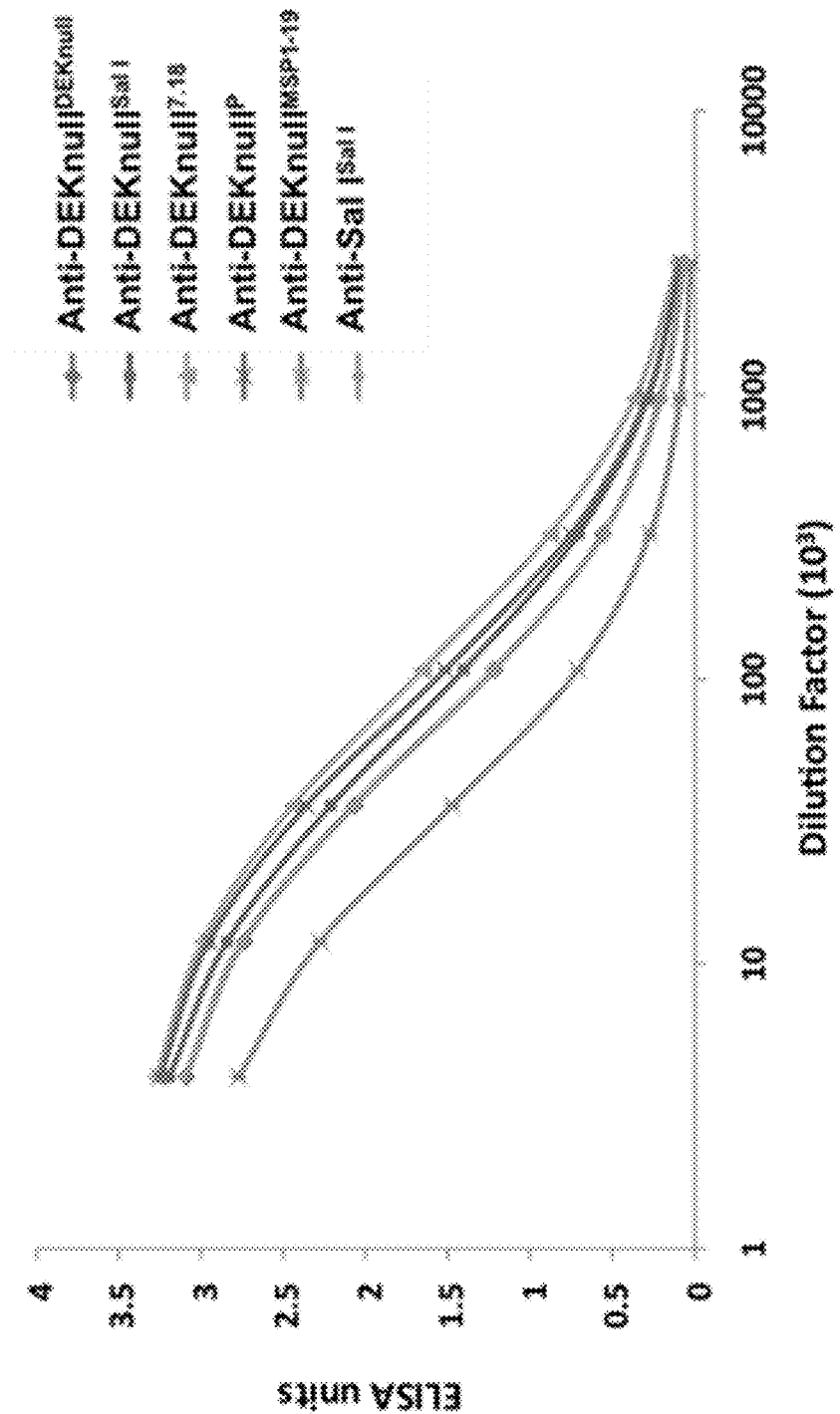
FIG. 45 is a graph illustrating the assessment of reactivity of all anamnestic boost anti-sera against antigen PvDBP-RII Sal 1.
Figure 46:
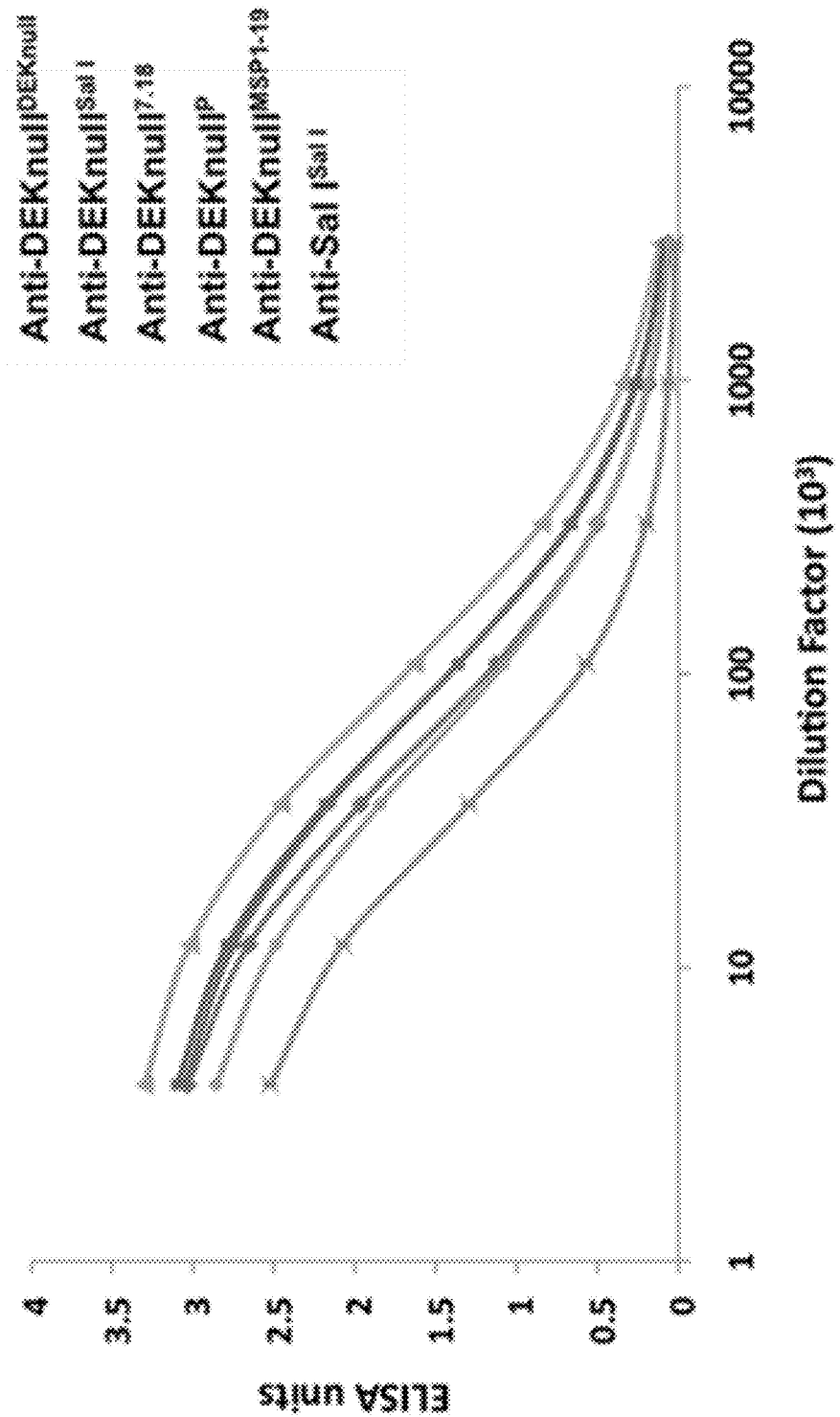
FIG. 46 is a graph illustrating the assessment of reactivity of all anamnestic boost anti-sera against antigen PvDBP-RII 7.18.
Figure 47:
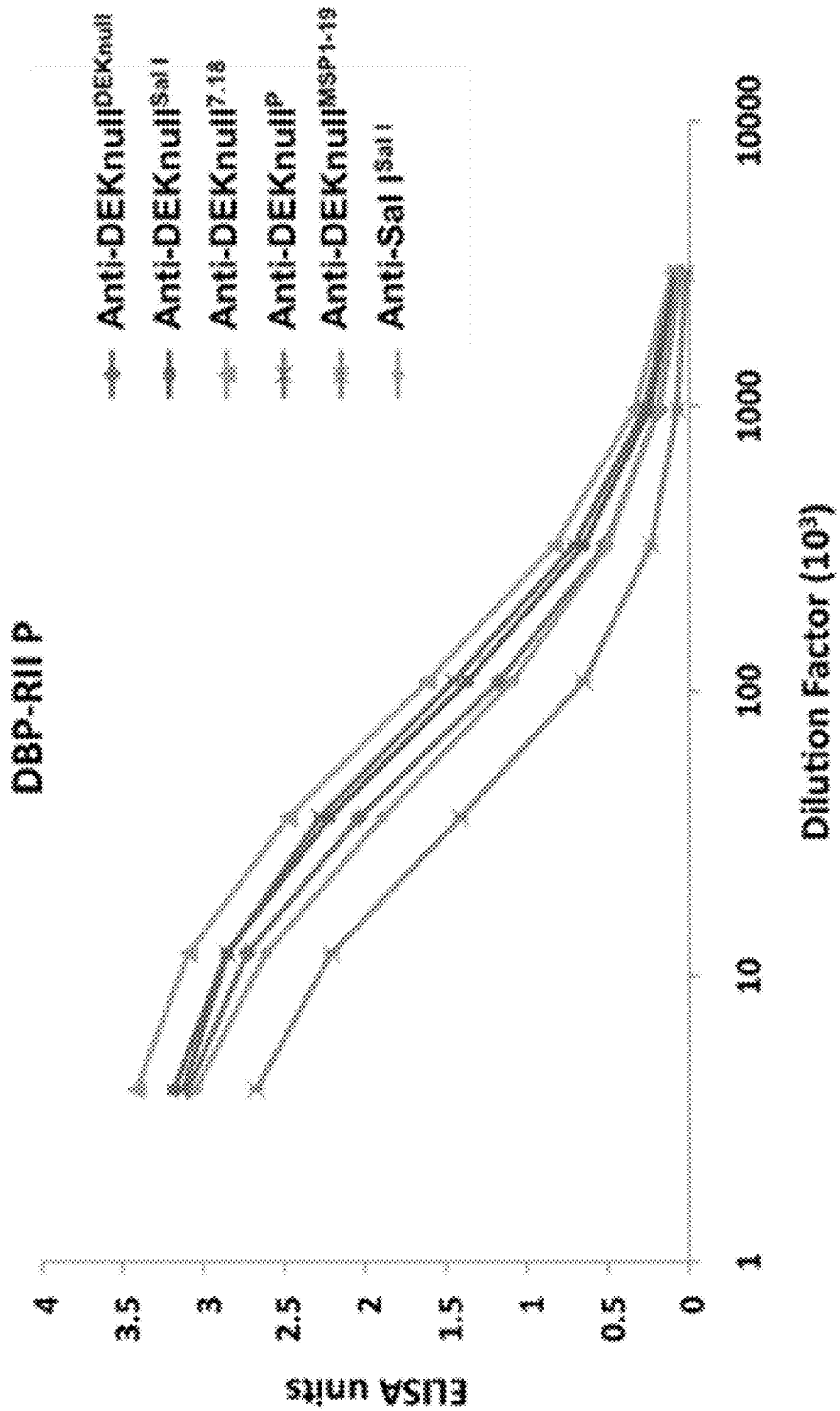
FIG. 47 is a graph illustrating the assessment of reactivity of all anamnestic boost anti-sera against antigen PvDBP-RII P.
Figure 48:
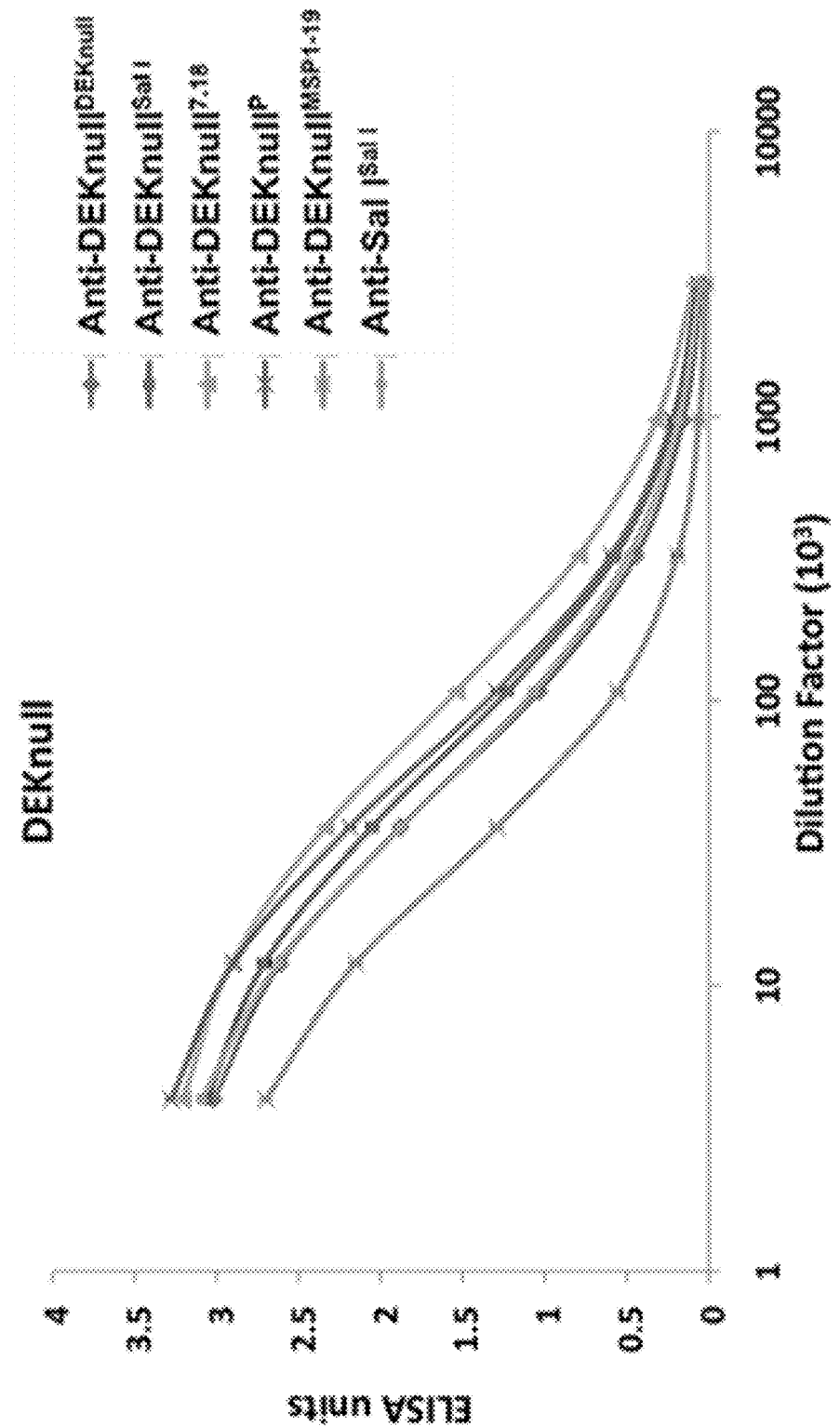
FIG. 48 is a graph illustrating the assessment of reactivity of all anamnestic boost anti-sera against antigen PvDBP-RII DEKnull.

All PvDBP-RII cohorts produced a strong memory response to anamnestic boost (as shown in FIGS. 16-18 and FIGS. 44A-44F). Following anamnestic boost, IgG levels rebounded to at or above Day 42 levels for anti-DEKnull$^{DEKnull}$, anti-DEKnull$^{Sal\ 1}$, anti-DEKnull$^{7.18}$ and anti-DEKnull$^P$ sera (FIGS. 44A-44D). Anti-DEKnull$^{MSP1-19}$ sera, which received an anamnestic boost of negative control antigen PvMSP1-19, did not show a significant memory response on Day 245 (FIG. 44E). Anti-Sal 1$^{Sal\ 1}$ IgG levels did increase following anamnestic boost, but not to the peak levels seen on Day 42 (FIG. 44F). A summary of the time course for all anti-sera can be seen in FIG. 16. FIG. 17 shows the average Day 42 baseline and Day 217 intermediate IgG curves for all the DEKnull cohorts and the individual Day 245 final IgG curves for each DEKnull cohort. FIG. 18 shows the IgG response of each cohort to anamnestic boost at a single point on the log phase of the curve (EU=1.5).

FIGS. 45-48 show the full curves of each antisera against each PvDBP-RII antigen. All PvDBP-RII DEKnull anamnestic responses were higher than with Sal 1$^{Sal\ 1}$ immunization. Antibodies within each PvDBP-RII cohort had similar heterologous PvDBP-RII reactivity but differences were observed in antibody responses between cohorts. Bonferroni multiple comparisons analysis indicates the anti-DEKnull$^{7.18}$ sera had the strongest memory response (p<0.05), followed by anti-DEKnull$^P$ and anti-DEKnull$^{Sal\ 1}$ (which were not significantly different from each other). Boosting with the homologous antigen (anti-DEKnull$^{DEKnull}$ and anti-Sal 1$^{Sal\ 1}$) did not result in an equally strong memory response (p<0.05) and boosting with the negative control antigen (anti-DEKnull$^{MSP1-19}$) did not result in a meaningful rebound of IgG levels.

What is claimed:

1. A method of eliciting in a subject an immune response, comprising administering to the subject an immunogenic composition comprising an engineered *Plasmodium vivax* Duffy Binding Protein (PvDBPII) comprising a modified region corresponding to an dominant immunogenic polymorphic B-cell epitope region of a native PvDBPII, wherein said modified region comprises the amino acid sequence SEQ ID NO: 4 (ASTAATSRTS), and wherein said modified region has reduced immunogenic dominance when compared to the region of a native PvDBPII comprising the amino acid sequence SEQ ID NO: 3 (DEKAQQRRKQWWNESK), and wherein the elicited immune response has increased binding specificity for conserved Duffy binding epitopes of a *Plasmodium* Duffy Binding Protein when compared to an immune response generated by a natural PvDBPII.

2. The method of claim 1, wherein the immunogenic composition comprises the engineered PvDBPII and an immunoadjuvant.

3. The method of claim 1, wherein the engineered PvDBPII has fewer polymorphic amino acids when compared to an dominant immunogenic polymorphic B-cell epitopic region of a native PvDBP.

4. The method of claim 1, wherein the modified region of the engineered PvDBPII consists essentially of the amino acid sequence SEQ ID NO: 4 (ASTAATSRTS).

5. The method of claim 1, wherein the engineered *Plasmodium vivax* Duffy Binding Protein comprises the amino acid sequence having at least 95% sequence identity with the sequence SEQ ID NO: 2.

6. The method of claim 1, wherein the engineered *Plasmodium vivax* Duffy Binding Protein has the amino acid sequence SEQ ID NO: 2.

* * * * *